(12) United States Patent
Song et al.

(10) Patent No.: US 11,845,951 B2
(45) Date of Patent: Dec. 19, 2023

(54) GENE MANIPULATION FOR TREATMENT OF RETINAL DYSFUNCTION DISORDER

(71) Applicants: TOOLGEN INCORPORATED, Seoul (KR); SEOUL NATIONAL UNIVERSITY R&DB FOUNDATION, Seoul (KR); SEOUL NATIONAL UNIVERSITY HOSPITAL, Seoul (KR)

(72) Inventors: Dong Woo Song, Seoul (KR); Jung Min Lee, Gyeongsangbuk-do (KR); Un Gi Kim, Seoul (KR); Jeong Hun Kim, Seoul (KR); Dong Hyun Jo, Seoul (KR)

(73) Assignees: TOOLGEN INCORPORATED, Seoul (KR); SEOUL NATIONAL UNIVERSITY R&DB FOUNDATION, Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 658 days.

(21) Appl. No.: 16/650,993

(22) PCT Filed: Sep. 28, 2018

(86) PCT No.: PCT/KR2018/011522
§ 371 (c)(1),
(2) Date: Mar. 26, 2020

(87) PCT Pub. No.: WO2019/066549
PCT Pub. Date: Apr. 4, 2019

(65) Prior Publication Data
US 2020/0277630 A1    Sep. 3, 2020

Related U.S. Application Data

(60) Provisional application No. 62/565,838, filed on Sep. 29, 2017.

(51) Int. Cl.
*C12N 15/86*    (2006.01)
*C12N 15/113*    (2010.01)
(Continued)

(52) U.S. Cl.
CPC .............. *C12N 15/86* (2013.01); *A61P 27/02* (2018.01); *C12N 9/22* (2013.01); *C12N 15/113* (2013.01);
(Continued)

(58) Field of Classification Search
CPC .. A61K 48/00; C12N 15/113; C12N 15/1137; C12N 2310/20; C12N 15/86; C12N 2800/80
See application file for complete search history.

(56) References Cited

U.S. PATENT DOCUMENTS

2010/0076057 A1    3/2010  Sontheimer et al.

FOREIGN PATENT DOCUMENTS

EP    3009511 A2    4/2016
WO    WO-2013176772 A1 *  11/2013 ........... A01H 6/4684

OTHER PUBLICATIONS

Hur, Junho, el al. (2016) "Targeted mutagenesis in mice by electroporation of Cpf1 ribonucleoproteins.", *Nat. Biotechnol.*, 34(8):807-808.
(Continued)

*Primary Examiner* — Terra C Gibbs
(74) *Attorney, Agent, or Firm* — Harness, Dickey & Pierce, P.L.C.

(57) ABSTRACT

The present invention relates to a composition for gene manipulation for treating or improving a retinal dysfunction disease or a method using the same. More particularly, the present invention relates to a composition for gene manipulation including a guide nucleic acid capable of targeting a retinal function-forming gene and a method of treating or improving a disease caused by retinal dysfunction by arti-
(Continued)

ficially manipulating and/or correcting a retinal function-forming gene using the same.

10 Claims, 22 Drawing Sheets

Specification includes a Sequence Listing.

(51) Int. Cl.
C12N 9/22 (2006.01)
A61P 27/02 (2006.01)
A61K 48/00 (2006.01)

(52) U.S. Cl.
CPC .......... *A61K 48/00* (2013.01); *C12N 2310/20* (2017.05); *C12N 2800/80* (2013.01)

(56) References Cited

OTHER PUBLICATIONS

Lin, Mingkai el al. (2012) "Impacts of Hypoxia-inducible Factor-1 Knockout in the Retinal Pigment Epithelium on Choroidal Neovascularizalion.", *Invest. Ophthalmol. Vis. Sci.*, 53(I0):6197-6206.
Zetsche. Bernd et al. (2015) "Cpf1 is a single RNA-guided endonuclease of a Class 2 CRISPR-Cas system.", Cell, 163(3):759-771.
International Search Report, dated May 16, 2019, issued in International Patent Application No. PCT/KR2018/011522, with English language translation.

* cited by examiner

| Protein position | 39 | 40 | 41 | 42 | 43 | 44 | 45 | 46 |
|---|---|---|---|---|---|---|---|---|
| Human *RPE65* | ACC | GGC | AGT | CTC | CTT | CGA | TGT | GGG |
| Mouse *Rpe65* | ACT | GGC | AGT | CTC | CTC | CGA | TGT | GGG |
| Amino acid | T | G | S | L | L | R | C | G |

FIG. 20

SEQUENCE LISTING

<160> NUMBER OF SEQ ID NOS: 256

<210> SEQ ID NO 1
<211> LENGTH: 20
<212> TYPE: DNA
<213> ORGANISM: Homo sapiens

<400> SEQUENCE: 1
agtttcttgt aaccaccagc                                               20

<210> SEQ ID NO 2
<211> LENGTH: 20
<212> TYPE: DNA
<213> ORGANISM: Homo sapiens

<400> SEQUENCE: 2
tacatgagct gtgagcggcg                                               20

<210> SEQ ID NO 3
<211> LENGTH: 20
<212> TYPE: DNA
<213> ORGANISM: Homo sapiens

<400> SEQUENCE: 3
ccgctcacag ctcatgtaac                                               20

<210> SEQ ID NO 4
<211> LENGTH: 20
<212> TYPE: DNA
<213> ORGANISM: Homo sapiens

<400> SEQUENCE: 4
tcacagctca tgtaacaggt                                               20

<210> SEQ ID NO 5
<211> LENGTH: 20
<212> TYPE: DNA
<213> ORGANISM: Homo sapiens

<400> SEQUENCE: 5
ggagactgcc ggtgagccag                                               20

<210> SEQ ID NO 6
<211> LENGTH: 20
<212> TYPE: DNA
<213> ORGANISM: Homo sapiens

<400> SEQUENCE: 6
accggcagtc tccttcgatg                                               20

<210> SEQ ID NO 7
<211> LENGTH: 20
<212> TYPE: DNA
<213> ORGANISM: Homo sapiens

<400> SEQUENCE: 7
agtctccttc gatgtgggcc                                               20

<210> SEQ ID NO 8
<211> LENGTH: 20
<212> TYPE: DNA
<213> ORGANISM: Homo sapiens

<400> SEQUENCE: 8
agagtcctgg cccacatcga						20

<210> SEQ ID NO 9
<211> LENGTH: 20
<212> TYPE: DNA
<213> ORGANISM: Homo sapiens

<400> SEQUENCE: 9
gggcttgccc atcaaacagg						20

<210> SEQ ID NO 10
<211> LENGTH: 20
<212> TYPE: DNA
<213> ORGANISM: Homo sapiens

<400> SEQUENCE: 10
taaagtcaaa cttgtgcagg						20

<210> SEQ ID NO 11
<211> LENGTH: 20
<212> TYPE: DNA
<213> ORGANISM: Homo sapiens

<400> SEQUENCE: 11
tccgcactga tgcttacgta						20

<210> SEQ ID NO 12
<211> LENGTH: 20
<212> TYPE: DNA
<213> ORGANISM: Homo sapiens

<400> SEQUENCE: 12
ccgcactgat gcttacgtac						20

<210> SEQ ID NO 13
<211> LENGTH: 20
<212> TYPE: DNA
<213> ORGANISM: Homo sapiens

<400> SEQUENCE: 13
cccgtacgta agcatcagtg						20

<210> SEQ ID NO 14
<211> LENGTH: 20
<212> TYPE: DNA
<213> ORGANISM: Homo sapiens

<400> SEQUENCE: 14
tacgggcaat gactgagaaa						20

<210> SEQ ID NO 15
<211> LENGTH: 20
<212> TYPE: DNA
<213> ORGANISM: Homo sapiens

<400> SEQUENCE: 15
aggatcgtca taacagaatt						20

<210> SEQ ID NO 16
<211> LENGTH: 20
<212> TYPE: DNA
<213> ORGANISM: Homo sapiens

```
<400> SEQUENCE: 16
ccactgggta gacattaaca                                          20

<210> SEQ ID NO 17
<211> LENGTH: 20
<212> TYPE: DNA
<213> ORGANISM: Homo sapiens

<400> SEQUENCE: 17
cgtagtaatc ttcccccact                                          20

<210> SEQ ID NO 18
<211> LENGTH: 20
<212> TYPE: DNA
<213> ORGANISM: Homo sapiens

<400> SEQUENCE: 18
gcgtagtaat cttcccccac                                          20

<210> SEQ ID NO 19
<211> LENGTH: 20
<212> TYPE: DNA
<213> ORGANISM: Homo sapiens

<400> SEQUENCE: 19
gcaactatgt ctctgtcaat                                          20

<210> SEQ ID NO 20
<211> LENGTH: 20
<212> TYPE: DNA
<213> ORGANISM: Homo sapiens

<400> SEQUENCE: 20
caactatgtc tctgtcaatg                                          20

<210> SEQ ID NO 21
<211> LENGTH: 20
<212> TYPE: DNA
<213> ORGANISM: Homo sapiens

<400> SEQUENCE: 21
ttcaatgtgg gggtgagcag                                          20

<210> SEQ ID NO 22
<211> LENGTH: 20
<212> TYPE: DNA
<213> ORGANISM: Homo sapiens

<400> SEQUENCE: 22
caccccacac ttgaaaatga                                          20

<210> SEQ ID NO 23
<211> LENGTH: 20
<212> TYPE: DNA
<213> ORGANISM: Homo sapiens

<400> SEQUENCE: 23
cggttccatc attttcaatg                                          20

<210> SEQ ID NO 24
<211> LENGTH: 20
<212> TYPE: DNA
<213> ORGANISM: Homo sapiens
```

```
<400> SEQUENCE: 24
gatggaaccg tttacaatat                                              20

<210> SEQ ID NO 25
<211> LENGTH: 20
<212> TYPE: DNA
<213> ORGANISM: Homo sapiens

<400> SEQUENCE: 25
gcttgaatcg gtcactgcag                                              20

<210> SEQ ID NO 26
<211> LENGTH: 20
<212> TYPE: DNA
<213> ORGANISM: Homo sapiens

<400> SEQUENCE: 26
gaacgtaaga tggcttgaat                                              20

<210> SEQ ID NO 27
<211> LENGTH: 20
<212> TYPE: DNA
<213> ORGANISM: Homo sapiens

<400> SEQUENCE: 27
agttacctat gaacgtaaga                                              20

<210> SEQ ID NO 28
<211> LENGTH: 20
<212> TYPE: DNA
<213> ORGANISM: Homo sapiens

<400> SEQUENCE: 28
tcccaactat atcgtttttg                                              20

<210> SEQ ID NO 29
<211> LENGTH: 20
<212> TYPE: DNA
<213> ORGANISM: Homo sapiens

<400> SEQUENCE: 29
tccacaaaaa cgatatagtt                                              20

<210> SEQ ID NO 30
<211> LENGTH: 20
<212> TYPE: DNA
<213> ORGANISM: Homo sapiens

<400> SEQUENCE: 30
atatctaaga cttaccccca                                              20

<210> SEQ ID NO 31
<211> LENGTH: 20
<212> TYPE: DNA
<213> ORGANISM: Homo sapiens

<400> SEQUENCE: 31
tagccaattt acgtgagaac                                              20

<210> SEQ ID NO 32
<211> LENGTH: 20
<212> TYPE: DNA
```

```
<213> ORGANISM: Homo sapiens

<400> SEQUENCE: 32
agccaattta cgtgagaact                                               20

<210> SEQ ID NO 33
<211> LENGTH: 20
<212> TYPE: DNA
<213> ORGANISM: Homo sapiens

<400> SEQUENCE: 33
ttcaggttgg ggagcctttc                                               20

<210> SEQ ID NO 34
<211> LENGTH: 20
<212> TYPE: DNA
<213> ORGANISM: Homo sapiens

<400> SEQUENCE: 34
aggctcccca acctgaagtt                                               20

<210> SEQ ID NO 35
<211> LENGTH: 20
<212> TYPE: DNA
<213> ORGANISM: Homo sapiens

<400> SEQUENCE: 35
gttaccttgt caatattcaa                                               20

<210> SEQ ID NO 36
<211> LENGTH: 20
<212> TYPE: DNA
<213> ORGANISM: Homo sapiens

<400> SEQUENCE: 36
tgtgcagtga cgagactatc                                               20

<210> SEQ ID NO 37
<211> LENGTH: 20
<212> TYPE: DNA
<213> ORGANISM: Homo sapiens

<400> SEQUENCE: 37
cagtgacgag actatctggc                                               20

<210> SEQ ID NO 38
<211> LENGTH: 20
<212> TYPE: DNA
<213> ORGANISM: Homo sapiens

<400> SEQUENCE: 38
atcaattacc agaagtattg                                               20

<210> SEQ ID NO 39
<211> LENGTH: 20
<212> TYPE: DNA
<213> ORGANISM: Homo sapiens

<400> SEQUENCE: 39
aaaccttaca catatgcgta                                               20

<210> SEQ ID NO 40
<211> LENGTH: 20
```

```
<212> TYPE: DNA
<213> ORGANISM: Homo sapiens

<400> SEQUENCE: 40
agtccatacg catatgtgta                                              20

<210> SEQ ID NO 41
<211> LENGTH: 20
<212> TYPE: DNA
<213> ORGANISM: Homo sapiens

<400> SEQUENCE: 41
tacacatatg cgtatggact                                              20

<210> SEQ ID NO 42
<211> LENGTH: 20
<212> TYPE: DNA
<213> ORGANISM: Homo sapiens

<400> SEQUENCE: 42
gaaggattaa ttaccctatc                                              20

<210> SEQ ID NO 43
<211> LENGTH: 20
<212> TYPE: DNA
<213> ORGANISM: Homo sapiens

<400> SEQUENCE: 43
tgaagttgcc cgggctgaag                                              20

<210> SEQ ID NO 44
<211> LENGTH: 20
<212> TYPE: DNA
<213> ORGANISM: Homo sapiens

<400> SEQUENCE: 44
gttaatctcc acttcagccc                                              20

<210> SEQ ID NO 45
<211> LENGTH: 22
<212> TYPE: DNA
<213> ORGANISM: Homo sapiens

<400> SEQUENCE: 45
cacctgtttg atgggcaagc cc                                           22

<210> SEQ ID NO 46
<211> LENGTH: 22
<212> TYPE: DNA
<213> ORGANISM: Homo sapiens

<400> SEQUENCE: 46
tttgacttta agaaggaca tg                                            22

<210> SEQ ID NO 47
<211> LENGTH: 22
<212> TYPE: DNA
<213> ORGANISM: Homo sapiens

<400> SEQUENCE: 47
tgtttcaatg tccttcaggt tc                                           22

<210> SEQ ID NO 48
```

-continued

```
<211> LENGTH: 22
<212> TYPE: DNA
<213> ORGANISM: Homo sapiens

<400> SEQUENCE: 48
tcaggttcat ccgcactgat gc                                              22

<210> SEQ ID NO 49
<211> LENGTH: 22
<212> TYPE: DNA
<213> ORGANISM: Homo sapiens

<400> SEQUENCE: 49
gacgatcctt ttctcagtca tt                                              22

<210> SEQ ID NO 50
<211> LENGTH: 22
<212> TYPE: DNA
<213> ORGANISM: Homo sapiens

<400> SEQUENCE: 50
gaaaaggatc gtcataacag aa                                              22

<210> SEQ ID NO 51
<211> LENGTH: 22
<212> TYPE: DNA
<213> ORGANISM: Homo sapiens

<400> SEQUENCE: 51
atatattctt gcagggatct gg                                              22

<210> SEQ ID NO 52
<211> LENGTH: 22
<212> TYPE: DNA
<213> ORGANISM: Homo sapiens

<400> SEQUENCE: 52
cccagtgggg gaagattact ac                                              22

<210> SEQ ID NO 53
<211> LENGTH: 22
<212> TYPE: DNA
<213> ORGANISM: Homo sapiens

<400> SEQUENCE: 53
atccaataag caagtcagag at                                              22

<210> SEQ ID NO 54
<211> LENGTH: 22
<212> TYPE: DNA
<213> ORGANISM: Homo sapiens

<400> SEQUENCE: 54
cttgaatcgg tcactgcagg gg                                              22

<210> SEQ ID NO 55
<211> LENGTH: 22
<212> TYPE: DNA
<213> ORGANISM: Homo sapiens

<400> SEQUENCE: 55
ctcccaacta tatcgttttt gt                                              22
```

```
<210> SEQ ID NO 56
<211> LENGTH: 22
<212> TYPE: DNA
<213> ORGANISM: Homo sapiens

<400> SEQUENCE: 56
catattgctg acaaaaaaag ga                                              22

<210> SEQ ID NO 57
<211> LENGTH: 22
<212> TYPE: DNA
<213> ORGANISM: Homo sapiens

<400> SEQUENCE: 57
ggagaagttc tgtatttatt at                                              22

<210> SEQ ID NO 58
<211> LENGTH: 22
<212> TYPE: DNA
<213> ORGANISM: Homo sapiens

<400> SEQUENCE: 58
tcctttcaac ctcttccatc ac                                              22

<210> SEQ ID NO 59
<211> LENGTH: 22
<212> TYPE: DNA
<213> ORGANISM: Homo sapiens

<400> SEQUENCE: 59
ctccccaacc tgaagttagg ag                                              22

<210> SEQ ID NO 60
<211> LENGTH: 22
<212> TYPE: DNA
<213> ORGANISM: Homo sapiens

<400> SEQUENCE: 60
ggttaccttg tcaatattca aa                                              22

<210> SEQ ID NO 61
<211> LENGTH: 22
<212> TYPE: DNA
<213> ORGANISM: Homo sapiens

<400> SEQUENCE: 61
aggcaagaat ttagtcacgc tc                                              22

<210> SEQ ID NO 62
<211> LENGTH: 22
<212> TYPE: DNA
<213> ORGANISM: Homo sapiens

<400> SEQUENCE: 62
ggctccagcc agatagtctc gt                                              22

<210> SEQ ID NO 63
<211> LENGTH: 22
<212> TYPE: DNA
<213> ORGANISM: Homo sapiens

<400> SEQUENCE: 63
ttaccagaag tattgtggga aa                                              22
```

```
<210> SEQ ID NO 64
<211> LENGTH: 22
<212> TYPE: DNA
<213> ORGANISM: Homo sapiens

<400> SEQUENCE: 64
tacgcatatg tgtaaggttt cc                                               22

<210> SEQ ID NO 65
<211> LENGTH: 22
<212> TYPE: DNA
<213> ORGANISM: Homo sapiens

<400> SEQUENCE: 65
ggaacaaagt gattcaagcc aa                                               22

<210> SEQ ID NO 66
<211> LENGTH: 22
<212> TYPE: DNA
<213> ORGANISM: Homo sapiens

<400> SEQUENCE: 66
acttgggttt ggcaagagcc tg                                               22

<210> SEQ ID NO 67
<211> LENGTH: 22
<212> TYPE: DNA
<213> ORGANISM: Homo sapiens

<400> SEQUENCE: 67
ctgggctcac caccacactc ag                                               22

<210> SEQ ID NO 68
<211> LENGTH: 22
<212> TYPE: DNA
<213> ORGANISM: Homo sapiens

<400> SEQUENCE: 68
tttgtcctgc tcctgggctc ac                                               22

<210> SEQ ID NO 69
<211> LENGTH: 22
<212> TYPE: DNA
<213> ORGANISM: Homo sapiens

<400> SEQUENCE: 69
catggactgt tcaaaaaatc tt                                               22

<210> SEQ ID NO 70
<211> LENGTH: 24
<212> TYPE: DNA
<213> ORGANISM: Artificial Sequence
<220> FEATURE:
<223> OTHER INFORMATION: primer

<400> SEQUENCE: 70
actctgtcca aagacctcat gtga                                             24

<210> SEQ ID NO 71
<211> LENGTH: 24
<212> TYPE: DNA
<213> ORGANISM: Artificial Sequence
<220> FEATURE:
<223> OTHER INFORMATION: primer
```

```
<400> SEQUENCE: 71
agctgacaaa taacaaatag gcac                                      24

<210> SEQ ID NO 72
<211> LENGTH: 24
<212> TYPE: DNA
<213> ORGANISM: Artificial Sequence
<220> FEATURE:
<223> OTHER INFORMATION: primer

<400> SEQUENCE: 72
agctgacaaa taacaaatag gcac                                      24

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
tgcctctatc tctgcggact                                           20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
tgcctctatc tctgcggact                                           20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
tgcctctatc tctgcggact                                           20

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
tgcctctatc tctgcggact                                           20

<210> SEQ ID NO 77
<211> LENGTH: 20
<212> TYPE: DNA
<213> ORGANISM: Artificial Sequence
<220> FEATURE:
<223> OTHER INFORMATION: primer

<400> SEQUENCE: 77
ctgccttacc aaggacaagc                                           20

<210> SEQ ID NO 78
```

```
<211> LENGTH: 20
<212> TYPE: DNA
<213> ORGANISM: Artificial Sequence
<220> FEATURE:
<223> OTHER INFORMATION: primer

<400> SEQUENCE: 78
ctgccttacc aaggacaagc                                           20

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
ctgccttacc aaggacaagc                                           20

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
ctgccttacc aaggacaagc                                           20

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
gctgtacgga ttgctcctgt                                           20

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
gctgtacgga ttgctcctgt                                           20

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
ttccaggtta ctgaacccaa a                                         21

<210> SEQ ID NO 84
<211> LENGTH: 21
<212> TYPE: DNA
<213> ORGANISM: Artificial Sequence
<220> FEATURE:
<223> OTHER INFORMATION: primer

<400> SEQUENCE: 84
```

```
ttccaggtta ctgaacccaa a                                              21

<210> SEQ ID NO 85
<211> LENGTH: 21
<212> TYPE: DNA
<213> ORGANISM: Artificial Sequence
<220> FEATURE:
<223> OTHER INFORMATION: primer

<400> SEQUENCE: 85
ttccaggtta ctgaacccaa a                                              21

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ccttctctca actggaggac a                                              21

<210> SEQ ID NO 87
<211> LENGTH: 21
<212> TYPE: DNA
<213> ORGANISM: Artificial Sequence
<220> FEATURE:
<223> OTHER INFORMATION: primer

<400> SEQUENCE: 87
ccttctctca actggaggac a                                              21

<210> SEQ ID NO 88
<211> LENGTH: 24
<212> TYPE: DNA
<213> ORGANISM: Artificial Sequence
<220> FEATURE:
<223> OTHER INFORMATION: primer

<400> SEQUENCE: 88
ggctctggaa gttactctca ctag                                           24

<210> SEQ ID NO 89
<211> LENGTH: 24
<212> TYPE: DNA
<213> ORGANISM: Artificial Sequence
<220> FEATURE:
<223> OTHER INFORMATION: primer

<400> SEQUENCE: 89
tgccctgtac accccaaata caca                                           24

<210> SEQ ID NO 90
<211> LENGTH: 24
<212> TYPE: DNA
<213> ORGANISM: Artificial Sequence
<220> FEATURE:
<223> OTHER INFORMATION: primer

<400> SEQUENCE: 90
cactttggat cctctggcaa ctca                                           24

<210> SEQ ID NO 91
<211> LENGTH: 24
<212> TYPE: DNA
```

```
<213> ORGANISM: Artificial Sequence
<220> FEATURE:
<223> OTHER INFORMATION: primer

<400> SEQUENCE: 91
cccatggaca gagttctata gaca                                              24

<210> SEQ ID NO 92
<211> LENGTH: 24
<212> TYPE: DNA
<213> ORGANISM: Artificial Sequence
<220> FEATURE:
<223> OTHER INFORMATION: primer

<400> SEQUENCE: 92
gccaaatata tccaaagata gtgg                                              24

<210> SEQ ID NO 93
<211> LENGTH: 24
<212> TYPE: DNA
<213> ORGANISM: Artificial Sequence
<220> FEATURE:
<223> OTHER INFORMATION: primer

<400> SEQUENCE: 93
atggaatacg tgcctttgca ggaa                                              24

<210> SEQ ID NO 94
<211> LENGTH: 24
<212> TYPE: DNA
<213> ORGANISM: Artificial Sequence
<220> FEATURE:
<223> OTHER INFORMATION: primer

<400> SEQUENCE: 94
ctctagtcta ccaccctgag aact                                              24

<210> SEQ ID NO 95
<211> LENGTH: 24
<212> TYPE: DNA
<213> ORGANISM: Artificial Sequence
<220> FEATURE:
<223> OTHER INFORMATION: primer

<400> SEQUENCE: 95
tgaagagaat cactgcaggg gatt                                              24

<210> SEQ ID NO 96
<211> LENGTH: 24
<212> TYPE: DNA
<213> ORGANISM: Artificial Sequence
<220> FEATURE:
<223> OTHER INFORMATION: primer

<400> SEQUENCE: 96
gttggttacc cctcagataa aggt                                              24

<210> SEQ ID NO 97
<211> LENGTH: 24
<212> TYPE: DNA
<213> ORGANISM: Artificial Sequence
<220> FEATURE:
<223> OTHER INFORMATION: primer

<400> SEQUENCE: 97
aggaagctga gtggctaatg gtaa                                              24
```

<210> SEQ ID NO 98
<211> LENGTH: 24
<212> TYPE: DNA
<213> ORGANISM: Artificial Sequence
<220> FEATURE:
<223> OTHER INFORMATION: primer

<400> SEQUENCE: 98
cctgagaaag ctaatactgt ccac                                          24

<210> SEQ ID NO 99
<211> LENGTH: 24
<212> TYPE: DNA
<213> ORGANISM: Artificial Sequence
<220> FEATURE:
<223> OTHER INFORMATION: primer

<400> SEQUENCE: 99
atccccaaaa ccccttatac cctt                                          24

<210> SEQ ID NO 100
<211> LENGTH: 24
<212> TYPE: DNA
<213> ORGANISM: Artificial Sequence
<220> FEATURE:
<223> OTHER INFORMATION: primer

<400> SEQUENCE: 100
gctaaggggt cagttctgca ctca                                          24

<210> SEQ ID NO 101
<211> LENGTH: 24
<212> TYPE: DNA
<213> ORGANISM: Artificial Sequence
<220> FEATURE:
<223> OTHER INFORMATION: primer

<400> SEQUENCE: 101
ctgcatcacc attactacaa caca                                          24

<210> SEQ ID NO 102
<211> LENGTH: 24
<212> TYPE: DNA
<213> ORGANISM: Artificial Sequence
<220> FEATURE:
<223> OTHER INFORMATION: primer

<400> SEQUENCE: 102
gagtgagcca tcacagttgc agat                                          24

<210> SEQ ID NO 103
<211> LENGTH: 24
<212> TYPE: DNA
<213> ORGANISM: Artificial Sequence
<220> FEATURE:
<223> OTHER INFORMATION: primer

<400> SEQUENCE: 103
tgtacctcag ccttgagttt gagt                                          24

<210> SEQ ID NO 104
<211> LENGTH: 24
<212> TYPE: DNA
<213> ORGANISM: Artificial Sequence
<220> FEATURE:

```
<223> OTHER INFORMATION: primer

<400> SEQUENCE: 104
gccgattggg agatagttta caca                                      24

<210> SEQ ID NO 105
<211> LENGTH: 24
<212> TYPE: DNA
<213> ORGANISM: Artificial Sequence
<220> FEATURE:
<223> OTHER INFORMATION: primer

<400> SEQUENCE: 105
acgggggagg gagtaactta gcta                                      24

<210> SEQ ID NO 106
<211> LENGTH: 24
<212> TYPE: DNA
<213> ORGANISM: Artificial Sequence
<220> FEATURE:
<223> OTHER INFORMATION: primer

<400> SEQUENCE: 106
aagagcagtc agtgctctta acca                                      24

<210> SEQ ID NO 107
<211> LENGTH: 24
<212> TYPE: DNA
<213> ORGANISM: Artificial Sequence
<220> FEATURE:
<223> OTHER INFORMATION: primer

<400> SEQUENCE: 107
gcaggatgac agaaatgctt gttg                                      24

<210> SEQ ID NO 108
<211> LENGTH: 24
<212> TYPE: DNA
<213> ORGANISM: Artificial Sequence
<220> FEATURE:
<223> OTHER INFORMATION: primer

<400> SEQUENCE: 108
gcaggatgac agaaatgctt gttg                                      24

<210> SEQ ID NO 109
<211> LENGTH: 24
<212> TYPE: DNA
<213> ORGANISM: Artificial Sequence
<220> FEATURE:
<223> OTHER INFORMATION: primer

<400> SEQUENCE: 109
gagtggctca cttagcttct gcta                                      24

<210> SEQ ID NO 110
<211> LENGTH: 24
<212> TYPE: DNA
<213> ORGANISM: Artificial Sequence
<220> FEATURE:
<223> OTHER INFORMATION: primer

<400> SEQUENCE: 110
catctgttgt ggtgttgaaa gcca                                      24
```

-continued

```
<210> SEQ ID NO 111
<211> LENGTH: 24
<212> TYPE: DNA
<213> ORGANISM: Artificial Sequence
<220> FEATURE:
<223> OTHER INFORMATION: primer

<400> SEQUENCE: 111
ccatccaatc tcttcctggg agaa                                              24

<210> SEQ ID NO 112
<211> LENGTH: 24
<212> TYPE: DNA
<213> ORGANISM: Artificial Sequence
<220> FEATURE:
<223> OTHER INFORMATION: primer

<400> SEQUENCE: 112
ccagatgcaa accacagcat ccta                                              24

<210> SEQ ID NO 113
<211> LENGTH: 24
<212> TYPE: DNA
<213> ORGANISM: Artificial Sequence
<220> FEATURE:
<223> OTHER INFORMATION: primer

<400> SEQUENCE: 113
cccagaacct gtgctaaaga ttga                                              24

<210> SEQ ID NO 114
<211> LENGTH: 24
<212> TYPE: DNA
<213> ORGANISM: Artificial Sequence
<220> FEATURE:
<223> OTHER INFORMATION: primer

<400> SEQUENCE: 114
ctttccttgt ttcccctctg aaga                                              24

<210> SEQ ID NO 115
<211> LENGTH: 24
<212> TYPE: DNA
<213> ORGANISM: Artificial Sequence
<220> FEATURE:
<223> OTHER INFORMATION: primer

<400> SEQUENCE: 115
ctttccttgt ttcccctctg aaga                                              24

<210> SEQ ID NO 116
<211> LENGTH: 24
<212> TYPE: DNA
<213> ORGANISM: Artificial Sequence
<220> FEATURE:
<223> OTHER INFORMATION: primer

<400> SEQUENCE: 116
ctttccttgt ttcccctctg aaga                                              24

<210> SEQ ID NO 117
<211> LENGTH: 24
<212> TYPE: DNA
<213> ORGANISM: Artificial Sequence
<220> FEATURE:
<223> OTHER INFORMATION: primer
```

```
<400> SEQUENCE: 117
ctttccttgt ttcccctctg aaga                                           24

<210> SEQ ID NO 118
<211> LENGTH: 24
<212> TYPE: DNA
<213> ORGANISM: Artificial Sequence
<220> FEATURE:
<223> OTHER INFORMATION: primer

<400> SEQUENCE: 118
gtaggcaaag catccataca caca                                           24

<210> SEQ ID NO 119
<211> LENGTH: 24
<212> TYPE: DNA
<213> ORGANISM: Artificial Sequence
<220> FEATURE:
<223> OTHER INFORMATION: primer

<400> SEQUENCE: 119
aatgctatcc cgaaagaccc ctat                                           24

<210> SEQ ID NO 120
<211> LENGTH: 24
<212> TYPE: DNA
<213> ORGANISM: Artificial Sequence
<220> FEATURE:
<223> OTHER INFORMATION: primer

<400> SEQUENCE: 120
atggccaagc aatacttatg ctga                                           24

<210> SEQ ID NO 121
<211> LENGTH: 24
<212> TYPE: DNA
<213> ORGANISM: Artificial Sequence
<220> FEATURE:
<223> OTHER INFORMATION: primer

<400> SEQUENCE: 121
tggatgctga gtcattgctc taac                                           24

<210> SEQ ID NO 122
<211> LENGTH: 23
<212> TYPE: DNA
<213> ORGANISM: Artificial Sequence
<220> FEATURE:
<223> OTHER INFORMATION: primer

<400> SEQUENCE: 122
tggtgaggtc agtcatggac tta                                            23

<210> SEQ ID NO 123
<211> LENGTH: 23
<212> TYPE: DNA
<213> ORGANISM: Artificial Sequence
<220> FEATURE:
<223> OTHER INFORMATION: primer

<400> SEQUENCE: 123
tggtgaggtc agtcatggac tta                                            23

<210> SEQ ID NO 124
<211> LENGTH: 20
```

```
<212> TYPE: DNA
<213> ORGANISM: Artificial Sequence
<220> FEATURE:
<223> OTHER INFORMATION: primer

<400> SEQUENCE: 124
aaaccacctg atccctctcc                                           20

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
aaaccacctg atccctctcc                                           20

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
aaaccacctg atccctctcc                                           20

<210> SEQ ID NO 127
<211> LENGTH: 20
<212> TYPE: DNA
<213> ORGANISM: Artificial Sequence
<220> FEATURE:
<223> OTHER INFORMATION: primer

<400> SEQUENCE: 127
aaaccacctg atccctctcc                                           20

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128
aggccctact ttgaggagga                                           20

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
aggccctact ttgaggagga                                           20

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
```
aggccctact ttgaggagga                                              20

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131
aggccctact ttgaggagga                                              20

<210> SEQ ID NO 132
<211> LENGTH: 21
<212> TYPE: DNA
<213> ORGANISM: Artificial Sequence
<220> FEATURE:
<223> OTHER INFORMATION: primer

<400> SEQUENCE: 132
tcaagccatg agagaaaaag g                                            21

<210> SEQ ID NO 133
<211> LENGTH: 21
<212> TYPE: DNA
<213> ORGANISM: Artificial Sequence
<220> FEATURE:
<223> OTHER INFORMATION: primer

<400> SEQUENCE: 133
tcaagccatg agagaaaaag g                                            21

<210> SEQ ID NO 134
<211> LENGTH: 20
<212> TYPE: DNA
<213> ORGANISM: Artificial Sequence
<220> FEATURE:
<223> OTHER INFORMATION: primer

<400> SEQUENCE: 134
cctagcactg tgtcccacct                                              20

<210> SEQ ID NO 135
<211> LENGTH: 20
<212> TYPE: DNA
<213> ORGANISM: Artificial Sequence
<220> FEATURE:
<223> OTHER INFORMATION: primer

<400> SEQUENCE: 135
cctagcactg tgtcccacct                                              20

<210> SEQ ID NO 136
<211> LENGTH: 20
<212> TYPE: DNA
<213> ORGANISM: Artificial Sequence
<220> FEATURE:
<223> OTHER INFORMATION: primer

<400> SEQUENCE: 136
cctagcactg tgtcccacct                                              20

<210> SEQ ID NO 137
<211> LENGTH: 23
<212> TYPE: DNA
<213> ORGANISM: Artificial Sequence

```
<220> FEATURE:
<223> OTHER INFORMATION: primer

<400> SEQUENCE: 137
tgcacaaaat gctattctga cat                                          23

<210> SEQ ID NO 138
<211> LENGTH: 23
<212> TYPE: DNA
<213> ORGANISM: Artificial Sequence
<220> FEATURE:
<223> OTHER INFORMATION: primer

<400> SEQUENCE: 138
tgcacaaaat gctattctga cat                                          23

<210> SEQ ID NO 139
<211> LENGTH: 24
<212> TYPE: DNA
<213> ORGANISM: Artificial Sequence
<220> FEATURE:
<223> OTHER INFORMATION: primer

<400> SEQUENCE: 139
agccattcaa gtttctccct tgat                                         24

<210> SEQ ID NO 140
<211> LENGTH: 24
<212> TYPE: DNA
<213> ORGANISM: Artificial Sequence
<220> FEATURE:
<223> OTHER INFORMATION: primer

<400> SEQUENCE: 140
gacggtacat aaatgagcag cctt                                         24

<210> SEQ ID NO 141
<211> LENGTH: 24
<212> TYPE: DNA
<213> ORGANISM: Artificial Sequence
<220> FEATURE:
<223> OTHER INFORMATION: primer

<400> SEQUENCE: 141
tcccctttct ttgtaagcac tcct                                         24

<210> SEQ ID NO 142
<211> LENGTH: 24
<212> TYPE: DNA
<213> ORGANISM: Artificial Sequence
<220> FEATURE:
<223> OTHER INFORMATION: primer

<400> SEQUENCE: 142
gctgtcctcg aactcagaaa tcca                                         24

<210> SEQ ID NO 143
<211> LENGTH: 22
<212> TYPE: DNA
<213> ORGANISM: Artificial Sequence
<220> FEATURE:
<223> OTHER INFORMATION: primer

<400> SEQUENCE: 143
gtcagttgaa ccgtgtgaag tt                                           22
```

<210> SEQ ID NO 144
<211> LENGTH: 24
<212> TYPE: DNA
<213> ORGANISM: Artificial Sequence
<220> FEATURE:
<223> OTHER INFORMATION: primer

<400> SEQUENCE: 144
tcacaagtaa gggatgcttc ctgt                                           24

<210> SEQ ID NO 145
<211> LENGTH: 24
<212> TYPE: DNA
<213> ORGANISM: Artificial Sequence
<220> FEATURE:
<223> OTHER INFORMATION: primer

<400> SEQUENCE: 145
atcactaagc tgtgccaagt agca                                           24

<210> SEQ ID NO 146
<211> LENGTH: 24
<212> TYPE: DNA
<213> ORGANISM: Artificial Sequence
<220> FEATURE:
<223> OTHER INFORMATION: primer

<400> SEQUENCE: 146
cagggatgct taatgcactg tgaa                                           24

<210> SEQ ID NO 147
<211> LENGTH: 24
<212> TYPE: DNA
<213> ORGANISM: Artificial Sequence
<220> FEATURE:
<223> OTHER INFORMATION: primer

<400> SEQUENCE: 147
gttctcactt acatgtggaa ggct                                           24

<210> SEQ ID NO 148
<211> LENGTH: 24
<212> TYPE: DNA
<213> ORGANISM: Artificial Sequence
<220> FEATURE:
<223> OTHER INFORMATION: primer

<400> SEQUENCE: 148
tctggtttcc gttctccagt tcca                                           24

<210> SEQ ID NO 149
<211> LENGTH: 24
<212> TYPE: DNA
<213> ORGANISM: Artificial Sequence
<220> FEATURE:
<223> OTHER INFORMATION: primer

<400> SEQUENCE: 149
ttcccctccg aaaatcccct atcc                                           24

<210> SEQ ID NO 150
<211> LENGTH: 24
<212> TYPE: DNA
<213> ORGANISM: Artificial Sequence
<220> FEATURE:
<223> OTHER INFORMATION: primer

```
<400> SEQUENCE: 150
gtaccccagg tgctaaaagg gtct                                            24

<210> SEQ ID NO 151
<211> LENGTH: 23
<212> TYPE: DNA
<213> ORGANISM: Artificial Sequence
<220> FEATURE:
<223> OTHER INFORMATION: primer

<400> SEQUENCE: 151
cagtgccctc cctgacaatg tca                                             23

<210> SEQ ID NO 152
<211> LENGTH: 24
<212> TYPE: DNA
<213> ORGANISM: Artificial Sequence
<220> FEATURE:
<223> OTHER INFORMATION: primer

<400> SEQUENCE: 152
tgagattggg gtgcatctct ggaa                                            24

<210> SEQ ID NO 153
<211> LENGTH: 24
<212> TYPE: DNA
<213> ORGANISM: Artificial Sequence
<220> FEATURE:
<223> OTHER INFORMATION: primer

<400> SEQUENCE: 153
agtcatccta tagctctgga cagg                                            24

<210> SEQ ID NO 154
<211> LENGTH: 24
<212> TYPE: DNA
<213> ORGANISM: Artificial Sequence
<220> FEATURE:
<223> OTHER INFORMATION: primer

<400> SEQUENCE: 154
gctcatagtc ctctactgga tgga                                            24

<210> SEQ ID NO 155
<211> LENGTH: 24
<212> TYPE: DNA
<213> ORGANISM: Artificial Sequence
<220> FEATURE:
<223> OTHER INFORMATION: primer

<400> SEQUENCE: 155
gggtgcctaa gacacgtact aaag                                            24

<210> SEQ ID NO 156
<211> LENGTH: 23
<212> TYPE: DNA
<213> ORGANISM: Artificial Sequence
<220> FEATURE:
<223> OTHER INFORMATION: primer

<400> SEQUENCE: 156
aattactgtc ccgccaggat gga                                             23

<210> SEQ ID NO 157
```

```
<211> LENGTH: 24
<212> TYPE: DNA
<213> ORGANISM: Artificial Sequence
<220> FEATURE:
<223> OTHER INFORMATION: primer

<400> SEQUENCE: 157
tgccctgaga ccaaaggaat aaga                                                24

<210> SEQ ID NO 158
<211> LENGTH: 24
<212> TYPE: DNA
<213> ORGANISM: Artificial Sequence
<220> FEATURE:
<223> OTHER INFORMATION: primer

<400> SEQUENCE: 158
ccagaaagtg aggtctcatc tcca                                                24

<210> SEQ ID NO 159
<211> LENGTH: 24
<212> TYPE: DNA
<213> ORGANISM: Artificial Sequence
<220> FEATURE:
<223> OTHER INFORMATION: primer

<400> SEQUENCE: 159
ccagaaagtg aggtctcatc tcca                                                24

<210> SEQ ID NO 160
<211> LENGTH: 24
<212> TYPE: DNA
<213> ORGANISM: Artificial Sequence
<220> FEATURE:
<223> OTHER INFORMATION: primer

<400> SEQUENCE: 160
cgtcttatca ctagggttaa gggt                                                24

<210> SEQ ID NO 161
<211> LENGTH: 24
<212> TYPE: DNA
<213> ORGANISM: Artificial Sequence
<220> FEATURE:
<223> OTHER INFORMATION: primer

<400> SEQUENCE: 161
atgaccacag acctacaaca tgca                                                24

<210> SEQ ID NO 162
<211> LENGTH: 24
<212> TYPE: DNA
<213> ORGANISM: Artificial Sequence
<220> FEATURE:
<223> OTHER INFORMATION: primer

<400> SEQUENCE: 162
cccaggatcc tcgtgtgtgt taca                                                24

<210> SEQ ID NO 163
<211> LENGTH: 23
<212> TYPE: DNA
<213> ORGANISM: Artificial Sequence
<220> FEATURE:
<223> OTHER INFORMATION: primer

<400> SEQUENCE: 163
```

-continued

| | |
|---|---|
| ctgctgtggc atcatggtgc cta | 23 |

<210> SEQ ID NO 164
<211> LENGTH: 24
<212> TYPE: DNA
<213> ORGANISM: Artificial Sequence
<220> FEATURE:
<223> OTHER INFORMATION: primer

<400> SEQUENCE: 164

| | |
|---|---|
| caggagccaa ctgggaaata gact | 24 |

<210> SEQ ID NO 165
<211> LENGTH: 24
<212> TYPE: DNA
<213> ORGANISM: Artificial Sequence
<220> FEATURE:
<223> OTHER INFORMATION: primer

<400> SEQUENCE: 165

| | |
|---|---|
| caccagccaa agaaaacaca tggt | 24 |

<210> SEQ ID NO 166
<211> LENGTH: 24
<212> TYPE: DNA
<213> ORGANISM: Artificial Sequence
<220> FEATURE:
<223> OTHER INFORMATION: primer

<400> SEQUENCE: 166

| | |
|---|---|
| caccagccaa agaaaacaca tggt | 24 |

<210> SEQ ID NO 167
<211> LENGTH: 24
<212> TYPE: DNA
<213> ORGANISM: Artificial Sequence
<220> FEATURE:
<223> OTHER INFORMATION: primer

<400> SEQUENCE: 167

| | |
|---|---|
| caccagccaa agaaaacaca tggt | 24 |

<210> SEQ ID NO 168
<211> LENGTH: 24
<212> TYPE: DNA
<213> ORGANISM: Artificial Sequence
<220> FEATURE:
<223> OTHER INFORMATION: primer

<400> SEQUENCE: 168

| | |
|---|---|
| caccagccaa agaaaacaca tggt | 24 |

<210> SEQ ID NO 169
<211> LENGTH: 23
<212> TYPE: DNA
<213> ORGANISM: Artificial Sequence
<220> FEATURE:
<223> OTHER INFORMATION: primer

<400> SEQUENCE: 169

| | |
|---|---|
| caaggcagcc aaggatgtag gaa | 23 |

<210> SEQ ID NO 170
<211> LENGTH: 24
<212> TYPE: DNA

```
<213> ORGANISM: Artificial Sequence
<220> FEATURE:
<223> OTHER INFORMATION: primer

<400> SEQUENCE: 170
cctgggacta aaccaccaat ccat                                              24

<210> SEQ ID NO 171
<211> LENGTH: 24
<212> TYPE: DNA
<213> ORGANISM: Artificial Sequence
<220> FEATURE:
<223> OTHER INFORMATION: primer

<400> SEQUENCE: 171
agcctggcat ttagaagtca agga                                              24

<210> SEQ ID NO 172
<211> LENGTH: 23
<212> TYPE: DNA
<213> ORGANISM: Mus musculus

<400> SEQUENCE: 172
actggcagtc tcctctgatg tgg                                               23

<210> SEQ ID NO 173
<211> LENGTH: 23
<212> TYPE: DNA
<213> ORGANISM: Mus musculus

<400> SEQUENCE: 173
aaaggcagtc tcctctgaag tgg                                               23

<210> SEQ ID NO 174
<211> LENGTH: 23
<212> TYPE: DNA
<213> ORGANISM: Mus musculus

<400> SEQUENCE: 174
tatggcagtc ttctctgatg ggg                                               23

<210> SEQ ID NO 175
<211> LENGTH: 23
<212> TYPE: DNA
<213> ORGANISM: Mus musculus

<400> SEQUENCE: 175
agaggcagtc tcctctgagg agg                                               23

<210> SEQ ID NO 176
<211> LENGTH: 23
<212> TYPE: DNA
<213> ORGANISM: Mus musculus

<400> SEQUENCE: 176
actagcattc ccctatgatg ggg                                               23

<210> SEQ ID NO 177
<211> LENGTH: 23
<212> TYPE: DNA
<213> ORGANISM: Mus musculus

<400> SEQUENCE: 177
taaagcagtc ttctctgatg ggg                                               23
```

-continued

<210> SEQ ID NO 178
<211> LENGTH: 23
<212> TYPE: DNA
<213> ORGANISM: Mus musculus

<400> SEQUENCE: 178
actggaagcc ttctctgatg agg                                              23

<210> SEQ ID NO 179
<211> LENGTH: 74
<212> TYPE: DNA
<213> ORGANISM: Mus musculus

<400> SEQUENCE: 179
cacctgatat ctcactttgc tgcaggcagg attcccctct ggctcactgg cagtctcctc     60
cgatgtgggc cagg                                                        74

<210> SEQ ID NO 180
<211> LENGTH: 72
<212> TYPE: DNA
<213> ORGANISM: Artificial Sequence
<220> FEATURE:
<223> OTHER INFORMATION: Rpe65 donor template

<400> SEQUENCE: 180
catttgatat ctcactttgc tgcaggcagg attcccctct ggctcactgg cagtctgctc     60
cgttgtgggc ca                                                          72

<210> SEQ ID NO 181
<211> LENGTH: 72
<212> TYPE: DNA
<213> ORGANISM: Mus musculus

<400> SEQUENCE: 181
cacctgatat ctcactttgc tgcaggcagg attcccctct ggctcactgg cagtctcctc     60
cgatgtgggc ca                                                          72

<210> SEQ ID NO 182
<211> LENGTH: 72
<212> TYPE: DNA
<213> ORGANISM: Artificial Sequence
<220> FEATURE:
<223> OTHER INFORMATION: Edited sequence(HDR)

<400> SEQUENCE: 182
cacctgatat ctcactttgc tgcaggcagg attcccctct ggctcactgg cagtctgctc     60
cgttgtgggc ca                                                          72

<210> SEQ ID NO 183
<211> LENGTH: 69
<212> TYPE: DNA
<213> ORGANISM: Artificial Sequence
<220> FEATURE:
<223> OTHER INFORMATION: Edited sequence(1-codon-Del 1)

<400> SEQUENCE: 183
cacctgatat ctcactttgc tgcaggcagg attcccctct ggctcactgg cagtctcctc     60
cgtgggcca                                                              69

<210> SEQ ID NO 184

```
<211> LENGTH: 69
<212> TYPE: DNA
<213> ORGANISM: Artificial Sequence
<220> FEATURE:
<223> OTHER INFORMATION: Edited sequence(1-codon-Del 2)

<400> SEQUENCE: 184
cacctgatat ctcactttgc tgcaggcagg attcccctct ggctcactgg cagtctccta    60
tgtgggcca                                                            69

<210> SEQ ID NO 185
<211> LENGTH: 72
<212> TYPE: DNA
<213> ORGANISM: Artificial Sequence
<220> FEATURE:
<223> OTHER INFORMATION: Mutant sequence of Rpe65 gene in rd12 mouse

<400> SEQUENCE: 185
cacctgatat ctcactttgc tgcaggcagg attcccctct ggctcactgg cagtctcctc    60
tgatgtgggc ca                                                        72

<210> SEQ ID NO 186
<211> LENGTH: 72
<212> TYPE: DNA
<213> ORGANISM: Artificial Sequence
<220> FEATURE:
<223> OTHER INFORMATION: Edited sequence(HDR)

<400> SEQUENCE: 186
cacctgatat ctcactttgc tgcaggcagg attcccctct ggctcactgg cagtctgctc    60
cgttgtgggc ca                                                        72

<210> SEQ ID NO 187
<211> LENGTH: 69
<212> TYPE: DNA
<213> ORGANISM: Artificial Sequence
<220> FEATURE:
<223> OTHER INFORMATION: Edited sequence(1-codon-Del 1)

<400> SEQUENCE: 187
cacctgatat ctcactttgc tgcaggcagg attcccctct ggctcactgg cagtctcctc    60
tgtgggcca                                                            69

<210> SEQ ID NO 188
<211> LENGTH: 69
<212> TYPE: DNA
<213> ORGANISM: Artificial Sequence
<220> FEATURE:
<223> OTHER INFORMATION: Edited sequence(1-codon-Del 2)

<400> SEQUENCE: 188
cacctgatat ctcactttgc tgcaggcagg attcccctct ggctcactgg cagtctccta    60
tgtgggcca                                                            69

<210> SEQ ID NO 189
<211> LENGTH: 8
<212> TYPE: PRT
<213> ORGANISM: Homo sapiens

<400> SEQUENCE: 189

Thr Gly Ser Leu Leu Arg Cys Gly
1               5
```

```
<210> SEQ ID NO 190
<211> LENGTH: 24
<212> TYPE: DNA
<213> ORGANISM: Homo sapiens

<400> SEQUENCE: 190
accggcagtc tccttcgatg tggg                                              24

<210> SEQ ID NO 191
<211> LENGTH: 24
<212> TYPE: DNA
<213> ORGANISM: Mus musculus

<400> SEQUENCE: 191
actggcagtc tcctccgatg tggg                                              24

<210> SEQ ID NO 192
<211> LENGTH: 23
<212> TYPE: DNA
<213> ORGANISM: Mus musculus

<400> SEQUENCE: 192
actggcagtc tcccttgatg gag                                               23

<210> SEQ ID NO 193
<211> LENGTH: 23
<212> TYPE: DNA
<213> ORGANISM: Mus musculus

<400> SEQUENCE: 193
agtggcagtg tcatctgatg ggg                                               23

<210> SEQ ID NO 194
<211> LENGTH: 23
<212> TYPE: DNA
<213> ORGANISM: Mus musculus

<400> SEQUENCE: 194
acttccagcc tcctctgatg gag                                               23

<210> SEQ ID NO 195
<211> LENGTH: 23
<212> TYPE: DNA
<213> ORGANISM: Mus musculus

<400> SEQUENCE: 195
actgtctgtc tcctatgatg aag                                               23

<210> SEQ ID NO 196
<211> LENGTH: 25
<212> TYPE: DNA
<213> ORGANISM: Mus musculus

<400> SEQUENCE: 196
actggcagtc tctcacttga tgtgg                                             25

<210> SEQ ID NO 197
<211> LENGTH: 23
<212> TYPE: DNA
<213> ORGANISM: Mus musculus

<400> SEQUENCE: 197
catggcagtc tcctctgatg gag                                               23
```

<210> SEQ ID NO 198
<211> LENGTH: 23
<212> TYPE: DNA
<213> ORGANISM: Mus musculus

<400> SEQUENCE: 198
ccaggcattc tcctctgatg tgg                                              23

<210> SEQ ID NO 199
<211> LENGTH: 23
<212> TYPE: DNA
<213> ORGANISM: Mus musculus

<400> SEQUENCE: 199
actggctttc tcctctcatg agg                                              23

<210> SEQ ID NO 200
<211> LENGTH: 23
<212> TYPE: DNA
<213> ORGANISM: Mus musculus

<400> SEQUENCE: 200
actggaagac tcctctgaag gag                                              23

<210> SEQ ID NO 201
<211> LENGTH: 23
<212> TYPE: DNA
<213> ORGANISM: Mus musculus

<400> SEQUENCE: 201
accgacagtc tcctctggtg ggg                                              23

<210> SEQ ID NO 202
<211> LENGTH: 23
<212> TYPE: DNA
<213> ORGANISM: Mus musculus

<400> SEQUENCE: 202
cctggcattc tcctctgctg ggg                                              23

<210> SEQ ID NO 203
<211> LENGTH: 23
<212> TYPE: DNA
<213> ORGANISM: Mus musculus

<400> SEQUENCE: 203
cctggcattc tcctctaatg ggg                                              23

<210> SEQ ID NO 204
<211> LENGTH: 23
<212> TYPE: DNA
<213> ORGANISM: Mus musculus

<400> SEQUENCE: 204
cctggctgtc tcctctgaag agg                                              23

<210> SEQ ID NO 205
<211> LENGTH: 23
<212> TYPE: DNA
<213> ORGANISM: Mus musculus

<400> SEQUENCE: 205
actggccatc tcctctgatc agg                                               23

<210> SEQ ID NO 206
<211> LENGTH: 23
<212> TYPE: DNA
<213> ORGANISM: Mus musculus

<400> SEQUENCE: 206
actggcagtc tcaaatgatg tgg                                               23

<210> SEQ ID NO 207
<211> LENGTH: 23
<212> TYPE: DNA
<213> ORGANISM: Mus musculus

<400> SEQUENCE: 207
acttgcagtc tcctctgaac gag                                               23

<210> SEQ ID NO 208
<211> LENGTH: 23
<212> TYPE: DNA
<213> ORGANISM: Mus musculus

<400> SEQUENCE: 208
actggcagtc tcctttgtag ggg                                               23

<210> SEQ ID NO 209
<211> LENGTH: 23
<212> TYPE: DNA
<213> ORGANISM: Mus musculus

<400> SEQUENCE: 209
actggctgtc tgctctgctg tag                                               23

<210> SEQ ID NO 210
<211> LENGTH: 23
<212> TYPE: DNA
<213> ORGANISM: Mus musculus

<400> SEQUENCE: 210
actggcaggc acctctgatt cag                                               23

<210> SEQ ID NO 211
<211> LENGTH: 23
<212> TYPE: DNA
<213> ORGANISM: Mus musculus

<400> SEQUENCE: 211
actgccagtc ttctctgagg tag                                               23

<210> SEQ ID NO 212
<211> LENGTH: 23
<212> TYPE: DNA
<213> ORGANISM: Mus musculus

<400> SEQUENCE: 212
actgccagtc ttctctgagg tag                                               23

<210> SEQ ID NO 213
<211> LENGTH: 23
<212> TYPE: DNA
<213> ORGANISM: Mus musculus

<400> SEQUENCE: 213

```
actgggaatc tcctcagatg aag                                          23

<210> SEQ ID NO 214
<211> LENGTH: 23
<212> TYPE: DNA
<213> ORGANISM: Mus musculus

<400> SEQUENCE: 214
atttgcagtc tcctctgaag tag                                          23

<210> SEQ ID NO 215
<211> LENGTH: 23
<212> TYPE: DNA
<213> ORGANISM: Mus musculus

<400> SEQUENCE: 215
actggcagtc tcttcttatc tgg                                          23

<210> SEQ ID NO 216
<211> LENGTH: 23
<212> TYPE: DNA
<213> ORGANISM: Mus musculus

<400> SEQUENCE: 216
actgtcagtt tcctctcatg gag                                          23

<210> SEQ ID NO 217
<211> LENGTH: 23
<212> TYPE: DNA
<213> ORGANISM: Mus musculus

<400> SEQUENCE: 217
actggcagtc tccttcgttg tag                                          23

<210> SEQ ID NO 218
<211> LENGTH: 23
<212> TYPE: DNA
<213> ORGANISM: Mus musculus

<400> SEQUENCE: 218
cctggcagtc ccctctaatg tgg                                          23

<210> SEQ ID NO 219
<211> LENGTH: 23
<212> TYPE: DNA
<213> ORGANISM: Mus musculus

<400> SEQUENCE: 219
cctggcagtc ccctctaatg tgg                                          23

<210> SEQ ID NO 220
<211> LENGTH: 23
<212> TYPE: DNA
<213> ORGANISM: Mus musculus

<400> SEQUENCE: 220
cctggcagtc ccctctaatg tgg                                          23

<210> SEQ ID NO 221
<211> LENGTH: 23
<212> TYPE: DNA
<213> ORGANISM: Mus musculus
```

-continued

```
<400> SEQUENCE: 221
cctggcagtc ccctctaatg tgg                                              23

<210> SEQ ID NO 222
<211> LENGTH: 23
<212> TYPE: DNA
<213> ORGANISM: Mus musculus

<400> SEQUENCE: 222
actgaaagtc tcctctgagg cag                                              23

<210> SEQ ID NO 223
<211> LENGTH: 23
<212> TYPE: DNA
<213> ORGANISM: Mus musculus

<400> SEQUENCE: 223
actggcattc tcctttaatg ggg                                              23

<210> SEQ ID NO 224
<211> LENGTH: 23
<212> TYPE: DNA
<213> ORGANISM: Mus musculus

<400> SEQUENCE: 224
actggcagtt tcctctgact gag                                              23

<210> SEQ ID NO 225
<211> LENGTH: 12
<212> TYPE: RNA
<213> ORGANISM: Streptococcus pyogenes

<400> SEQUENCE: 225
guuuuagagc ua                                                          12

<210> SEQ ID NO 226
<211> LENGTH: 25
<212> TYPE: RNA
<213> ORGANISM: Campylobacter jejuni

<400> SEQUENCE: 226
guuuuagucc cuuuuaaau uucuu                                             25

<210> SEQ ID NO 227
<211> LENGTH: 9
<212> TYPE: RNA
<213> ORGANISM: Unknown
<220> FEATURE:
<223> OTHER INFORMATION: Parcubacteria bacterium

<400> SEQUENCE: 227 uuuguagau                                                              9

<210> SEQ ID NO 228
<211> LENGTH: 14
<212> TYPE: RNA
<213> ORGANISM: Streptococcus pyogenes

<400> SEQUENCE: 228
uagcaaguua aaau                                                        14

<210> SEQ ID NO 229
<211> LENGTH: 25
```

```
<212> TYPE: RNA
<213> ORGANISM: Campylobacter jejuni

<400> SEQUENCE: 229
aagaaauuua aaaagggacu aaaau                                              25

<210> SEQ ID NO 230
<211> LENGTH: 11
<212> TYPE: RNA
<213> ORGANISM: Unknown
<220> FEATURE:
<223> OTHER INFORMATION: Parcubacteria bacterium

<400> SEQUENCE: 230
aaauuucuac u                                                             11

<210> SEQ ID NO 231
<211> LENGTH: 12
<212> TYPE: RNA
<213> ORGANISM: Streptococcus pyogenes

<400> SEQUENCE: 231
aaggcuaguc cg                                                            12

<210> SEQ ID NO 232
<211> LENGTH: 11
<212> TYPE: RNA
<213> ORGANISM: Campylobacter jejuni

<400> SEQUENCE: 232
aaagaguuug c                                                             11

<210> SEQ ID NO 233
<211> LENGTH: 34
<212> TYPE: RNA
<213> ORGANISM: Streptococcus pyogenes

<400> SEQUENCE: 233
uuaucaacuu gaaaaagugg caccgagucg gugc                                    34

<210> SEQ ID NO 234
<211> LENGTH: 38
<212> TYPE: RNA
<213> ORGANISM: Campylobacter jejuni

<400> SEQUENCE: 234
gggacucugc gggguuacaa uccccuaaaa ccgcuuuu                                38

<210> SEQ ID NO 235
<211> LENGTH: 22
<212> TYPE: RNA
<213> ORGANISM: Streptococcus thermophilus

<400> SEQUENCE: 235
guuuuagagc uguguuguuu cg                                                 22

<210> SEQ ID NO 236
<211> LENGTH: 24
<212> TYPE: RNA
<213> ORGANISM: Streptococcus thermophilus

<400> SEQUENCE: 236
cgaaacaaca cagcgaguua aaau                                               24
```

```
<210> SEQ ID NO 237
<211> LENGTH: 13
<212> TYPE: RNA
<213> ORGANISM: Streptococcus thermophilus

<400> SEQUENCE: 237
aaggcuuagu ccg                                                          13

<210> SEQ ID NO 238
<211> LENGTH: 38
<212> TYPE: RNA
<213> ORGANISM: Streptococcus thermophilus

<400> SEQUENCE: 238
uacucaacuu gaaaaggugg caccgauucg guguuuuu                               38

<210> SEQ ID NO 239
<211> LENGTH: 20
<212> TYPE: DNA
<213> ORGANISM: Artificial Sequence
<220> FEATURE:
<223> OTHER INFORMATION: Target sequence example

<400> SEQUENCE: 239
atcattggca gactagttcg                                                   20

<210> SEQ ID NO 240
<211> LENGTH: 20
<212> TYPE: DNA
<213> ORGANISM: Artificial Sequence
<220> FEATURE:
<223> OTHER INFORMATION: Target sequence example

<400> SEQUENCE: 240
cgaactagtc tgccaatgat                                                   20

<210> SEQ ID NO 241
<211> LENGTH: 7
<212> TYPE: PRT
<213> ORGANISM: Artificial Sequence
<220> FEATURE:
<223> OTHER INFORMATION: Nuclear localization sequence

<400> SEQUENCE: 241

Pro Lys Lys Lys Arg Lys Val
1               5

<210> SEQ ID NO 242
<211> LENGTH: 16
<212> TYPE: PRT
<213> ORGANISM: Artificial Sequence
<220> FEATURE:
<223> OTHER INFORMATION: Nuclear localization sequence

<400> SEQUENCE: 242

Lys Arg Pro Ala Ala Thr Lys Lys Ala Gly Gln Ala Lys Lys Lys Lys
1               5                   10                  15

<210> SEQ ID NO 243
<211> LENGTH: 9
<212> TYPE: PRT
<213> ORGANISM: Artificial Sequence
<220> FEATURE:
<223> OTHER INFORMATION: Nuclear localization sequence

<400> SEQUENCE: 243
```

```
Pro Ala Ala Lys Arg Val Lys Leu Asp
1               5

<210> SEQ ID NO 244
<211> LENGTH: 11
<212> TYPE: PRT
<213> ORGANISM: Artificial Sequence
<220> FEATURE:
<223> OTHER INFORMATION: Nuclear localization sequence

<400> SEQUENCE: 244

Arg Gln Arg Arg Asn Glu Leu Lys Arg Ser Pro
1               5                   10

<210> SEQ ID NO 245
<211> LENGTH: 38
<212> TYPE: PRT
<213> ORGANISM: Artificial Sequence
<220> FEATURE:
<223> OTHER INFORMATION: Nuclear localization sequence

<400> SEQUENCE: 245

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35

<210> SEQ ID NO 246
<211> LENGTH: 42
<212> TYPE: PRT
<213> ORGANISM: Artificial Sequence
<220> FEATURE:
<223> OTHER INFORMATION: Nuclear localization sequence

<400> SEQUENCE: 246

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 247
<211> LENGTH: 8
<212> TYPE: PRT
<213> ORGANISM: Artificial Sequence
<220> FEATURE:
<223> OTHER INFORMATION: Nuclear localization sequence

<400> SEQUENCE: 247

Val Ser Arg Lys Arg Pro Arg Pro
1               5

<210> SEQ ID NO 248
<211> LENGTH: 8
<212> TYPE: PRT
<213> ORGANISM: Artificial Sequence
<220> FEATURE:
<223> OTHER INFORMATION: Nuclear localization sequence

<400> SEQUENCE: 248

Pro Pro Lys Lys Ala Arg Glu Asp
```

```
1               5
```

<210> SEQ ID NO 249
<211> LENGTH: 8
<212> TYPE: PRT
<213> ORGANISM: Artificial Sequence
<220> FEATURE:
<223> OTHER INFORMATION: Nuclear localization sequence

<400> SEQUENCE: 249

```
Pro Gln Pro Lys Lys Lys Pro Leu
1               5
```

<210> SEQ ID NO 250
<211> LENGTH: 12
<212> TYPE: PRT
<213> ORGANISM: Artificial Sequence
<220> FEATURE:
<223> OTHER INFORMATION: Nuclear localization sequence

<400> SEQUENCE: 250

```
Ser Ala Leu Ile Lys Lys Lys Lys Lys Met Ala Pro
1               5                   10
```

<210> SEQ ID NO 251
<211> LENGTH: 5
<212> TYPE: PRT
<213> ORGANISM: Artificial Sequence
<220> FEATURE:
<223> OTHER INFORMATION: Nuclear localization sequence

<400> SEQUENCE: 251

```
Asp Arg Leu Arg Arg
1               5
```

<210> SEQ ID NO 252
<211> LENGTH: 7
<212> TYPE: PRT
<213> ORGANISM: Artificial Sequence
<220> FEATURE:
<223> OTHER INFORMATION: Nuclear localization sequence

<400> SEQUENCE: 252

```
Pro Lys Gln Lys Lys Arg Lys
1               5
```

<210> SEQ ID NO 253
<211> LENGTH: 10
<212> TYPE: PRT
<213> ORGANISM: Artificial Sequence
<220> FEATURE:
<223> OTHER INFORMATION: Nuclear localization sequence

<400> SEQUENCE: 253

```
Arg Lys Leu Lys Lys Lys Ile Lys Lys Leu
1               5                   10
```

<210> SEQ ID NO 254
<211> LENGTH: 10
<212> TYPE: PRT
<213> ORGANISM: Artificial Sequence
<220> FEATURE:
<223> OTHER INFORMATION: Nuclear localization sequence

<400> SEQUENCE: 254

```
Arg Glu Lys Lys Lys Phe Leu Lys Arg Arg
1               5                   10
```

```
<210> SEQ ID NO 255
<211> LENGTH: 20
<212> TYPE: PRT
<213> ORGANISM: Artificial Sequence
<220> FEATURE:
<223> OTHER INFORMATION: Nuclear localization sequence

<400> SEQUENCE: 255

Lys Arg Lys Gly Asp Glu Val Asp Gly Val Asp Glu Val Ala Lys Lys
1               5                   10                  15

Lys Ser Lys Lys
            20

<210> SEQ ID NO 256
<211> LENGTH: 17
<212> TYPE: PRT
<213> ORGANISM: Artificial Sequence
<220> FEATURE:
<223> OTHER INFORMATION: Nuclear localization sequence

<400> SEQUENCE: 256

Arg Lys Cys Leu Gln Ala Gly Met Asn Leu Glu Ala Arg Lys Thr Lys
1               5                   10                  15

Lys
```

GENE MANIPULATION FOR TREATMENT OF RETINAL DYSFUNCTION DISORDER

CROSS-REFERENCE TO RELATED APPLICATIONS

This application is a national phase application of PCT Application No. PCT/KR2018/011522, filed on Sep. 28, 2018, which claims the benefit and priority to U.S. Provisional Patent Application No. 62/565,838, filed Sep. 29, 2017. The entire disclosures of the applications identified in this paragraph are incorporated herein by references.

FIELD

The present invention relates to a composition for gene manipulation for treatment or improvement of a retinal dysfunction disease or a method thereof using the same. More particularly, the present invention relates to a composition for gene manipulation which includes a guide nucleic acid capable of targeting a retinal function-forming gene and a method of treating or improving a disease caused by retinal dysfunction by artificially manipulating and/or correcting the retinal function-forming gene using the composition.

BACKGROUND

There is no suitable therapeutic agent for LCA resulting in blindness in newborns. Since LCA is caused by genetic mutations of over 20 different genes, to resolve this problem, drug development companies (e.g., Spark Therapeutics) have tried to develop therapeutic agents that are used for methods of expressing RPE65, which is one of the causative genes, using AAV, but these agents have a disadvantage of having a therapeutic effect only while AAV is present. Therefore, for longer therapeutic effects, a method of correcting mutations is needed.

SUMMARY

Technical Problem

The present invention is directed to providing a guide nucleic acid targeting a retinal function-forming gene to artificially manipulate the retinal function-forming gene.

The present invention is also directed to providing a composition for gene manipulation for artificially manipulating a retinal function-forming gene.

The present invention is also directed to providing a method of artificially manipulating a retinal function-forming gene.

The present invention is also directed to providing a method of treating a retinal dysfunction disease using the composition for gene manipulation.

Technical Solution

To attain the above-mentioned objects, the present invention relates to a composition for gene manipulation for treatment of a retinal dysfunction disease. More particularly, the present invention relates to a composition for gene manipulation, which may artificially manipulate a retinal function-forming gene to treat a retinal dysfunction disease, and a method thereof using the composition.

The Present Invention Provides a Guide Nucleic Acid Capable of Targeting a Retinal Function-Forming Gene.

In one aspect, the retinal function-forming gene may be a RPE65 gene.

The guide nucleic acid may target a target sequence of the retinal function-forming gene.

Here, the guide nucleic acid may include a guide domain capable of targeting the target sequence of the retinal function-forming gene.

The guide domain may include a nucleotide sequence capable of forming a complementary binding with a guide nucleic acid-binding sequence of target sequence of the retinal function-forming gene.

The guide domain may form a complementary binding with the guide nucleic acid-binding sequence of the target sequence of the retinal function-forming gene.

Here, the complementary binding may include mismatching bindings of 0 to 5.

The guide nucleic acid may include one or more domains selected from the group consisting of a first complementary domain, a linker domain, a second complementary domain, a proximal domain and a tail domain.

The target sequence may include or be located in close proximity to a mutant sequence of the retinal function-forming gene.

Here, the mutant sequence of the retinal function-forming gene may be a partial nucleic acid sequence of the retinal function-forming gene in which one or more nucleotides are deleted, inserted or substituted compared to a nucleic acid sequence of a wild type retinal function-forming gene.

Here, the mutant sequence of the retinal function-forming gene may be a partial nucleic acid sequence of the retinal function-forming gene having one or more different codons compared to a nucleic acid sequence of a wild type retinal function-forming gene.

Here, the mutant sequence of the retinal function-forming gene may be located in one or more regions selected from the group consisting of an exon region and an intron region of the retinal function-forming gene.

Here, the mutant sequence of the retinal function-forming gene may be located in an exon region of the RPE65 gene.

The target sequence may be located in one or more regions selected from the group consisting of a promoter region, an exon region, an intron region and an enhancer region of the retinal function-forming gene.

The target sequence may be a 10 to 25-nt (nucleotide) contiguous sequence located adjacent to 5' end and/or 3' end of a PAM (proto-spacer-adjacent motif) sequence in a nucleic acid sequence of the retinal function-forming gene.

The target sequence may be a 10 to 25-nt contiguous sequence located adjacent to 5' end and/or 3' end of a PAM sequence in a nucleic acid sequence of the retinal function-forming gene including a mutated region.

The target sequence may be one or more sequences selected from a SEQ ID NOs: 1 to 69.

The Present Invention Provides a Composition for Gene Manipulation for Artificially Manipulating a Retinal Function-Forming Gene.

In one aspect, the composition for gene manipulation may comprise the following:
 a guide nucleic acid capable of targeting a target sequence of a retinal function-forming gene, or a nucleic acid sequence encoding the same; and
 one or more editor proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neis-*

*seria meningitidis*-derived Cas9 protein and Cpf1 protein, or a nucleic acid sequence encoding the same.

Here, the retinal function-forming gene may be a RPE65 gene.

The target sequence may include or be located near a mutant sequence of the retinal function-forming gene.

Here, the mutant sequence of the retinal function-forming gene may be a partial nucleic acid sequence of the retinal function-forming gene in which one or more nucleotides are deleted, inserted or substituted compared to a nucleic acid sequence of a wild type retinal function-forming gene.

Alternatively, the mutant sequence of the retinal function-forming gene may be a partial nucleic acid sequence of the retinal function-forming gene having one or more different codons compared to a nucleic acid sequence of a wild type retinal function-forming gene.

Here, the mutant sequence of the retinal function-forming gene may be located in an exon region of the retinal function-forming gene.

The guide nucleic acid and the editor protein may form a guide nucleic acid-editor protein complex.

Here, the guide nucleic acid-editor protein complex may be formed by interacting a partial nucleic acid of the guide nucleic acid with a partial amino acid of the editor protein.

The guide nucleic acid and the editor protein may be present in one or more vectors in a form of a nucleic acid sequence, respectively.

Here, the vector may be a plasmid or a viral vector.

Here, the viral vector may be one or more viral vectors selected from the group consisting of a retrovirus, a lentivirus, an adenovirus, an adeno-associated virus (AAV), a vaccinia virus, a poxvirus and a herpes simplex virus.

In another aspect, the composition for gene manipulation may comprise the following:

a guide nucleic acid capable of targeting a target sequence of a retinal function-forming gene, or a nucleic acid sequence encoding the same;

one or more editor proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and Cpf1 protein, or a nucleic acid sequence encoding the same; and a donor including a nucleic acid to be inserted, or a nucleic acid sequence encoding the same.

Here, the retinal function-forming gene may be a RPE65 gene.

The target sequence may include or be located near a mutant sequence of the retinal function-forming gene.

Here, the mutant sequence of the retinal function-forming gene may be a partial nucleic acid sequence of the retinal function-forming gene in which one or more nucleotides are deleted, inserted or substituted compared to a nucleic acid sequence of a wild type retinal function-forming gene.

Alternatively, the mutant sequence of the retinal function-forming gene may be a partial nucleic acid sequence of the retinal function-forming gene having one or more different codons compared to a nucleic acid sequence of a wild type retinal function-forming gene.

The guide nucleic acid and the editor protein may form a guide nucleic acid-editor protein complex.

Here, the guide nucleic acid-editor protein complex may be formed by interacting a partial nucleic acid of the guide nucleic acid with a partial amino acid of the editor protein.

The nucleic acid to be inserted may be a partial nucleic acid sequence of the retinal function-forming gene.

The nucleic acid to be inserted may be a normal nucleic acid sequence for correcting the mutant sequence of the retinal function-forming gene.

The donor may include nucleotide sequences having homology with respective nucleotide sequences located upstream (left) and/or downstream (right) of a cleaved target sequence.

Here, the nucleotide sequence having homology may be a nucleotide sequence having at least 50% or more homology.

The guide nucleic acid, the editor protein and the donor may be present in one or more vectors in a form of a nucleic acid sequence, respectively.

Here, the vector may be a plasmid or a viral vector.

Here, the viral vector may be one or more viral vectors selected from the group consisting of a retrovirus, a lentivirus, an adenovirus, an adeno-associated virus (AAV), a vaccinia virus, a poxvirus and a herpes simplex virus.

The Present Invention Provides a Method for Treating a Retinal Dysfunction Disease.

In one aspect, the method for treating a retinal dysfunction disease may comprise administration of a composition for gene manipulation into a subject to be treated.

The composition for gene manipulation may comprise the following:

a guide nucleic acid capable of targeting a target sequence of a retinal function-forming gene, or a nucleic acid sequence encoding the same; and one or more editor proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and Cpf1 protein, or a nucleic acid sequence encoding the same.

Here, the retinal function-forming gene may be a RPE65 gene.

The target sequence may include or be located near a mutant sequence of the retinal function-forming gene.

Here, the mutant sequence of the retinal function-forming gene may be a partial nucleic acid sequence of the retinal function-forming gene in which one or more nucleotides are deleted, inserted or substituted compared to a nucleic acid sequence of a wild type retinal function-forming gene.

Alternatively, the mutant sequence of the retinal function-forming gene may be a partial nucleic acid sequence of the retinal function-forming gene having one or more different codons compared to a nucleic acid sequence of a wild type retinal function-forming gene.

Optionally, the composition for gene manipulation may further comprise a donor or a nucleic acid sequence encoding the same.

The retinal dysfunction disease may be Leber congenital amaurosis (LCA), retinal pigmentosa, Stargardt disease, retinal dysplasia, color blindness, choroideremia, macular degeneration, myopic choroidal neovascularization (CNV), polypoidal choroidal vasculopathy (PCV), central serous chorioretinopathy (CSCR), a macular hole, occult macular dystrophy, diabetic retinopathy, a retinal artery/vein occlusion, hypertensive retinopathy, a retinal macroaneurysm, ocular ischemic syndrome, retinopathy of prematurity, acute retinal necrosis, cytomegaloviral retinitis, toxoplasmic retinochoroiditis, syphilitic chorioretinitis, retinal detachment or retinoblastoma.

The retinal dysfunction disease may be Leber congenital amaurosis (LCA) or retinal pigmentosa.

The subject to be treated may be a mammal including a human, a monkey, a mouse and a rat.

The administration may be performed by injection, transfusion, implantation or transplantation.

The administration may be performed via an administration route selected from subretinal, intraocular, intravitreal, intramuscular or intravenous routes.

Advantageous Effects

The present invention can treat a retinal dysfunction disease through a composition for gene manipulation. More particularly, a retinal function disorder can be improved or treated by artificially manipulating and/or correcting a retinal function-forming gene using a composition for gene manipulation, which includes a guide nucleic acid targeting a retinal function-forming gene such that the retinal function-forming gene can normally function or can be normally expressed.

BRIEF DESCRIPTION OF THE DRAWINGS

FIGS. 19A, 19B and 19C shows a graph (a) showing indel frequencies at human RPE65 target sites of a HEK293 cell line and a graph (b) showing percentages of in-frame and out-of-frame indels, in which the frequencies are measured by targeted deep sequencing. The indel frequency at human target site (Ex3-2) corresponding to a TS4 target site is indicated by an arrow.

FIG. 20 shows the comparison of amino acid sequences (SEQ ID NO: 189) between human RPE65 and mouse Rpe65 genes, in which sequences targeted by human (Ex3-2) and mouse (TS4) sgRNA are underlined, and PAM sequences are indicated by square boxes. The nucleic acid sequences of human RPE65 and mouse Rpe65 are SEQ ID NOs: 190 and 191, respectively.

DETAILED DESCRIPTION

Figure 1:
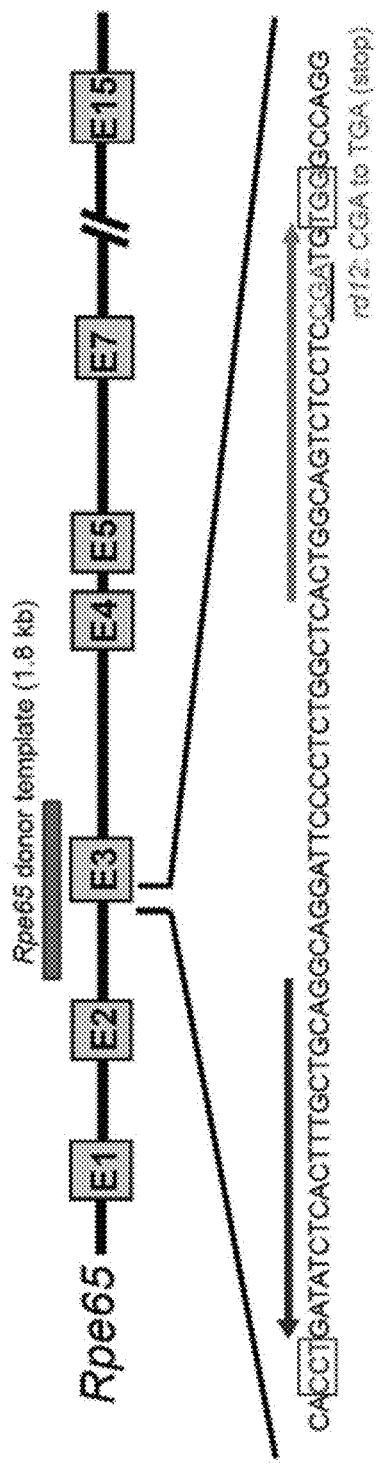
FIG. 1 is a schematic diagram of a wild-type Rpe65 gene, in which a sequence corresponding to the premature termination codon of rd12 mice is underlined in a partial sequence (SEQ ID NO: 179) of the wild-type Rpe65 gene, a TS1 sgRNA target sequence is indicated by a reverse arrow (←), a TS4 sgRNA target sequence is indicated by a forward arrow (→), and a protospacer adjacent motif (PAM) is indicated by a square box.

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limitive.

One Aspect of the Disclosure of the Present Specification Relates to a Guide Nucleic Acid.

The "guide nucleic acid" refers to a nucleotide sequence that recognizes a target nucleic acid, gene or chromosome, and interacts with an editor protein. Here, the guide nucleic acid may complementarily bind to a partial nucleotide sequence in the target nucleic acid, gene or chromosome. In addition, a partial nucleotide sequence of the guide nucleic acid may interact with some amino acids of the editor protein, thereby forming a guide nucleic acid-editor protein complex.

The guide nucleic acid may perform a function to induce a guide nucleic acid-editor protein complex to be located in a target region of a target nucleic acid, gene or chromosome.

The guide nucleic acid may be present in the form of DNA, RNA or a DNA/RNA hybrid, and may have a nucleic acid sequence of 5 to 150 nt.

The guide nucleic acid may have one continuous nucleic acid sequence.

For example, the one continuous nucleic acid sequence may be $(N)_m$, where N represents A, T, C or G, or A, U, C or G, and m is an integer of 1 to 150.

The guide nucleic acid may have two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and m and o may be the same as or different from each other.

The guide nucleic acid may include one or more domains.

The domains may be, but are not limited to, a guide domain, a first complementary domain, a linker domain, a second complementary domain, a proximal domain, or a tail domain.

Here, one guide nucleic acid may have two or more functional domains. Here, the two or more functional domains may be different from each other. For one example, one guide nucleic acid may have a guide domain and a first complementary domain. For another example, one guide nucleic acid may have a second complementary domain, a proximal domain and a tail domain. For still another example, one guide nucleic acid may have a guide domain, a first complementary domain, a second complementary domain, a proximal domain and a tail domain. Alternatively, the two or more functional domains included in one guide nucleic acid may be the same as each other. For one example, one guide nucleic acid may have two or more proximal domains. For another example, one guide nucleic acid may have two or more tail domains. However, the description that the functional domains included in one guide nucleic acid are the same domains does not mean that the sequences of the two functional domains are the same. Even if the sequences are different, the two functional domain can be the same domain when perform functionally the same function.

The functional domain will be described in detail below.

i) Guide Domain

The term "guide domain" is a domain capable of complementary binding with partial sequence of either strand of a double strand of a target gene or a nucleic acid, and acts for specific interaction with a target gene or a nucleic acid. For example, the guide domain may perform a function to induce a guide nucleic acid-editor protein complex to be located to a specific nucleotide sequence of a target gene or a nucleic acid.

The guide domain may be a sequence of 10 to 35 nucleotides.

In an example, the guide domain may be a sequence of 10 to 35, 15 to 35, 20 to 35, 25 to 35 or 30 to 35 nucleotides.

In another example, the guide domain may be a sequence of 10 to 15, 15 to 20, 20 to 25, 25 to 30 or 30 to 35 nucleotides.

The guide domain may have a guide sequence.

The "guide sequence" is a nucleotide sequence complementary to partial sequence of either strand of a double strand of a target gene or a nucleic acid. Here, the guide sequence may be a nucleotide sequence having at least 50%, 55%, 60%, 65%, 70%, 75%, 80%, 85%, 90%, 95% or more complementarity or complete complementarity.

The guide sequence may be a sequence of 10 to 25 nucleotides.

In an example, the guide sequence may be a sequence of 10 to 25, 15 to 25 or 20 to 25 nucleotides.

In another example, the guide sequence may be a sequence of 10 to 15, 15 to 20 or 20 to 25 nucleotides.

In addition, the guide domain may further include an additional nucleotide sequence.

The additional nucleotide sequence may be utilized to improve or degrade the function of the guide domain.

The additional nucleotide sequence may be utilized to improve or degrade the function of the guide sequence.

The additional nucleotide sequence may be a sequence of 1 to 10 nucleotides.

In one example, the additional nucleotide sequence may be a sequence of 2 to 10, 4 to 10, 6 to 10 or 8 to 10 nucleotides.

In another example, the additional nucleotide sequence may be a sequence of 1 to 3, 3 to 6 or 7 to 10 nucleotides.

In one embodiment, the additional nucleotide sequence may be a sequence of 1, 2, 3, 4, 5, 6, 7, 8, 9 or 10 nucleotides.

For example, the additional nucleotide sequence may be one nucleotide sequence G (guanine), or two nucleotide sequence GG.

The additional nucleotide sequence may be located at the 5' end of the guide sequence.

The additional nucleotide sequence may be located at the 3' end of the guide sequence.

ii) First Complementary Domain

The term "first complementary domain" is a domain including a nucleotide sequence complementary to a second complementary domain to be described in below, and has enough complementarity so as to form a double strand with the second complementary domain. For example, the first complementary domain may be a nucleotide sequence having at least 50%, 55%, 60%, 65%, 70%, 75%, 80%, 85%, 90%, 95% or more complementarity or complete complementarity to a second complementary domain.

The first complementary domain may form a double strand with a second complementary domain by a complementary binding. Here, the formed double strand may act to form a guide nucleic acid-editor protein complex by interacting with some amino acids of the editor protein.

The first complementary domain may be a sequence of 5 to 35 nucleotides.

In an example, the first complementary domain may be a sequence of 5 to 35, 10 to 35, 15 to 35, 20 to 35, 25 to 35, or 30 to 35 nucleotides.

In another example, the first complementary domain may be a sequence of 1 to 5, 5 to 10, 10 to 15, 15 to 20, 20 to 25, 25 to 30 or 30 to 35 nucleotides.

iii) Linker Domain

The term "linker domain" is a nucleotide sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a sequence of 1 to 30 nucleotides.

In one example, the linker domain may be a sequence of 1 to 5, 5 to 10, 10 to 15, 15 to 20, 20 to 25, or 25 to 30 nucleotides.

In another example, the linker domain may be a sequence of 1 to 30, 5 to 30, 10 to 30, 15 to 30, 20 to 30, or 25 to 30 nucleotides.

iv) Second Complementary Domain

The term "second complementary domain" is a domain including a nucleotide sequence complementary to the first complementary domain described above, and has enough complementarity so as to form a double strand with the first complementary domain. For example, the second complementary domain may be a nucleotide sequence having at least 50%, 55%, 60%, 65%, 70%, 75%, 80%, 85%, 90%, 95% or more complementarity or complete complementarity to a first complementary domain.

The second complementary domain may form a double strand with a first complementary domain by a complementary binding. Here, the formed double strand may act to form a guide nucleic acid-editor protein complex by interacting with some amino acids of the editor protein. The second complementary domain may have a nucleotide sequence complementary to a first complementary domain, and a nucleotide sequence having no complementarity to the first complementary domain, for example, a nucleotide sequence not forming a double strand with the first complementary domain, and may have a longer base sequence than the first complementary domain.

The second complementary domain may be a sequence of 5 to 35 nucleotides.

In an example, the second complementary domain may be a sequence of 5 to 35, 10 to 35, 15 to 35, 20 to 35, 25 to 35, or 30 to 35 nucleotides.

In another example, the second complementary domain may be a sequence of 1 to 5, 5 to 10, 10 to 15, 15 to 20, 20 to 25, 25 to 30 or 30 to 35 nucleotides.

v) Proximal Domain

The term "proximal domain" is a nucleotide sequence located adjacent to a second complementary domain.

The proximal domain may have a complementary nucleotide sequence therein, and may be formed in a double strand due to a complementary nucleotide sequence.

The proximal domain may be a sequence of 1 to 20 nucleotides.

In one example, the proximal domain may be a sequence of 1 to 20, 5 to 20, 10 to 20 or 15 to 20 nucleotide.

In another example, the proximal domain may be a sequence of 1 to 5, 5 to 10, 10 to 15 or 15 to 20 nucleotides.

vi) Tail Domain

The term "tail domain" is a nucleotide sequence located at one or more ends of the both ends of the guide nucleic acid.

The tail domain may have a complementary nucleotide sequence therein, and may be formed in a double strand due to a complementary nucleotide sequence.

The tail domain may be a sequence of 1 to 50 nucleotides.

In an example, the tail domain may be a sequence of 5 to 50, 10 to 50, 15 to 50, 20 to 50, 25 to 50, 30 to 50, 35 to 50, 40 to 50, or 45 to 50 nucleotides.

In another example, the tail domain may be a sequence of 1 to 5, 5 to 10, 10 to 15, 15 to 20, 20 to 25, 25 to 30, 30 to 35, 35 to 40, 40 to 45, or 45 to 50 nucleotides.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

The guide nucleic acid includes one or more domains.
The guide nucleic acid may include a guide domain.
The guide nucleic acid may include a first complementary domain.
The guide nucleic acid may include a linker domain.
The guide nucleic acid may include a second complementary domain.
The guide nucleic acid may include a proximal domain.
The guide nucleic acid may include a tail domain.
Here, there may be 1, 2, 3, 4, 5, 6 or more domains.
The guide nucleic acid may include 1, 2, 3, 4, 5, 6 or more guide domains.
The guide nucleic acid may include 1, 2, 3, 4, 5, 6 or more first complementary domains.
The guide nucleic acid may include 1, 2, 3, 4, 5, 6 or more linker domains.
The guide nucleic acid may include 1, 2, 3, 4, 5, 6 or more second complementary domains.
The guide nucleic acid may include 1, 2, 3, 4, 5, 6 or more proximal domains.
The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

In One Embodiment of the Disclosure of the Present Specification, the Guide Nucleic Acid May be a gRNA.

gRNA

The "gRNA" refers to a RNA capable of specifically targeting a gRNA-CRISPR enzyme complex, that is, a CRISPR complex, with respect to a target gene or a nucleic acid. In addition, the gRNA is a RNA specific to the nucleic acid in the transcriptional regulatory region of the target gene, which may bind to a CRISPR enzyme and guide the CRISPR enzyme to the target gene or the nucleic acid.

The gRNA may include multiple domains. Due to each domain, interactions may occur in a three-dimensional structure or active form of a gRNA strand, or between these strands.

The gRNA may be called single-stranded gRNA (single RNA molecule, single gRNA or sgRNA); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or a nucleic acid; a first complementary domain; a linker domain; a second complementary domain, which is a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or a nucleic acid and a first complementary domain; and a second strand which includes a second complementary domain, which is a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a nucleic acid in a transcriptional regulatory region of a target gene; a first complementary domain; a second complementary domain, and a domain having a sequence complementary to the first complementary domain sequence, thereby forming a double-stranded nucleic acid with the first complementary domain in the 5' to 3' direction.

Here, the first complementary domain may have homology with a natural first complementary domain, or may be derived from a natural first complementary domain. In addition, the first complementary domain may have a difference in the nucleotide sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Staphylococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' (SEQ ID NO: 225) or a nucleotide sequence having partial, that is, at least 50% or more, or complete homology with 5'-GUUUUAGAGCUA-3' (SEQ ID NO: 225). Here, the first complementary domain may further include $(X)_n$, resulting in 5'-GUUUUAGAGCUA$(X)_n$-3' (SEQ ID NO: 225). The X may be selected from the group consisting of bases A, T, U and G, and the n may represent the number of nucleotides, which is an integer of 5 to 15. Here, the $(X)_n$ may be n repeats of the same nucleotide, or a mixture of n nucleotides of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3' (SEQ ID NO: 226), or a nucleotide sequence having partial, that is, at least 50% or more, or complete homology with 5'-GUUUUAGUCCCUUUUUAAAUUUCUU-3' (SEQ ID NO: 226). Here, the first complementary domain may further include $(X)_n$, resulting in 5'-GUUUUAGUCCCUUUUUAAAUUUCUU$(X)_n$-3' (SEQ ID NO: 226). The X may be selected from the group consisting of nucleotides A, T, U and G, and the n may represent the number of nucleotides, which is an integer of 5 to 15. Here, the $(X)_n$ may represent n repeats of the same nucleotide, or a mixture of n nucleotides of A, T, U and G.

In another embodiment, the first complementary domain may have partial, that is, at least 50% or more, or complete homology with a first complementary domain of *Parcubacteria bacterium* (GWC2011_GWC2_44_17), *Lachnospiraceae bacterium* (MC2017), *Butyrivibrio proteoclasiicus, Peregrinibacteria bacterium* (GW2011_GWA_33_10), *Acidaminococcus* sp. (BV3L6), *Porphyromonas macacae, Lachnospiraceae bacterium* (ND2006), *Porphyromonas crevioricanis, Prevotella disiens, Moraxella bovoculi* (237), *Smiihella* sp. (SC_KO8D17), *Leptospira inadai, Lachnospiraceae bacterium* (MA2020), *Francisella novicida* (U112), *Candidatus Methanoplasma termitum* or *Eubacterium eligens*, or a first complementary domain derived therefrom.

For example, when the first complementary domain is the first complementary domain of *Parcubacteria bacterium* or a first complementary domain derived therefrom, the first complementary domain may be 5'-UUUGUAGAU-3' (SEQ ID NO: 227), or a nucleotide sequence having partial, that is, at least 50% or more homology with 5'-UUUGUAGAU-3' (SEQ ID NO: 227). Here, the first complementary domain may further include $(X)_n$, resulting in 5'-$(X)_n$UUUGUAGAU-3' (SEQ ID NO: 227). The X may be selected from the group consisting of nucleotides A, T, U and G, and the n may represent the number of nucleotides, which is an integer of 1 to 5. Here, the $(X)_n$ may represent n repeats of the same nucleotide, or a mixture of n nucleotides of A, T, U and G.

Here, the linker domain may be a nucleotide sequence connecting a first complementary domain with a second complementary domain.

The linker domain may form a covalent or non-covalent bonding with a first complementary domain and a second complementary domain, respectively.

The linker domain may connect the first complementary domain with the second complementary domain covalently or non-covalently.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding.

The linker domain may be used to produce single-stranded gRNA by being connected with crRNA and tracrRNA of double-stranded gRNA or connecting the crRNA with the tracrRNA by covalent or non-covalent bonding.

Here, the second complementary domain may have homology with a natural second complementary domain, or may be derived from the natural second complementary domain. In addition, the second complementary domain may have a difference in nucleotide sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes, Campylobacter jejuni, Streptococcus thermophilus, Staphylococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3' (SEQ ID NO: 228), or a nucleotide sequence having partial, that is, at least 50% or more homology with 5'-UAGCAAGUUAAAAU-3' (SEQ ID NO: 228) (a nucleotide sequence forming a double strand with the first complementary domain is underlined). Here, the second complementary domain may further include $(X)_n$ and/or $(X)_m$, resulting in 5'-$(X)_n$ UAGCAAGUUAAAAU$(X)_m$-3' (SEQ ID NO: 228). The X may be selected from the group consisting of nucleotides A, T, U and G, and each of the n and m may represent the number of nucleotides, in which the n may be an integer of 1 to 15, and the m may be an integer of 1 to 6. Here, the $(X)_n$ may represent n repeats of the same nucleotide, or a mixture of n nucleotides of A, T, U and G. In addition, $(X)_m$ may represent m repeats of the same nucleotide, or a mixture of m nucleotides of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3' (SEQ ID NO: 229), or a nucleotide sequence having partial, that is, at least 50% or more homology with 5'-AAGAAAUUUAAAAAGGGACUAAAAU-3' (SEQ ID NO: 229) (a nucleotide sequence forming a double strand with the first complementary domain is underlined). Here, the second complementary domain may further include $(X)_n$ and/or $(X)_m$, resulting in 5'-$(X)_n$AAGAAAUUUAAAAAGGGACUAAAAU$(X)_m$-3' (SEQ ID NO: 229). The X may be selected from the group consisting of nucleotides A, T, U and G, and each of the n and m may represent the number of nucleotides, in which the n may be an integer of 1 to 15, and the m may be an integer of 1 to 6. Here, $(X)_n$ may represent n repeats of the same nucleotide, or a mixture of n nucleotides of A, T, U and G. In addition, $(X)_m$ may represent m repeats of the same nucleotide, or a mixture of m nucleotides of A, T, U and G.

In another embodiment, the second complementary domain may have partial, that is, at least 50% or more, or complete homology with a second complementary domain of *Parcubacteria bacterium* (GWC2011_GWC2_44_17), *Lachnospiraceae bacterium* (MC2017), *Butyrivibrio proteoclasiicus*, *Peregrinibacteria bacterium* (GW2011_GWA_33_10), *Acidaminococcus* sp. (BV3L6), *Porphyromonas macacae*, *Lachnospiraceae bacterium* (ND2006), *Porphyromonas crevioricanis*, *Prevotella disiens*, *Moraxella bovoculi* (237), *Smiihella* sp. (SC_KO8D17), *Leptospira inadai*, *Lachnospiraceae bacterium* (MA2020), *Francisella novicida* (U112), *Candidatus Methanoplasma termitum* or *Eubacterium eligens*, or a second complementary domain derived therefrom.

For example, when the second complementary domain is a second complementary domain of *Parcubacteria bacterium* or a second complementary domain derived therefrom, the second complementary domain may be 5'-AAAUUUC-UACU-3' (SEQ ID NO: 230), or a nucleotide sequence having partial, that is, at least 50% or more homology with 5'-AAAUUUCUACU-3' (SEQ ID NO: 230) (a nucleotide sequence forming a double strand with the first complementary domain is underlined). Here, the second complementary domain may further include $(X)_n$ and/or $(X)_m$, resulting in 5'-$(X)_n$AAAUUUCUACU$(X)_m$-3' (SEQ ID NO: 230). The X may be selected from the group consisting of nucleotides A, T, U and G, and each of the n and m may represent the number of nucleotides, in which the n may be an integer of 1 to 10, and the m may be an integer of 1 to 6. Here, the $(X)_n$ may represent n repeats of the same nucleotide, or a mixture of n nucleotides of A, T, U and G. In addition, the $(X)_m$ may represent m repeats of the same nucleotide, or a mixture of m nucleotides of A, T, U and G.

Here, the first complementary domain and the second complementary domain may complementarily bind to each other.

The first complementary domain and the second complementary domain may form a double strand by the complementary binding.

The formed double strand may interact with a CRISPR enzyme.

Optionally, the first complementary domain may include an additional nucleotide sequence that does not complementarily bind to a second complementary domain of a second strand.

Here, the additional nucleotide sequence may be a sequence of 1 to 15 nucleotides. For example, the additional nucleotide sequence may be a sequence of 1 to 5, 5 to 10 or 10 to 15 nucleotides.

Here, the proximal domain may be a domain located at the 3'end direction of the second complementary domain.

The proximal domain may have homology with a natural proximal domain, or may be derived from the natural proximal domain. In addition, the proximal domain may have a difference in nucleotide sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes*, *Campylobacter jejuni*, *Streptococcus thermophilus*, *Staphylococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGC-UAGUCCG-3' (SEQ ID NO: 231), or a nucleotide sequence having partial, that is, at least 50% or more homology with 5'-AAGGCUAGUCCG-3' (SEQ ID NO: 231). Here, the proximal domain may further include $(X)_n$, resulting in 5'-AAGGCUAGUCCG$(X)_n$-3' (SEQ ID NO: 231). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 232), or a nucleotide sequence having at least 50% or more homology with 5'-AAAGAGUUUGC-3' (SEQ ID NO: 232). Here, the proximal domain may further include $(X)_n$, resulting in 5'-AAAGAGUUUGC$(X)_n$-3' (SEQ ID NO: 232). The X may be selected from the group consisting of nucleotides A, T, U and G, and the n may represent the number of nucleotides, which is an integer of 1 to 40. Here, the $(X)_n$ may represent n repeats of the same nucleotide, or a mixture of n nucleotides of A, T, U and G.

Here, the tail domain is a domain which is able to be selectively added to the 3' end of single-stranded gRNA or the first or second strand of double-stranded gRNA.

The tail domain may have homology with a natural tail domain, or may be derived from the natural tail domain. In addition, the tail domain may have a difference in nucleotide sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes*, *Campylobacter jejuni*, *Streptococcus thermophilus*, *Staphylococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 233), or a nucleotide sequence having partial, that is, at least 50% or more homology with 5'-UUAUCAAC-UUGAAAAAGUGGCACCGAGUCGGUGC-3' (SEQ ID NO: 233). Here, the tail domain may further include $(X)_n$, resulting in 5'-UUAUCAAC-UUGAAAAAGUGGCACCGAGUCGGUGC$(X)_n$-3' (SEQ ID NO: 233). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 234), or a nucleotide sequence having partial, that is, at least 50% or more homology with 5'-GGGACUCUGCGGGGUUA-CAAUCCCCUAAAACCGCUUUU-3' (SEQ ID NO: 234). Here, the tail domain may further include $(X)_n$, resulting in 5'-GGGACUCUGCGGGGUUACAAUCCCC-UAAAACCGCUUUU$(X)_n$-3' (SEQ ID NO: 234). The X may be selected from the group consisting of nucleotides A, T, U and G, and the n may represent the number of nucleotides, which is an integer of 1 to 15. Here, the $(X)_n$ may represent n repeats of the same nucleotide, or a mixture of n nucleotides of A, T, U and G.

In another embodiment, the tail domain may include a 1 to 10-nt sequence at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of

5'-[guide domain]-[first complementary domain]-3', and the second strand may consist of 5'-[second complementary domain]-[proximal domain]-3' or 5'-[second complementary domain]-[proximal domain]-[tail domain]-3'.

Here, the first strand may be referred to as crRNA, and the second strand may be referred to as tracrRNA.

Here, the first strand and the second strand may optionally include an additional nucleotide sequence.

In one example, the first strand may be

5'-$(N_{target})$-$(Q)_m$-3'; or

5-$(X)_a$-$(N_{target})$-$(X)_b$-$(Q)_m$-$(X)_c$-3'.

Here, the $N_{target}$ is a nucleotide sequence complementary to partial sequence of either strand of a double strand of a target gene or a nucleic acid, and a nucleotide sequence region which may be changed according to a target sequence on a target gene or a nucleic acid.

Here, the $(Q)_m$ is a nucleotide sequence including a first complementary domain, which is able to form a complementary bond with the second complementary domain of the second strand. The $(Q)_m$ may be a sequence having partial or complete homology with the first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Streptococcus pyogenes* or a *Streptococcus pyogenes*-derived first complementary domain, the $(Q)_m$ may be 5'-GUUUUAGAGCUA-3' (SEQ ID NO: 225), or a nucleotide sequence having at least 50% or more homology with 5'-GUUUUAGAGCUA-3' (SEQ ID NO: 225).

In another example, when the first complementary domain has partial or complete homology with a first complementary domain of *Campylobacter jejuni* or a *Campylobacter jejuni*-derived first complementary domain, the $(Q)_m$ may be 5'-GUUUUAGUCCC-UUUUUAAAUUUCUU-3' (SEQ ID NO: 226), or a nucleotide sequence having at least 50% or more homology with 5'-GUUUUAGUCCCUUUUUAAAUUUCUU-3' (SEQ ID NO: 226).

In still another example, when the first complementary domain has partial or complete homology with a first complementary domain of *Streptococcus thermophilus* or a *Streptococcus thermophilus*-derived first complementary domain, the $(Q)_m$ may be 5'-GUUUUAGAGCUGUGUU-GUUUCG-3' (SEQ ID NO: 235), or a nucleotide sequence having at least 50% or more homology with 5'-GUUUUA-GAGCUGUGUUGUUUCG-3' (SEQ ID NO: 235).

In addition, each of the $(X)_a$, $(X)_b$ and $(X)_c$ is selectively an additional nucleotide sequence, where the X may be each independently selected from the group consisting of A, U, C and G, and each of the a, b and c may be the number of nucleotides, which is 0 or an integer of 1 to 20.

In one exemplary embodiment, the second strand may be

5'-$(Z)_h$-$(P)_k$-3'; or 5'-$(X)_d$-$(Z)_h$-$(X)_e$-$(P)_k$-$(X)_f$-3'.

In another embodiment, the second strand may be

5'-$(Z)_h$-$(P)_k$-$(F)_i$-3'; or 5'-$(X)_d$-$(Z)_h$-$(X)_e$-$(P)_k$-$(X)_f$-$(F)_i$-3'.

Here, the $(Z)_h$ is a nucleotide sequence including a second complementary domain, which is able to form a complementary bond with the first complementary domain of the first strand. The $(Z)_h$ may be a sequence having partial or complete homology with the second complementary domain of a species existing in nature, and the nucleotide sequence of the second complementary domain may be modified according to the species of origin. The Z may be each independently selected from the group consisting of A, U, C and G, and the h may be the number of nucleotides, which is an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3' (SEQ ID NO: 228), or a nucleotide sequence having at least 50% or more homology with 5'-UAGCAAGUUAAAAU-3' (SEQ ID NO: 228).

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3' (SEQ ID NO: 229), or a nucleotide sequence having at least 50% or more homology with 5'-AAGAAAUUUAAAAAGGGAC-UAAAAU-3' (SEQ ID NO: 229).

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3' (SEQ ID NO: 236), or a nucleotide sequence having at least 50% or more homology with 5'-CGAAACAACACAGCGAGUUAAAAU-3' (SEQ ID NO: 236).

The $(P)_k$ is a nucleotide sequence including a proximal domain, which may have partial or complete homology with a proximal domain of a species existing in nature, and the nucleotide sequence of the proximal domain may be modified according to the species of origin. The P may be each independently selected from the group consisting of A, U, C and G, and the k may be the number of nucleotides, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3' (SEQ ID NO: 231), or a nucleotide sequence having at least 50% or more homology with 5'-AAGGCUAGUCCG-3' (SEQ ID NO: 231).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 232), or a nucleotide sequence having at least 50% or more homology with 5'-AAAGAGUUUGC-3' (SEQ ID NO: 232).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 237), or a nucleotide sequence having at least 50% or more homology with 5'-AAGGCUUAGUCCG-3' (SEQ ID NO: 237).

The $(F)_i$ may be a nucleotide sequence including a tail domain, and having partial or complete homology with a tail domain of a species existing in nature, and the nucleotide sequence of the tail domain may be modified according to the species of origin. The F may be each independently selected from the group consisting of A, U, C and G, and the i may be the number of nucleotides, which is an integer of 1 to 50.

For example, when the tail domain has partial or complete homology with a tail domain of *Streptococcus pyogenes* or a tail domain derived therefrom, the $(F)_i$ may be 5'-UUAUCAACUUGAAAAAGUGGCACCGAGUCGGUGC-3' (SEQ ID NO: 233), or a nucleotide sequence having at least 50% or more homology with 5'-UUAUCAACUUGAAAAAGUGGCACCGAGUCGGUGC-3' (SEQ ID NO: 233).

In another example, when the tail domain has partial or complete homology with a tail domain of *Campylobacter jejuni* or a tail domain derived therefrom, the $(F)_i$ may be 5'-GGGACUCUGCGGGGUUACAAUCCCUAAAACCGCUUUU-3' (SEQ ID NO: 234), or a nucleotide sequence having at least 50% or more homology with 5'-GGGACUCUGCGGGGUUACAAUCCCUAAAACCGCUUUU-3' (SEQ ID NO: 234).

In still another example, when the tail domain has partial or complete homology with a tail domain of *Streptococcus thermophilus* or a tail domain derived therefrom, the $(F)_i$ may be 5'-UACUCAACUUGAAAAG-GUGGCACCGAUUCGGUGUUUUU-3' (SEQ ID NO: 238), or a nucleotide sequence having at least 50% or more homology with 5'-UACUCAACUUGAAAAG-GUGGCACCGAUUCGGUGUUUUU-3' (SEQ ID NO: 238).

In addition, the $(F)_i$ may include a sequence of 1 to 10 nucleotides at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

In addition, the $(X)_d$, $(X)_e$ and $(X)_f$ may be nucleotide sequences selectively added, where the X may be each independently selected from the group consisting of A, U, C and G, and each of the d, e and f may be the number of nucleotides, which is 0 or an integer of 1 to 20.

Single-Stranded gRNA

Single-stranded gRNA may be classified into a first single-stranded gRNA and a second single-stranded gRNA.

First Single-Stranded gRNA

First single-stranded gRNA is single-stranded gRNA in which a first strand or a second strand of the double-stranded gRNA is linked by a linker domain.

Specifically, the single-stranded gRNA may consist of
5'-[guide domain]-[first complementary domain]-[linker domain]-[second complementary domain]-3',
5'-[guide domain]-[first complementary domain]-[linker domain]-[second complementary domain]-[proximal domain]-3' or
5'-[guide domain]-[first complementary domain]-[linker domain]-[second complementary domain]-[proximal domain]-[tail domain]-3'.

The first single-stranded gRNA may selectively include an additional nucleotide sequence.

In one exemplary embodiment, the first single-stranded gRNA may be
5'-$(N_{target})$-$(Q)_m$-$(L)_j$-$(Z)_h$-3';
5'-$(N_{target})$-$(Q)_m$-$(L)_j$-$(Z)_h$-$(P)_k$-3'; or
5'-$(N_{target})$-$(Q)_m$-$(L)_j$-$(Z)_h$-$(P)_k$-$(F)_i$-3'.

In another embodiment, the single-stranded gRNA may be
5'-$(X)_a$-$(N_{target})$-$(X)_b$-$(Q)_m$-$(X)_c$-$(L)_j$-$(X)_d$-$(Z)_h$-$(X)_e$-3';
5'-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-3'; or
5'-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-$(F)_i$-3'.

Here, the $N_{target}$ is a nucleotide sequence complementary to partial sequence of either strand of a double strand of a target gene or a nucleic acid, and a nucleotide sequence region capable of being changed according to a target sequence on a target gene or a nucleic acid.

The $(Q)_m$ includes a nucleotide sequence including the first complementary domain, which is able to form a complementary bond with a second complementary domain. The $(Q)_m$ may be a sequence having partial or complete homology with a first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Streptococcus pyogenes* or a first complementary domain derived therefrom, the $(Q)_m$ may be 5'-GUUUUA-GAGCUA-3' (SEQ ID NO: 225), or a nucleotide sequence having at least 50% or more homology with 5'-GUUUUA-GAGCUA-3' (SEQ ID NO: 225).

In another example, when the first complementary domain has partial or complete homology with a first complementary domain of *Campylobacter jejuni* or a first complementary domain derived therefrom, the $(Q)_m$ may be 5'-GUUUUAGUCCCUUUUUAAAUUUCUU-3' (SEQ ID NO: 226), or a nucleotide sequence having at least 50% or more homology with 5'-GUUUUAGUCCC-UUUUUAAAUUUCUU-3' (SEQ ID NO: 226).

In still another example, when the first complementary domain has partial or complete homology with a first complementary domain of *Streptococcus thermophilus* or a first complementary domain derived therefrom, the $(Q)_m$ may be 5'-GUUUUAGAGCUGUGUUGUUUCG-3' (SEQ ID NO: 235), or a nucleotide sequence having at least 50% or more homology with 5'-GUUUUAGAGCUGUGUU-GUUUCG-3' (SEQ ID NO: 235).

In addition, the $(L)_j$ is a nucleotide sequence including the linker domain, and connecting the first complementary domain with the second complementary domain, thereby producing single-stranded gRNA. Here, the L may be each independently selected from the group consisting of A, U, C and G, and the j may be the number of nucleotides, which is an integer of 1 to 30.

The $(Z)_h$ is a nucleotide sequence including the second complementary domain, and includes a nucleotide sequence capable of complementary binding with the first complementary domain. The $(Z)_h$ may be a sequence having partial or complete homology with the second complementary domain of a species existing in nature, and the nucleotide sequence of the second complementary domain may be changed according to the species of origin. The Z may be each independently selected from the group consisting of A, U, C and G, and the h is the number of nucleotides, which may be an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3' (SEQ ID NO: 228), or a nucleotide sequence having at least 50% or more homology with 5'-UAGCAAGUUAAAAU-3' (SEQ ID NO: 228).

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3' (SEQ ID NO: 229), or a nucleotide sequence having at least 50% or more homology with 5'-AAGAAAUUUAAAAAGGGAC-UAAAAU-3' (SEQ ID NO: 229).

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3' (SEQ ID NO: 236), or a nucleotide sequence having at least 50% or more homology with 5'-CGAAACAACACAGCGAGUUAAAAU-3' (SEQ ID NO: 236).

The $(P)_k$ is a nucleotide sequence including a proximal domain, which may have partial or complete homology with a proximal domain of a species existing in nature, and the nucleotide sequence of the proximal domain may be modified according to the species of origin. The P may be each independently selected from the group consisting of A, U, C and G, and the k may be the number of nucleotides, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3' (SEQ ID NO: 231), or a nucleotide sequence having at least 50% or more homology with 5'-AAGGCUAGUCCG-3' (SEQ ID NO: 231).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 232), or a nucleotide sequence having at least 50% or more homology with 5'-AAAGAGUUUGC-3' (SEQ ID NO: 232).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 237), or a nucleotide sequence having at least 50% or more homology with 5'-AAGGCUUAGUCCG-3' (SEQ ID NO: 237).

The $(F)_i$ may be a nucleotide sequence including a tail domain, and having partial or complete homology with a tail domain of a species existing in nature, and the nucleotide sequence of the tail domain may be modified according to the species of origin. The F may be each independently selected from the group consisting of A, U, C and G, and the i may be the number of nucleotides, which is an integer of 1 to 50.

For example, when the tail domain has partial or complete homology with a tail domain of *Streptococcus pyogenes* or a tail domain derived therefrom, the $(F)_i$ may be 5'-UUAU-CAACUUGAAAAAGUGGCACCGAGUCGGUGC-3' (SEQ ID NO: 233), or a nucleotide sequence having at least 50% or more homology with 5'-UUAUCAAC-UUGAAAAAGUGGCACCGAGUCGGUGC-3' (SEQ ID NO: 233).

In another example, when the tail domain has partial or complete homology with a tail domain of *Campylobacter jejuni* or a tail domain derived therefrom, the $(F)_i$ may be 5'-GGGACUCUGCGGGGUUACAAUCCCC-UAAAACCGCUUUU-3' (SEQ ID NO: 234), or a nucleotide sequence having at least 50% or more homology with 5'-GGGACUCUGCGGGGUUACAAUCCCC-UAAAACCGCUUUU-3' (SEQ ID NO: 234).

In still another example, when the tail domain has partial or complete homology with a tail domain of *Streptococcus thermophilus* or a tail domain derived therefrom, the $(F)_i$ may be 5'-UACUCAACUUGAAAAG-GUGGCACCGAUUCGGUGUUUU-3' (SEQ ID NO: 238), or a nucleotide sequence having at least 50% or more homology with 5'-UACUCAACUUGAAAAG-GUGGCACCGAUUCGGUGUUUU-3' (SEQ ID NO: 238).

In addition, the $(F)_i$ may include a sequence of 1 to 10 nucleotides at the 3' end involved in an in vitro or in vivo transcription method.

For example, when a T7 promoter is used in in vitro transcription of gRNA, the tail domain may be an arbitrary nucleotide sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil nucleotides or alternative nucleotides.

In addition, the $(X)_a$, $(X)_b$, $(X)_c$, $(X)_d$, $(X)_e$ and $(X)_f$ may be nucleotide sequences selectively added, where the X may be each independently selected from the group consisting of A, U, C and G, and each of the a, b, c, d, e and f may be the number of nucleotides, which is 0 or an integer of 1 to 20.

Second Single-Stranded gRNA

Second single-stranded gRNA may be single-stranded gRNA consisting of a guide domain, a first complementary domain and a second complementary domain.

Here, the second single-stranded gRNA may consist of:
5'-[second complementary domain]-[first complementary domain]-[guide domain]-3'; or
5'-[second complementary domain]-[linker domain]-[first complementary domain]-[guide domain]-3'.

The second single-stranded gRNA may selectively include an additional nucleotide sequence.

In one exemplary embodiment, the second single-stranded gRNA may be
5'-$(Z)_h$-$(Q)_m$-$(N_{target})$-3'; or
5'-$(X)_a$-$(Z)_h$-$(X)_b$-$(Q)_m$-$(X)_c$-$(N_{target})$-3'.

In another embodiment, the single-stranded gRNA may be
5'-$(Z)_h$-$(L)_j$-$(Q)_m$-$(N_{target})$-3'; or
5'-$(X)_a$-$(Z)_h$-$(L)_j$-$(Q)_m$-$(X)_c$-$(N_{target})$-3'.

Here, the $N_{target}$ is a nucleotide sequence complementary to partial sequence of either strand of a double strand of a target gene or a nucleic acid, and a nucleotide sequence region capable of being changed according to a target sequence on a target gene or a nucleic acid.

The $(Q)_m$ is a nucleotide sequence including the first complementary domain, and includes a nucleotide sequence capable of complementary binding with a second complementary domain. The $(Q)_m$ may be a sequence having partial or complete homology with the first complementary domain of a species existing in nature, and the nucleotide sequence of the first complementary domain may be changed according to the species of origin. The Q may be each independently selected from the group consisting of A, U, C and G, and the m may be the number of nucleotides, which is an integer of 5 to 35.

For example, when the first complementary domain has partial or complete homology with a first complementary domain of *Parcubacteria bacterium* or a first complementary domain derived therefrom, the $(Q)_m$ may be 5'-UUUGUAGAU-3' (SEQ ID NO: 227), or a nucleotide sequence having at least 50% or more homology with 5'-UUUGUAGAU-3' (SEQ ID NO: 227).

The $(Z)_h$ is a nucleotide sequence including a second complementary domain, and includes a nucleotide sequence capable of complementary binding with a second complementary domain. The $(Z)_h$ may be a sequence having partial or complete homology with the second complementary domain of a species existing in nature, and the nucleotide sequence of the second complementary domain may be modified according to the species of origin. The Z may be each independently selected from the group consisting of A, U, C and G, and the h may be the number of nucleotides, which is an integer of 5 to 50.

For example, when the second complementary domain has partial or complete homology with a second complementary domain of *Parcubacteria bacterium* or a *Parcubacteria bacterium*-derived second complementary domain, the $(Z)_h$ may be 5'-AAAUUUCUACU-3' (SEQ ID NO: 230), or a nucleotide sequence having at least 50% or more homology with 5'-AAAUUUCUACU-3' (SEQ ID NO: 230).

In addition, the $(L)_j$ is a nucleotide sequence including the linker domain, which connects the first complementary domain with the second complementary domain. Here, the L may be each independently selected from the group consisting of A, U, C and G, and the j may be the number of nucleotides, which is an integer of 1 to 30.

In addition, each of the $(X)_a$, $(X)_b$ and $(X)_c$ is selectively an additional nucleotide sequence, where the X may be each independently selected from the group consisting of A, U, C and G, and the a, b and c may be the number of nucleotides, which is 0 or an integer of 1 to 20.

As one aspect of the disclosure in the present specification, a guide nucleic acid may be gRNA that is capable of complementarily binding to a target sequence of a retinal function-forming gene.

The "retinal function-forming (retinal function formation)" means all procedures enabling retinal functions, for example, all functions required for detecting light entering eyes through the inner layer of the retina by visual cells, converting the light energy or signal detected by the visual cells into electrical energy or signal and delivering the energy or signal to the optic nerve by cells in the retinal inner layer to normally operate.

In addition, the retinal function-forming includes all procedures enabling several layers or membranes constituting retinal tissue, for example, the retinal pigmented epithelium, a photoreceptor cell layer, an external limiting membrane, an outer nuclear layer, an outer plexiform layer, an inner nuclear layer, an inner plexiform layer, a ganglion cell layer, a nerve fiber layer and an internal limiting membrane, to normally function.

The retinal function forming also includes all procedures enabling functions of various tissues and/or cells responsible for normally functioning retinal tissue to normally operate. Here, various tissues and/or cells responsible for normally functioning retinal tissue include tissue close to retinal tissue, for example, the choroid, the cornea, the sclera, the iris, the ciliary body and/or cells constituting the tissue.

In addition, the retinal function forming includes overall development and growth processes including the survival, proliferation, persistence and death of retinal cells. Here, retinal cells include neurons, glial cells, cone cells, rod cells, and RPE cells.

The retinal function forming may be a light-detection function of cone cells and/or rod cells.

The retinal function forming may be a function relating to a visual cycle.

Here, the visual cycle is a cyclic process of the photochemical change and regeneration of rhodopsin, which is a visual receptor, and includes a process of changing 11-cis-retinol in rhodopsin into the all-trans form due to photosynthesis.

The retinal function forming may be the regulation of expression of a visual cycle-related gene and/or protein.

The retinal function forming may be a visual pigment regeneration-related function.

The "retinal function-forming gene" means any gene which directly participates in or indirectly affects the formation of retinal functions. Here, the gene includes any gene or nucleic acid sequence which encodes any peptide, polypeptide or protein directly participating in or indirectly affecting the formation of retinal functions.

The retinal function-forming gene may be a wild-type retinal function-forming gene.

The retinal function-forming gene may be a retinal function-forming gene including one or more mutations.

The "mutation" means the occurrence of a change in the base sequence of DNA of a gene, and includes any modification in which one or more nucleotides in the base sequence of DNA of a gene are deleted, inserted or substituted. Here, a sequence in which a mutation occurs in a gene refers to a "mutant sequence (mutation sequence)." In addition, a mutation includes any modification in which some amino acids of a protein encoded by a gene are deleted, inserted or substituted due to a mutation in the gene.

For example, when the retinal function-forming gene is a RPE65 gene, the RPE65 gene includes a wild-type RPE65 gene and all mutant forms of the RPE65 gene which can naturally occur. There are 86 naturally-occurring mutations of the RPE65 gene, which have been found to date, and the RPE65 gene disclosed herein includes all mutations. In one example, the RPE65 gene may include IVS-2A>C, IVS-2A>T, IVS2+1G>T, c.57_84 delGG, c90_91 insT, c.137delG, c106_114 del9 bp, c.292_311del20 bp, c.440_441delCA, c.495_496insG, IVS6-2A>T, IVS6-1G>T, IVS6+1G>C, c.615_616 delCA, IVS7+4A>G, IVS8+1G>A, IVS8+4A>G, c.891delA, c.894delG, c.1064delA, c.1120delA, c.961_962 insA, IVS11+2T>A, c.1056G>A, c.1059_1060insG, c.1069_1070insT, c.1243+2T>A, c.1338+20A>C, c.1417_1418delinsA, c.1590delC, c.1590C>A or c.1499_1503del15 bp mutations of the RPE65 gene, which are naturally occurring mutations. In another example, the RPE65 gene may include a mutant RPE gene encoding an RPE65 protein with MIT, E6 deletion, G32V, R44Q, L60P, Q64 deletion, F70V, R91Q, R91P, T101I, G104D, R118S, Y144D, E148D, T162P, H182R, H182N, N205S, D215G, R234 deletion, Y239D, Y249C, V287F, K303 deletion, H313R, Y318N, N321K, C330Y, L343 deletion, A360P, Y368C, A393G, W402 deletion, L403P, V407A, L408P, E417Q, Y431C, A434V, Y435C, G436V, V443A, W458 deletion, W460 deletion, E462 deletion, or P470L, G528V, F530L or S533T mutation, which naturally occurs.

Here, the one or more mutations may increase or decrease the expression of a protein encoded by a retinal function-forming gene.

Here, the one or more mutations may be synonymous mutations which do not affect the expression of a protein encoded by a retinal function-forming gene.

Here, the one or more mutations may be nonsense mutations which block the expression of a protein encoded by a retinal function-forming gene.

The retinal function-forming gene may promote or increase the formation of a retinal function.

The retinal function-forming gene may suppress or inhibit the formation of a retinal function.

The retinal function-forming gene may induce or activate a retinal function-forming environment.

The retinal function-forming gene may induce a retinal function formation-inhibitory environment or inactivate an angiogenic environment.

The retinal function-forming gene may regulate (promote, increase, suppress and/or inhibit) the formation of a retinal function.

The retinal function-forming gene may express a protein which performs a light-detection function of a cone cell and/or rod cell.

The retinal function-forming gene may promote or increase a light-detection function of a cone cell and/or rod cell.

The retinal function-forming gene may suppress or inhibit a light-detection function of a cone cell and/or rod cell.

The retinal function-forming gene may promote or increase a visual cycle-related function.

The retinal function-forming gene may suppress or inhibit a visual cycle-related function.

The retinal function-forming gene may express a protein performing a visual cycle-related function.

The retinal function-forming gene may regulate the expression of a gene and/or protein performing a visual cycle-related function.

The retinal function-forming gene may express a protein performing a visual pigment regeneration-related function.

The retinal function-forming gene may promote or increase a visual pigment regeneration-related function.

The retinal function-forming gene may suppress or inhibit a visual pigment regeneration-related function.

The retinal function-forming gene may be used in improvement and treatment of a retinal dysfunction disease.

In one embodiment,
the retinal function-forming gene disclosed in the present specification may be one or more genes selected from the group consisting of a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and a CRX gene.

In an embodiment, the retinal function-forming gene may be a RPE65 gene.

The retinal pigment epithelium-specific 65 kDa protein (RPE65) gene refers to a gene (full-length DNA, cDNA or mRNA) encoding protein RPE65 called BCO3, LCA2, RP20 or mrd12. In one example, the RPE65 gene may be one or more genes selected from the group as follows, but the present invention is not limited thereto: a gene encoding human RPE65 (e.g., NCBI Accession No. NP_000320, etc.), for example, a RPE65 gene represented by NCBI Accession No. NM_000329.

The RPE65 gene may include a mutation such as IVS-2A>C, IVS-2A>T, IVS2+1G>T, c.57_84 delGG, c90_91 insT, c.137delG, c106_114 del9 bp, c.292_311del20 bp, c.440_441delCA, c.495_496insG, IVS6-2A>T, IVS6-1G>T, IVS6+1G>C, c.615_616 delCA, IVS7+4A>G, IVS8+1G>A, IVS8+4A>G, c.891delA, c.894delG, c.1064delA, c.1120delA, c.961_962 insA, IVS11+2T>A, c.1056G>A, c.1059_1060insG, c.1069_1070insT, c.1243+2T>A, c.1338+20A>C, c.1417_1418delinsA, c.1590delC, c.1590C>A or c.1499_1503del15 bp.

The RPE65 gene may include a mutant RPE65 gene encoding a RPE65 protein mutation such as MIT, E6 deletion, G32V, R44Q, L60P, Q64 deletion, F70V, R91Q, R91P, T101I, G104D, R118S, Y144D, E148D, T162P, H182R, H182N, N205S, D215G, R234 deletion, Y239D, Y249C, V287F, K303 deletion, H313R, Y318N, N321K, C330Y, L343 deletion, A360P, Y368C, A393G, W402 deletion, L403P, V407A, L408P, E417Q, Y431C, A434V, Y435C, G436V, V443A, W458 deletion, W460 deletion, E462 deletion, P470L, G528V, F530L or S533T.

In an embodiment, the retinal function-forming gene may be a GUCY2D gene.

The guanylate cyclase 2D (GUCY2D) gene refers to a gene (full-length DNA, cDNA or mRNA) encoding protein GUCY2D also called CORDS, CORD6, CYGD, GUC1A4, GUC2D, LCA1, RCD2, RETGC-1, ROS-GC1 or ROSGC. In one example, the GUCY2D gene may be one or more genes selected from the group as follows, but the present invention is not limited thereto: a gene encoding human GUCY2D (e.g., NCBI Accession No. NP_000171 etc.), for example, a GUCY2D gene represented by NCBI Accession No. NM_000180.

In an embodiment, the retinal function-forming gene may be a SPATA7 gene.

The spermatogenesis-associated protein 7 (SPATA7) gene refers to a gene (full-length DNA, cDNA or mRNA) encoding protein SPATA7 also called HSD3 or LCA3. In one example, the SPATA7 gene may be one or more genes selected from the group as follows, but the present invention is not limited thereto: genes encoding human SPATA7 (e.g., NCBI Accession Nos. NP_001035518, NP_060888, etc.), for example, SPATA7 genes represented by NCBI Accession Nos. NM_001040428, NM_018418, etc.

In an embodiment, the retinal function-forming gene may be an AIPL1 gene.

The aryl-hydrocarbon-interacting protein-like 1 (AIPL1) gene refers to a gene (full-length DNA, cDNA or mRNA) encoding protein AIPL1 also called LCA4. In one example, the AIPL1 gene may be one or more genes selected from the group as follows, but the present invention is not limited thereto: genes encoding human AIPL1 (e.g., NCBI Accession Nos. NP_001028226, NP_001028227, etc.), for example, AIPL1 genes represented by NCBI Accession Nos. NM_014336, NM_001033054, etc.

In an embodiment, the retinal function-forming gene may be a LCA5 gene.

The Leber congenital amaurosis 5 (LCA5) gene refers to a gene (full-length DNA, cDNA or mRNA) encoding protein LCA5 also called lebercilin or C6orf152. In one example, the LCA5 gene may be one or more genes selected from the group as follows, but the present invention is not limited thereto: genes encoding human LCA5 (e.g., NCBI Accession Nos. NP_001116241, NP_859065, etc.), for example, LCA5 genes represented by NCBI Accession Nos. NM_001122769, NM_181714, etc.

In an embodiment, the retinal function-forming gene may be an RPGRIP1 gene.

The X-linked retinitis pigmentosa GTPase regulator-interacting protein 1 (RPGRIP1) gene refers to a gene (full-length DNA, cDNA or mRNA) encoding protein RPGRIP1 also called CORD13, LCA6, RGI1, RGRIP, RPGRIP or RPGRIP1d. In one example, the RPGRIP1 gene may be one or more genes selected from the group as follows, but the present invention is not limited thereto: a gene encoding human RPGRIP1 (e.g., NCBI Accession No. NP_065099, etc.), for example, a RPGRIP1 gene represented by NCBI Accession No. NM_020366, etc.

In an embodiment, the retinal function-forming gene may be a CRB1 gene.

The crumbs homolog 1 (CRB1) gene refers to a gene (full-length DNA, cDNA or mRNA) encoding protein CRB1 also called LCA8 or RP12. In one example, the CRB1 gene may be one or more genes selected from the group as follows, but the present invention is not limited thereto: genes encoding human CRB1 (e.g., NCBI Accession Nos. NP_001180569, NP_001244894, etc.), for example, CRB1 genes represented by NCBI Accession Nos. NM_001193640, NM_001257965, etc.

In an embodiment, the retinal function-forming gene may be a CEP290 gene.

The centrosomal protein of 290 kDa (CEP290) gene refers to a gene (full-length DNA, cDNA or mRNA) encoding protein CEP290 also called BBS14, CT87, JBTS5 or LCA10. In one example, the CEP290 gene may be one or more genes selected from the group as follows, but the present invention is not limited thereto: a gene encoding human CEP290 (e.g., NCBI Accession No. NP_079390, etc.), for example, a CEP290 gene represented by NCBI Accession No. NM_025114, etc.

In an embodiment, the retinal function-forming gene may be an IMPDH1 gene.

The inosine-5'-monophosphate dehydrogenase 1 (IMPDH1) gene refers to a gene (full-length DNA, cDNA or mRNA) encoding protein IMPDH1 also called IMPD1, IMPDH-I, LCA11 or RP10. In one example, the IMPDH1 gene may be one or more genes selected from the group as follows, but the present invention is not limited thereto: genes encoding human IMPDH1 (e.g., NCBI Accession Nos. NP_000874, NP_001096075, etc.), for example, IMPDH1 genes represented by NCBI Accession Nos. NM_000883, NM_001102605, etc.

In an embodiment, the retinal function-forming gene may be a RD3 gene.

The retinal degeneration 3 (RD3) gene refers to a gene (full-length DNA, cDNA or mRNA) encoding protein RD3 also called LCA12 or C1orf36. In one example, the RD3 gene may be one or more genes selected from the group as follows, but the present invention is not limited thereto: genes encoding human RD3 (e.g., NCBI Accession Nos. NP_001158160.1, NP_898882.1, etc.), for example, RD3 genes represented by NCBI Accession Nos. NM_001164688.1, NM_183059.2, etc.

In an embodiment, the retinal function-forming gene may be a RDH12 gene.

The retinol dehydrogenase 12 (RDH12) gene refers to a gene (full-length DNA, cDNA or mRNA) encoding protein RDH12 also called LCA13, RP53 or SDR7C2. In one example, the RDH12 gene may be one or more genes selected from the group as follows, but the present invention is not limited thereto: a gene encoding human RDH12 (e.g., NCBI Accession No. NP_689656, etc.), for example, a RDH12 gene represented by NCBI Accession No. NM_152443, etc.

In an embodiment, the retinal function-forming gene may be a CRX gene.

The cone-rod homeobox protein (CRX) gene refers to a gene (full-length DNA, cDNA or mRNA) encoding protein CRX also called CORD2, CRD, LCA7 or OTX3. In one example, the CRX gene may be one or more genes selected from the group as follows, but the present invention is not limited thereto: a gene encoding human CRX (e.g., NCBI Accession No. NP_000545, etc.), for example, a CRX gene represented by NCBI Accession No. NM_000554, etc.

The retinal function-forming gene may be derived from mammals including primates such as a human, a monkey, etc. and rodents such as a rat, a mouse, etc.

Genetic information may be obtained from known database such as GenBank of the National Center for Biotechnology Information (NCBI).

In One Embodiment of the Disclosure in the Present Specification, the Guide Nucleic Acid May be gRNA Complementarily Binding to a Target Sequence of a RPE65 Gene, a GUCY2D Gene, a SPATA7 Gene, an AIPL1 Gene, a LCA5 Gene, a RPGRIP1 Gene, a CRB1 Gene, a CEP290 Gene, an IMPDH1 Gene, a RD3 Gene, a RDH12 Gene and/or a CRX Gene.

The "target sequence" is a nucleotide sequence present in the transcriptional regulatory region of a target gene, and specifically, a partial nucleotide sequence in a target region in a target gene or a nucleic acid, and here, the "target region" is a region that can be modified by a guide nucleic acid-editor protein in a target gene or a nucleic acid.

Hereinafter, the target sequence may be used to refer to both of two types of nucleotide sequence information. For example, in the case of a target gene, the target sequence may refer to the nucleotide sequence information of a transcribed strand of target gene DNA, or the nucleotide sequence information of a non-transcribed strand.

For example, the target sequence may refer to a partial nucleotide sequence (transcribed strand), that is, 5'-ATCATTGGCAGACTAGTTCG-3' (SEQ ID NO: 239), in the target region of target gene A, and a nucleotide sequence complementary thereto (non-transcribed strand), that is, 5'-CGAACTAGTCTGCCAATGAT-3' (SEQ ID NO: 240).

The target sequence may be a 5 to 50-nt sequence.

In one exemplary embodiment, the target sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The target sequence includes a guide nucleic acid-binding sequence or a guide nucleic acid-non binding sequence.

The "guide nucleic acid-binding sequence" is a nucleotide sequence having partial or complete complementarity with a guide sequence included in the guide domain of the guide nucleic acid, and may be complementarily bonded with the guide sequence included in the guide domain of the guide nucleic acid. The target sequence and guide nucleic acid-binding sequence may be a nucleotide sequence that may vary according to a target to be genetically engineered or edited depending on the transcriptional regulatory region of the target gene, and may be designed in various ways according to a target gene or a nucleic acid.

The "guide nucleic acid-non binding sequence" is a nucleotide sequence having partial or complete homology with a guide sequence included in the guide domain of the guide nucleic acid, and may not be complementarily bonded with the guide sequence included in the guide domain of the guide nucleic acid. In addition, the guide nucleic acid-non binding sequence may be a nucleotide sequence having complementarity with the guide nucleic acid-binding sequence, and may be complementarily bonded with the guide nucleic acid-binding sequence.

The guide nucleic acid-binding sequence may be a partial nucleotide sequence of the target sequence, and one nucleotide sequence of two nucleotide sequences having different sequence order to each other included in the target sequence, that is, one of the two nucleotide sequences capable of complementary binding to each other. Here, the guide nucleic acid-non binding sequence may be a nucleotide sequence other than the guide nucleic acid-binding sequence of the target sequence.

For example, when a partial nucleotide sequence, that is, 5'-ATCATTGGCAGACTAGTTCG-3' (SEQ ID NO: 239), of a target region in the transcriptional regulatory region of the target gene A, and a nucleotide sequence, that is, 5'-CGAACTAGTCTGCCAATGAT-3' (SEQ ID NO: 240), which is complementary thereto, are used as target sequences, the guide nucleic acid-binding sequence may be one of the two target sequences, that is, 5'-ATCATTGGCAGACTAGTTCG-3' (SEQ ID NO: 239) or 5'-CGAACTAGTCTGCCAATGAT-3' (SEQ ID NO: 240). Here, when the guide nucleic acid-binding sequence is 5'-ATCATTGGCAGACTAGTTCG-3' (SEQ ID NO: 239), the guide nucleic acid-non binding sequence may be 5'-CGAACTAGTCTGCCAATGAT-3' (SEQ ID NO: 240), or when the guide nucleic acid-binding sequence is 5'-CGAACTAGTCTGCCAATGAT-3' (SEQ ID NO: 240), the guide nucleic acid-non binding sequence may be 5'-ATCATTGGCAGACTAGTTCG-3' (SEQ ID NO: 239).

The guide nucleic acid-binding sequence may be one of the target sequences, that is, a nucleotide sequence which is the same as a transcribed strand and a nucleotide sequence which is the same as a non-transcribed strand. Here, the guide nucleic acid-non binding sequence may be a nucleotide sequence other than the guide nucleic acid-binding sequence of the target sequences, that is, one selected from a nucleotide sequence which is the same as a transcribed strand and a nucleotide sequence which is the same as a non-transcribed strand.

The guide nucleic acid-binding sequence may have the same length as the target sequence.

The guide nucleic acid-non binding sequence may have the same length as the target sequence or the guide nucleic acid-binding sequence.

The guide nucleic acid-binding sequence may be a 5 to 50-nt sequence.

In one exemplary embodiment, the guide nucleic acid-binding sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The guide nucleic acid-non binding sequence may be a 5 to 50-nt sequence.

In one exemplary embodiment, the guide nucleic acid-nonbinding sequence may be a 16-nt sequence, a 17-nt sequence, a 18-nt sequence, a 19-nt sequence, a 20-nt sequence, a 21-nt sequence, a 22-nt sequence, a 23-nt sequence, a 24-nt sequence or a 25-nt sequence.

The guide nucleic acid-binding sequence may partially or completely complementarily bind to the guide sequence included in the guide domain of the guide nucleic acid, and the length of the guide nucleic acid-binding sequence may be the same as that of the guide sequence.

The guide nucleic acid-binding sequence may be a nucleotide sequence complementary to the guide sequence included in the guide domain of the guide nucleic acid, and for example, a nucleotide sequence which has at least 70%, 75%, 80%, 85%, 90%, 95% or more complementarity or complete complementarity.

As an example, the guide nucleic acid-binding sequence may have or include a 1 to 8-nt sequence which is not complementary to the guide sequence included in the guide domain of the guide nucleic acid.

The guide nucleic acid-non binding sequence may have partial or complete homology with the guide sequence included in the guide domain of the guide nucleic acid, and the length of the guide nucleic acid-non binding sequence may be the same as that of the guide sequence.

The guide nucleic acid-non binding sequence may be a nucleotide sequence having homology with the guide sequence included in the guide domain of the guide nucleic acid, and for example, a nucleotide sequence which has at least 70%, 75%, 80%, 85%, 90%, 95% or more homology or complete homology.

In one example, the guide nucleic acid-non binding sequence may have or include a 1 to 8-nt sequence which is not homologous to the guide sequence included in the guide domain of the guide nucleic acid.

The guide nucleic acid-non binding sequence may complementarily bind with the guide nucleic acid-binding sequence, and the guide nucleic acid-non binding sequence may have the same length as the guide nucleic acid-binding sequence.

The guide nucleic acid-non binding sequence may be a nucleotide sequence complementary to the guide nucleic acid-binding sequence, and for example, a nucleotide sequence having at least 90%, 95% or more complementarity or complete complementarity.

In one example, the guide nucleic acid-non binding sequence may have or include a 1 to 2-nt sequence which is not complementary to the guide nucleic acid-binding sequence.

In addition, the guide nucleic acid-binding sequence may be a nucleotide sequence located near a nucleotide sequence recognized by an editor protein.

In one example, the guide nucleic acid-binding sequence may be a consecutive 5 to 50-nt sequence located adjacent to the 5' end and/or 3' end of a nucleotide sequence recognized by an editor protein.

In addition, the guide nucleic acid-non binding sequence may be a nucleotide sequence located near a nucleotide sequence recognized by an editor protein.

In one example, the guide nucleic acid-non binding sequence may be a 5 to 50-nt contiguous sequence located adjacent to the 5' end and/or 3' end of a nucleotide sequence recognized by an editor protein.

The "targeting" refers to complementary binding with the guide nucleic acid-binding sequence of the target sequence present in a target gene or a nucleic acid. Here, the complementary binding may be 100% completely complementary binding, or 70% or more and less than 100%, incomplete complementary binding. Therefore, the "targeting gRNA" refers to gRNA complementarily binding to the guide nucleic acid-binding sequence of the target sequence present in a target gene or a nucleic acid.

The target gene disclosed in the specification may be a retinal function-forming gene.

The target gene disclosed in the specification may be a RPE65 gene, a GUCY2D gene, a SPATA7 gene, an AIPL1 gene, a LCA5 gene, a RPGRIP1 gene, a CRB1 gene, a CEP290 gene, a IMPDH1 gene, a RD3 gene, a RDH12 gene and/or a CRX gene.

In an embodiment, the target sequence disclosed in the present specification may be a 10 to 35-nt contiguous sequence located in the promoter region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

In addition, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in the promoter region of the RPE65 gene.

In another example, the target sequence may be a 10 to 25 contiguous nucleotide sequence located in the promoter region of the GUCY2D gene.

In one example, the target sequence may be a 10 to 25-nt contiguous sequence located in the promoter region of the SPATA7 gene.

In another example, the target sequence may be a 10 to 25-nt contiguous sequence located in the promoter region of the AIPL1 gene.

In one example, the target sequence may be a 10 to 25-nt contiguous sequence located in the promoter region of the LCA5 gene.

In another example, the target sequence may be a 10 to 25-nt contiguous sequence located in the promoter region of the RPGRIP1 gene.

In one example, the target sequence may be a 10 to 25-nt contiguous sequence located in the promoter region of the CRB1 gene.

In another example, the target sequence may be a 10 to 25-nt contiguous sequence located in the promoter region of the CEP290 gene.

In one example, the target sequence may be a 10 to 25-nt contiguous sequence located in the promoter region of the IMPDH1 gene.

In another example, the target sequence may be a 10 to 25-nt contiguous sequence located in the promoter region of the RD3 gene.

In one example, the target sequence may be a 10 to 25-nt contiguous sequence located in the promoter region of the RDH12 gene.

In another example, the target sequence may be a 10 to 25-nt contiguous sequence located in the promoter region of the CRX gene.

The target sequence disclosed in the present specification may be a 10 to 35-nt contiguous sequence located in an intron region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in an intron region of the RPE65 gene.

In another example, the target sequence may be a 10 to 25-nt contiguous sequence located in an intron region of the GUCY2D gene.

In one example, the target sequence may be a 10 to 25-nt contiguous sequence located in an intron region of the SPATA7 gene.

In another example, the target sequence may be a 10 to 25-nt contiguous sequence located in an intron region of the AIPL1 gene.

In one example, the target sequence may be a 10 to 25-nt contiguous sequence located in an intron region of the LCA5 gene.

In another example, the target sequence may be a 10 to 25-nt contiguous sequence located in an intron region of the RPGRIP1 gene.

In one example, the target sequence may be a 10 to 25-nt contiguous sequence located in an intron region of the CRB1 gene.

In another example, the target sequence may be a 10 to 25-nt contiguous sequence located in an intron region of the CEP290 gene.

In one example, the target sequence may be a 10 to 25-nt contiguous sequence located in an intron region of the IMPDH1 gene.

In another example, the target sequence may be a 10 to 25-nt contiguous sequence located in an intron region of the RD3 gene.

In one example, the target sequence may be a 10 to 25-nt contiguous sequence located in an intron region of the RDH12 gene.

In another example, the target sequence may be a 10 to 25-nt contiguous sequence located in an intron region of the CRX gene.

The target sequence disclosed in the present specification may be a 10 to 35-nt contiguous sequence located in an exon region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in an exon region of the RPE65 gene.

In another example, the target sequence may be a 10 to 25-nt contiguous sequence located in an exon region of the GUCY2D gene.

In one example, the target sequence may be a 10 to 25-nt contiguous sequence located in an exon region of the SPATA7 gene.

In another example, the target sequence may be a 10 to 25-nt contiguous sequence located in an exon region of the AIPL1 gene.

In one example, the target sequence may be a 10 to 25-nt contiguous sequence located in an exon region of the LCA5 gene.

In another example, the target sequence may be a 10 to 25-nt contiguous sequence located in an exon region of the RPGRIP1 gene.

In one example, the target sequence may be a 10 to 25-nt contiguous sequence located in an exon region of the CRB1 gene.

In another example, the target sequence may be a 10 to 25-nt contiguous sequence located in an exon region of the CEP290 gene.

In one example, the target sequence may be a 10 to 25-nt contiguous sequence located in an exon region of the IMPDH1 gene.

In another example, the target sequence may be a 10 to 25-nt contiguous sequence located in an exon region of the RD3 gene.

In one example, the target sequence may be a 10 to 25-nt contiguous sequence located in an exon region of the RDH12 gene.

In another example, the target sequence may be a 10 to 25-nt contiguous sequence located in an exon region of the CRX gene.

The target sequence disclosed in the present specification may be a 10 to 35-nt contiguous sequence located in an enhancer region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in an enhancer region of the RPE65 gene.

In another example, the target sequence may be a 10 to 25-nt contiguous sequence located in an enhancer region of the GUCY2D gene.

In one example, the target sequence may be a 10 to 25-nt contiguous sequence located in an enhancer region of the SPATA7 gene.

In another example, the target sequence may be a 10 to 25-nt contiguous sequence located in an enhancer region of the AIPL1 gene.

In one example, the target sequence may be a 10 to 25-nt contiguous sequence located in an enhancer region of the LCA5 gene.

In another example, the target sequence may be a 10 to 25-nt contiguous sequence located in an enhancer region of the RPGRIP1 gene.

In one example, the target sequence may be a 10 to 25-nt contiguous sequence located in an enhancer region of the CRB1 gene.

In another example, the target sequence may be a 10 to 25-nt contiguous sequence located in an enhancer region of the CEP290 gene.

In one example, the target sequence may be a 10 to 25-nt contiguous sequence located in an enhancer region of the IMPDH1 gene.

In another example, the target sequence may be a 10 to 25-nt contiguous sequence located in an enhancer region of the RD3 gene.

In one example, the target sequence may be a 10 to 25-nt contiguous sequence located in an enhancer region of the RDH12 gene.

In another example, the target sequence may be a 10 to 25-nt contiguous sequence located in an enhancer region of the CRX gene.

The target sequence disclosed in the present specification may be a 10 to 35-nt contiguous sequence located in a coding region, a non-coding region or a mixed region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in a coding region, a non-coding region or a mixed region of the RPE65 gene.

In another example, the target sequence may be a 10 to 25-nt contiguous sequence located in a coding region, a non-coding region or a mixed region of the GUCY2D gene.

In one example, the target sequence may be a 10 to 25-nt contiguous sequence located in a coding region, a non-coding region or a mixed region of the SPATA7 gene.

In another example, the target sequence may be a 10 to 25-nt contiguous sequence located in a coding region, a non-coding region or a mixed region of the AIPL1 gene.

In one example, the target sequence may be a 10 to 25-nt contiguous sequence located in a coding region, a non-coding region or a mixed region of the LCA5 gene.

In another example, the target sequence may be a 10 to 25-nt contiguous sequence located in a coding region, a non-coding region or a mixed region of the RPGRIP1 gene.

In one example, the target sequence may be a 10 to 25-nt contiguous sequence located in a coding region, a non-coding region or a mixed region of the CRB1 gene.

In another example, the target sequence may be a 10 to 25-nt contiguous sequence located in a coding region, a non-coding region or a mixed region of the CEP290 gene.

In one example, the target sequence may be a 10 to 25-nt contiguous sequence located in a coding region, a non-coding region or a mixed region of the IMPDH1 gene.

In another example, the target sequence may be a 10 to 25-nt contiguous sequence located in a coding region, a non-coding region or a mixed region of the RD3 gene.

In one example, the target sequence may be a 10 to 25-nt contiguous sequence located in a coding region, a non-coding region or a mixed region of the RDH12 gene.

In another example, the target sequence may be a 10 to 25-nt contiguous sequence located in a coding region, a non-coding region or a mixed region of the CRX gene.

The target sequence disclosed in the present specification may be a 10 to 35-nt contiguous sequence located in a promoter, an enhancer, a 3' UTR, a polyA region or a mixed region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in a promoter, an enhancer, a 3' UTR, a polyA region or a mixed region of the RPE65 gene.

In another example the target sequence may be a 10 to 25-nt contiguous sequence located in a promoter, an enhancer, a 3' UTR, a polyA region or a mixed region of the GUCY2D gene.

In one example, the target sequence may be a 10 to 25-nt contiguous sequence located in a promoter, an enhancer, a 3' UTR, a polyA region or a mixed region of the SPATA7 gene.

In another example, the target sequence may be a 10 to 25-nt contiguous sequence located in a promoter, an enhancer, a 3' UTR, a polyA region or a mixed region of the AIPL1 gene.

In one example, the target sequence may be a 10 to 25-nt contiguous sequence located in the promoter, enhancer, 3' UTR, polyA region or a mixed region of the LCA5 gene.

In another example, the target sequence may be a 10 to 25-nt contiguous sequence located in a promoter, an enhancer, a 3' UTR, a polyA region or a mixed region of the RPGRIP1 gene.

In one example, the target sequence may be a 10 to 25-nt contiguous sequence located in a promoter, an enhancer, a 3' UTR, a polyA region or a mixed region of the CRB1 gene.

In another example, the target sequence may be a 10 to 25-nt contiguous sequence located in a promoter, an enhancer, a 3' UTR, a polyA region or a mixed region of the CEP290 gene.

In one example, the target sequence may be a 10 to 25-nt contiguous sequence located in a promoter, an enhancer, a 3' UTR, a polyA region or a mixed region of the IMPDH1 gene.

In another example, the target sequence may be a 10 to 25-nt contiguous sequence located in a promoter, an enhancer, a 3' UTR, a polyA region or a mixed region of the RD3 gene.

In one example, the target sequence may be a 10 to 25-nt contiguous sequence located in a promoter, an enhancer, a 3' UTR, a polyA region or a mixed region of the RDH12 gene.

In another example, the target sequence may be a 10 to 25-nt contiguous sequence located in a promoter, an enhancer, a 3' UTR, a polyA region or a mixed region of the CRX gene.

The target sequence disclosed in the present specification may be a 10 to 35-nt contiguous sequence located in an exon, an intron or a mixed region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence located in an exon, an intron or a mixed region of the RPE65 gene.

In another example, the target sequence may be a 10 to 25-nt contiguous sequence located in an exon, an intron or a mixed region of the GUCY2D gene.

In one example, the target sequence may be a 10 to 25-nt contiguous sequence located in an exon, an intron or a mixed region of the SPATA7 gene.

In another example, the target sequence may be a 10 to 25-nt contiguous sequence located in an exon, an intron or a mixed region of the AIPL1 gene.

In one example, the target sequence may be a 10 to 25-nt contiguous sequence located in an exon, an intron or a mixed region of the LCA5 gene.

In another example, the target sequence may be a 10 to 25-nt contiguous sequence located in an exon, an intron or a mixed region of the RPGRIP1 gene.

In one example, the target sequence may be a 10 to 25-nt contiguous sequence located in an exon, an intron or a mixed region of the CRB1 gene.

In another example, the target sequence may be a 10 to 25-nt contiguous sequence located in an exon, an intron or a mixed region of the CEP290 gene.

In one example, the target sequence may be a 10 to 25-nt contiguous sequence located in an exon, an intron or a mixed region of the IMPDH1 gene.

In another example, the target sequence may be a 10 to 25-nt contiguous sequence located in an exon, an intronor a mixed region of the RD3 gene.

In one example, the target sequence may be a 10 to 25-nt contiguous sequence located in an exon, an intron or a mixed region of the RDH12 gene.

In another example, the target sequence may be a 10 to 25-nt contiguous sequence located in an exon, an intron or a mixed region of the CRX gene.

The target sequence disclosed in the present specification may be a 10 to 35-nt contiguous sequence which includes or is adjacent to a mutant part (e.g., a part different from a wild-type gene) of the retinal function-forming gene.

Here, the mutant part may be located in a promoter, an enhancer, an exon and/or an intron region of the retinal function-forming gene.

Here, the target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence which includes or is adjacent to a mutant part (e. g, a part different from a wild-type gene) of the RPE65 gene.

In another example, the target sequence may be a 10 to 25-nt contiguous sequence which includes or is adjacent to a mutant part (e. g, a part different from a wild-type gene) of the GUCY2D gene.

In one example, the target sequence may be a 10 to 25-nt contiguous sequence which includes or is adjacent to a mutant part (e. g, a part different from a wild-type gene) of the SPATA7 gene.

In another example, the target sequence may be a 10 to 25-nt contiguous sequence which includes or is adjacent to a mutant part (e. g, a part different from a wild-type gene) of the AIPL1 gene.

In one example, the target sequence may be a 10 to 25-nt contiguous sequence which includes or is adjacent to a mutant part (e. g, a part different from a wild-type gene) of the LCA5 gene.

In another example, the target sequence may be a 10 to 25-nt contiguous sequence which includes or is adjacent to a mutant part (e. g, a part different from a wild-type gene) of the RPGRIP1 gene.

In one example, the target sequence may be a 10 to 25-nt contiguous sequence which includes or is adjacent to a mutant part (e. g, a part different from a wild-type gene) of the CRB1 gene.

In another example, the target sequence may be a 10 to 25-nt contiguous sequence which includes or is adjacent to a mutant part (e. g, a part different from a wild-type gene) of the CEP290 gene.

In one example, the target sequence may be a 10 to 25-nt contiguous sequence which includes or is adjacent to a mutant part (e. g, a part different from a wild-type gene) of the IMPDH1 gene.

In another example, the target sequence may be a 10 to 25-nt contiguous sequence which includes or is adjacent to a mutant part (e. g, a part different from a wild-type gene) of the RD3 gene.

In one example, the target sequence may be a 10 to 25-nt contiguous sequence which includes or is adjacent to a mutant part (e. g, a part different from a wild-type gene) of the RDH12 gene.

In another example, the target sequence may be a 10 to 25-nt contiguous sequence which includes or is adjacent to a mutant part (e. g, a part different from a wild-type gene) of the CRX gene.

The target sequence disclosed in the present specification may be a 10 to 35-nt contiguous sequence which is adjacent to the 5' end and/or 3' end of a proto-spacer-adjacent motif (PAM) sequence in the nucleic acid sequence of the retinal function-forming gene.

The "proto-spacer-adjacent motif (PAM) sequence" is a nucleotide sequence that can be recognized by an editor protein. Here, the PAM sequence may have different nucleotide sequences according to the type of the editor protein and an editor protein-derived species.

Here, the PAM sequence may be, for example, one or more sequences of the following sequences (described in a 5' to 3' direction).

NGG (N is A, T, C or G);
NNNNRYAC (N is each independently A, T, C or G, R is A or G, and Y is C or T);
NNAGAAW (N is each independently A, T, C or G, and W is A or T);
NNNNGATT (N is each independently A, T, C or G);
NNGRR(T) (N is each independently A, T, C or G, and R is A or G); and
TTN (N is A, T, C or G).

The target sequence may be a 10 to 35-nt sequence, a 15 to 35-nt sequence, a 20 to 35-nt sequence, a 25 to 35-nt sequence or a 30 to 35-nt sequence.

Alternatively, the target sequence may be a 10 to 15-nt sequence, a 15 to 20-nt sequence, a 20 to 25-nt sequence, a 25 to 30-nt sequence or a 30 to 35-nt sequence.

In one example, the target sequence may be a 10 to 25-nt contiguous sequence adjacent to the 5' end and/or 3' end of a PAM sequence in the nucleic acid sequence of the RPE65 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the RPE65 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the RPE65 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the RPE65 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the RPE65 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the RPE65 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the RPE65 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the RPE65 gene.

In another example, the target sequence may be a 10 to 25-nt contiguous sequence adjacent to the 5' end and/or 3' end of a PAM sequence in the nucleic acid sequence of the GUCY2D gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the GUCY2D gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the GUCY2D gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the GUCY2D gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the GUCY2D gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the GUCY2D gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the GUCY2D gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the GUCY2D gene.

In one example, the target sequence may be a 10 to 25-nt contiguous sequence adjacent to the 5' end and/or 3' end of a PAM sequence in the nucleic acid sequence of the SPATA7 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the SPATA7 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the SPATA7 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the SPATA7 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the SPATA7 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the SPATA7 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the SPATA7 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the SPATA7 gene.

In another example, the target sequence may be a 10 to 25-nt contiguous sequence adjacent to the 5' end and/or 3' end of a PAM sequence in the nucleic acid sequence of the AIPL1 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the AIPL1 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the AIPL1 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the AIPL1 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the AIPL1 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the AIPL1 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the AIPL1 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the AIPL1 gene.

In one example, the target sequence may be a 10 to 25-nt contiguous sequence adjacent to the 5' end and/or 3' end of a PAM sequence in the nucleic acid sequence of the LCA5 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the LCA5 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the LCA5 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the LCA5 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the LCA5 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the LCA5 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the LCA5 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the LCA5 gene.

In another example, the target sequence may be a 10 to 25-nt contiguous sequence adjacent to the 5' end and/or 3' end of a PAM sequence in the nucleic acid sequence of the RPGRIP1 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the RPGRIP1 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the RPGRIP1 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the RPGRIP1 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the RPGRIP1 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the RPGRIP1 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the RPGRIP1 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the RPGRIP1 gene.

In one example, the target sequence may be a 10 to 25-nt contiguous sequence adjacent to the 5' end and/or 3' end of a PAM sequence in the nucleic acid sequence of the CRB1 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the CRB1 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the CRB1 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the CRB1 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the CRB1 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the CRB1 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the CRB1 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the CRB1 gene.

In another example, the target sequence may be a 10 to 25-nt contiguous sequence adjacent to the 5' end and/or 3' end of a PAM sequence in the nucleic acid sequence of the CEP290 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the CEP290 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the CEP290 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the CEP290 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the CEP290 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the CEP290 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the CEP290 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the CEP290 gene.

In one example, the target sequence may be a 10 to 25-nt contiguous sequence adjacent to the 5' end and/or 3' end of a PAM sequence in the nucleic acid sequence of the IMPDH1 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the IMPDH1 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the IMPDH1 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the IMPDH1 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the IMPDH1 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the IMPDH1 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the IMPDH1 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the IMPDH1 gene.

In another example, the target sequence may be a 10 to 25-nt contiguous sequence adjacent to the 5' end and/or 3' end of a PAM sequence in the nucleic acid sequence of the RD3 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the RD3 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the RD3 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the RD3 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the RD3 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the RD3 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the RD3 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the RD3 gene.

In one example, the target sequence may be a 10 to 25-nt contiguous sequence adjacent to the 5' end and/or 3' end of a PAM sequence in the nucleic acid sequence of the RDH12 gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the RDH12 gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the RDH12 gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the RDH12 gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the RDH12 gene.

In another embodiment, when the PAM sequence recognized by an editor protein is 5'-NAAR-3'(R=A or G, N=A, T, G or C; or A, U, G or C), the target sequence may be a 10 to 25-nt contiguous sequence adjacent to the 5' end and/or 3' end of the 5'-NAAR-3'(R=A or G, N=A, T, G or C; or A, U, G or C) sequence in the nucleic acid sequence of the RDH12 gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the RDH12 gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the RDH12 gene.

In another example, the target sequence may be a 10 to 25-nt contiguous sequence adjacent to the 5' end and/or 3' end of a PAM sequence in the nucleic acid sequence of the CRX gene.

In one embodiment, when the PAM sequence recognized by an editor protein is 5'-NGG-3', 5'-NAG-3' and/or 5'-NGA-3' (N=A, T, G or C; or A, U, G or C), the target sequence may be a 10 to 25-nt contiguous sequence adjacent to the 5' end and/or 3' end of the 5'-NGG-3', 5'-NAG-3' and/or 5'-NGA-3' (N=A, T, G or C; or A, U, G or C) sequence in the nucleic acid sequence of the CRX gene.

In another embodiment, when the PAM sequence recognized by an editor protein is 5'-NGGNG-3' and/or 5'-NNAGAAW-3' (W=A or T, N=A, T, G or C; or A, U, G or C), the target sequence may be a 10 to 25-nt contiguous sequence adjacent to the 5' end and/or 3' end of the 5'-NGGNG-3' and/or 5'-NNAGAAW-3' (W=A or T, N=A, T, G or C; or A, U, G or C) sequence in the nucleic acid sequence of the CRX gene.

In still another embodiment, when the PAM sequence recognized by an editor protein is 5'-NNNNGATT-3' and/or 5'-NNNGCTT-3' (N=A, T, G or C; or A, U, G or C), the target sequence may be a 10 to 25-nt contiguous sequence adjacent to the 5' end and/or 3' end of the 5'-NNNNGATT-3' and/or 5'-NNNGCTT-3' (N=A, T, G or C; or A, U, G or C) sequence in the nucleic acid sequence of the CRX gene.

In one embodiment, when the PAM sequence recognized by an editor protein is 5'-NNNVRYAC-3' (V=G, C or A; R=A or G, Y=C or T, N=A, T, G or C; or A, U, G or C), the target sequence may be a 10 to 25-nt contiguous sequence adjacent to the 5' end and/or 3' end of the 5'-NNNVRYAC-3' (V=G, C or A; R=A or G, Y=C or T, N=A, T, G or C; or A, U, G or C) sequence in the nucleic acid sequence of the CRX gene.

In another embodiment, when the PAM sequence recognized by an editor protein is 5'-NAAR-3' (R=A or G, N=A, T, G or C; or A, U, G or C), the target sequence may be a 10 to 25-nt contiguous sequence adjacent to the 5' end and/or 3' end of the 5'-NAAR-3' (R=A or G, N=A, T, G or C; or A, U, G or C) sequence in the nucleic acid sequence of the CRX gene.

In still another embodiment, when the PAM sequence recognized by an editor protein is 5'-NNGRR-3', 5'-NNGRRT-3' and/or 5'-NNGRRV-3' (R=A or G, V=G, C or A, N=A, T, G or C; or A, U, G or C), the target sequence may be a 10 to 25-nt contiguous sequence adjacent to the 5' end and/or 3' end of the 5'-NNGRR-3', 5'-NNGRRT-3' and/or 5'-NNGRRV-3' (R=A or G, V=G, C or A, N=A, T, G or C; or A, U, G or C) sequence in the nucleic acid sequence of the CRX gene.

In one embodiment, when the PAM sequence recognized by an editor protein is 5'-TTN-3' (N=A, T, G or C; or A, U, G or C), the target sequence may be a 10 to 25-nt contiguous sequence adjacent to the 5' end and/or 3' end of the 5'-TTN-3' (N=A, T, G or C; or A, U, G or C) sequence in the nucleic acid sequence of the CRX gene.

Hereinafter, examples of target sequences that can be used in an exemplary embodiment disclosed in the specification are listed in Tables 1 and 2. The target sequences disclosed in Tables 1 and 2 are guide nucleic acid-non binding sequences, and complementary sequences thereof, that is, guide nucleic acid-binding sequences may be predicted from the sequences listed in the tables. In addition, target names shown in Tables 1 and 2 were named Sp for SpCas9 and Cj for CjCas9 according to an editor protein.

TABLE 1

Target sequences of RPE65 gene for SpCas9

| Loci. | Target name | Target (w/o PAM) | PAM | SEQ ID NO |
|---|---|---|---|---|
| Exon2 | Sp20-hRPE65-E02-#01 | AGTTTCTTGTAACCACCAGC | AGG | SEQ ID NO: 1 |
|  | Sp20-hRPE65-E02-#02 | TACATGAGCTGTGAGCGGCG | AGG | SEQ ID NO: 2 |
|  | Sp20-hRPE65-E02-#03 | CCGCTCACAGCTCATGTAAC | AGG | SEQ ID NO: 3 |
|  | Sp20-hRPE65-E02-#04 | TCACAGCTCATGTAACAGGT | TGG | SEQ ID NO: 4 |
| Exon3 | Sp20-hRPE65-E03-#01 | GGAGACTGCCGGTGAGCCAG | AGG | SEQ ID NO: 5 |
|  | Sp20-hRPE65-E03-#02 | ACCGGCAGTCTCCTTCGATG | TGG | SEQ ID NO: 6 |
|  | Sp20-hRPE65-E03-#03 | AGTCTCCTTCGATGTGGGCC | AGG | SEQ ID NO: 7 |
|  | Sp20-hRPE65-E03-#04 | AGAGTCCTGGCCCACATCGA | AGG | SEQ ID NO: 8 |
|  | Sp20-hRPE65-E03-#05 | GGGCTTGCCCATCAAACAGG | TGG | SEQ ID NO: 9 |
|  | Sp20-hRPE65-E03-#06 | TAAAGTCAAACTTGTGCAGG | AGG | SEQ ID NO: 10 |
| Exon4 | Sp20-hRPE65-E04-#01 | TCCGCACTGATGCTTACGTA | CGG | SEQ ID NO: 11 |
|  | Sp20-hRPE65-E04-#02 | CCGCACTGATGCTTACGTAC | GGG | SEQ ID NO: 12 |
|  | Sp20-hRPE65-E04-#03 | CCCGTACGTAAGCATCAGTG | CGG | SEQ ID NO: 13 |
|  | Sp20-hRPE65-E04-#04 | TACGGGCAATGACTGAGAAA | AGG | SEQ ID NO: 14 |
|  | Sp20-hRPE65-E04-#05 | AGGATCGTCATAACAGAATT | TGG | SEQ ID NO: 15 |
| Exon5 | Sp20-hRPE65-E05-#01 | CCACTGGGTAGACATTAACA | AGG | SEQ ID NO: 16 |
|  | Sp20-hRPE65-E05-#02 | CGTAGTAATCTTCCCCCACT | GGG | SEQ ID NO: 17 |
|  | Sp20-hRPE65-E05-#03 | GCGTAGTAATCTTCCCCCAC | TGG | SEQ ID NO: 18 |
| Exon6 | Sp20-hRPE65-E06-#01 | GCAACTATGTCTCTGTCAAT | GGG | SEQ ID NO: 19 |
|  | Sp20-hRPE65-E06-#02 | CAACTATGTCTCTGTCAATG | GGG | SEQ ID NO: 20 |
|  | Sp20-hRPE65-E06-#03 | TTCAATGTGGGGGTGAGCAG | TGG | SEQ ID NO: 21 |
|  | Sp20-hRPE65-E06-#04 | CACCCCACATTGAAAATGA | TGG | SEQ ID NO: 22 |
|  | Sp20-hRPE65-E06-#05 | CGGTTCCATCATTTTCAATG | TGG | SEQ ID NO: 23 |
|  | Sp20-hRPE65-E06-#06 | GATGGAACCGTTTACAATAT | TGG | SEQ ID NO: 24 |
| Exon7 | Sp20-hRPE65-E07-#01 | GCTTGAATCGGTCACTGCAG | GGG | SEQ ID NO: 25 |
|  | Sp20-hRPE65-E07-#02 | GAACGTAAGATGGCTTGAAT | CGG | SEQ ID NO: 26 |
|  | Sp20-hRPE65-E07-#03 | AGTTACCTATGAACGTAAGA | TGG | SEQ ID NO: 27 |

TABLE 1-continued

Target sequences of RPE65 gene for SpCas9

| Loci. | Target name | Target(w/o PAM) | PAM | SEQ ID NO |
|---|---|---|---|---|
| Exon8 | Sp20-hRPE65-E08-#01 | TCCCAACTATATCGTTTTTG | TGG | SEQ ID NO: 28 |
|  | Sp20-hRPE65-E08-#02 | TCCACAAAAACGATATAGTT | GGG | SEQ ID NO: 29 |
|  | Sp20-hRPE65-E08-#03 | ATATCTAAGACTTACCCCCA | TGG | SEQ ID NO: 30 |
| Exon10 | Sp20-hRPE65-E10-#01 | TAGCCAATTTACGTGAGAAC | TGG | SEQ ID NO: 31 |
|  | Sp20-hRPE65-E10-#02 | AGCCAATTTACGTGAGAACT | GGG | SEQ ID NO: 32 |
|  | Sp20-hRPE65-E10-#03 | TTCAGGTTGGGGAGCCTTTC | TGG | SEQ ID NO: 33 |
|  | Sp20-hRPE65-E10-#04 | AGGCTCCCCAACCTGAAGTT | AGG | SEQ ID NO: 34 |
|  | Sp20-hRPE65-E10-#05 | GTTACCTTGTCAATATTCAA | AGG | SEQ ID NO: 35 |
| Exon11 | Sp20-hRPE65-E11-#01 | TGTGCAGTGACGAGACTATC | TGG | SEQ ID NO: 36 |
|  | Sp20-hRPE65-E11-#02 | CAGTGACGAGACTATCTGGC | TGG | SEQ ID NO: 37 |
| Exon12 | Sp20-hRPE65-E12-#01 | ATCAATTACCAGAAGTATTG | TGG | SEQ ID NO: 38 |
|  | Sp20-hRPE65-E12-#02 | AAACCTTACACATATGCGTA | TGG | SEQ ID NO: 39 |
|  | Sp20-hRPE65-E12-#03 | AGTCCATACGCATATGTGTA | AGG | SEQ ID NO: 40 |
|  | Sp20-hRPE65-E12-#04 | TACACATATGCGTATGGACT | TGG | SEQ ID NO: 41 |
|  | Sp20-hRPE65-E12-#05 | GAAGGATTAATTACCCTATC | TGG | SEQ ID NO: 42 |
| Exon14 | Sp20-hRPE65-E14-#01 | TGAAGTTGCCCGGGCTGAAG | TGG | SEQ ID NO: 43 |
|  | Sp20-hRPE65-E14-#02 | GTTAATCTCCACTTCAGCCC | GGG | SEQ ID NO: 44 |

TABLE 2

Target sequences of RPE65 gene for CjCas9

| Loci. | Target name | Target(w/o PAM) | PAM | SEQ ID NO |
|---|---|---|---|---|
| Exon3 | Cj22-hRPE65-E03-#01 | CACCTGTTTGATGGGCAAGCCC | TCCTGCAC | SEQ ID NO: 45 |
|  | Cj22-hRPE65-E03-#02 | TTTGACTTTAAAGAAGGACATG | TCACATAC | SEQ ID NO: 46 |
| Exon4 | Cj22-hRPE65-E04-#01 | TGTTTCAATGTCCTTCAGGTTC | ATCCGCAC | SEQ ID NO: 47 |
|  | Cj22-hRPE65-E04-#02 | TCAGGTTCATCCGCACTGATGC | TTACGTAC | SEQ ID NO: 48 |
|  | Cj22-hRPE65-E04-#03 | GACGATCCTTTTCTCAGTCATT | GCCCGTAC | SEQ ID NO: 49 |
|  | Cj22-hRPE65-E04-#04 | GAAAAGGATCGTCATAACAGAA | TTTGGCAC | SEQ ID NO: 50 |
|  | Cj22-hRPE65-E04-#05 | ATATATTCTTGCAGGGATCTGG | GAAAGCAC | SEQ ID NO: 51 |
| Exon5 | Cj22-hRPE65-E05-#01 | CCCAGTGGGGAAGATTACTAC | GCTTGCAC | SEQ ID NO: 52 |
| Exon7 | Cj22-hRPE65-E07-#01 | ATCCAATAAGCAAGTCAGAGAT | CGTTGTAC | SEQ ID NO: 53 |
|  | Cj22-hRPE65-E07-#02 | CTTGAATCGGTCACTGCAGGGG | AATTGTAC | SEQ ID NO: 54 |

TABLE 2-continued

Target sequences of RPE65 gene for CjCas9

| Loci. | Target name | Target(w/o PAM) | PAM | SEQ ID NO |
|---|---|---|---|---|
| Exon8 | Cj22-hRPE65-E08-#01 | CTCCCAACTATATCGTTTTTGT | GGAGACAC | SEQ ID NO: 55 |
| Exon9 | Cj22-hRPE65-E09-#01 | CATATTGCTGACAAAAAAGGA | AAAAGTAC | SEQ ID NO: 56 |
|  | Cj22-hRPE65-E09-#02 | GGAGAAGTTCTGTATTTATTAT | TGAGGTAC | SEQ ID NO: 57 |
|  | Cj22-hRPE65-E09-#03 | TCCTTTCAACCTCTTCCATCAC | ATCAACAC | SEQ ID NO: 58 |
| Exon10 | Cj22-hRPE65-E10-#01 | CTCCCCAACCTGAAGTTAGGAG | ATATGTAC | SEQ ID NO: 59 |
|  | Cj22-hRPE65-E10-#02 | GGTTACCTTGTCAATATTCAAA | GGAAGTAC | SEQ ID NO: 60 |
| Exon11 | Cj22-hRPE65-E11-#01 | AGGCAAGAATTTAGTCACGCTC | CCCAATAC | SEQ ID NO: 61 |
|  | Cj22-hRPE65-E11-#02 | GGCTCCAGCCAGATAGTCTCGT | CACTGCAC | SEQ ID NO: 62 |
| Exon12 | Cj22-hRPE65-E12-#01 | TTACCAGAAGTATTGTGGGAAA | CCTTACAC | SEQ ID NO: 63 |
|  | Cj22-hRPE65-E12-#02 | TACGCATATGTGTAAGGTTTCC | CACAATAC | SEQ ID NO: 64 |
|  | Cj22-hRPE65-E12-#03 | GGAACAAAGTGATTCAAGCCAA | GTCCATAC | SEQ ID NO: 65 |
| Exon13 | Cj22-hRPE65-E13-#01 | ACTTGGGTTTGGCAAGAGCCTG | ATTCATAC | SEQ ID NO: 66 |
| Exon14 | Cj22-hRPE65-E14-#01 | CTGGGCTCACCACCACACTCAG | AACTACAC | SEQ ID NO: 67 |
|  | Cj22-hRPE65-E14-#02 | TTTGTCCTGCTCCTGGGCTCAC | CACCACAC | SEQ ID NO: 68 |
|  | Cj22-hRPE65-E14-#03 | CATGGACTGTTCAAAAAATCTT | GAGCATAC | SEQ ID NO: 69 |

One Aspect of the Disclosure of the Present Specification Relates to a Composition for Gene Manipulation for Artificially Manipulating or Correcting a Retinal Function-Forming Gene.

The composition for gene manipulation may be used in the generation of an artificially manipulated or corrected retinal function-forming gene. In addition, the retinal function-forming gene artificially manipulated or corrected by the composition for gene manipulation may regulate a retinal function-forming system.

The "artificially manipulated (artificially modified or engineered or artificially engineered)" refers to an artificially modified or manipulated state, rather than a naturally-occurring state. Hereinafter, an unnatural artificially manipulated or modified retinal function-forming gene may be used interchangeably with an artificial retinal function-forming gene.

The term "artificially corrected" refers to a state of artificially correcting a naturally occurring mutation of a gene with an artificially modified state, rather than a naturally-occurring state. Here, the correction may be a correction to a normal sequence of a wild-type gene corresponding to a mutant sequence of a naturally-occurring gene or a modification of the expression of a protein modified by a mutation of a gene to the expression of a normal protein. Alternatively, the correction may be a modification that allows the abnormal expression of a protein due to a mutation of a naturally-occurring gene to be normally expressed.

The "retinal function-forming system" includes all phenomena affecting the formation of a retinal function by the functional modification of an artificially manipulated retinal function-forming gene, and all materials, compositions, methods and uses directly or indirectly involved in the retinal function-forming system. Each element constituting the retinal function-forming system is commonly referred to a "retinal function-forming regulatory element."

The composition for gene manipulation disclosed in the present specification may include a guide nucleic acid and an editor protein.

The composition for gene manipulation may include
(a) a guide nucleic acid capable of targeting a target sequence of a retinal function-forming gene or a nucleic acid sequence encoding the same; and
(b) one or more editor proteins or nucleic acid sequence(s) encoding the same.

The description related to the retinal function-forming gene is the same as described above.

The description related to the target sequence is the same as described above.

The composition for gene manipulation may include a guide nucleic acid-editor protein complex.

The term "guide nucleic acid-editor protein complex" refers to a complex formed through the interaction between a guide nucleic acid and an editor protein.

A description related to the guide nucleic acid is as described above.

The term "editor protein" refers to a peptide, polypeptide or protein which is able to directly bind to or interact with, without direct binding to, a nucleic acid.

Here, the nucleic acid may be a nucleic acid included in a target nucleic acid, gene or chromosome.

Here, the nucleic acid may be a guide nucleic acid.

The editor protein may be an enzyme.

Here, the term "enzyme" refers to a polypeptide or protein that contains a domain capable of cleaving a nucleic acid, gene or chromosome.

The enzyme may be a nuclease or restriction enzyme.

The editor protein may include a complete active enzyme.

Here, the "complete active enzyme" refers to an enzyme having the same function as the nucleic acid, gene or chromosome cleavage function of a wild-type enzyme. For example, the wild-type enzyme that cleaves double-stranded DNA may be a complete active enzyme that entirely cleaves double-stranded DNA. As another example, when the wild-type enzyme cleaving double-stranded DNA undergoes a deletion or substitution of a partial sequence of an amino acids sequence due to artificial engineering, the artificially engineered enzyme variant cleaves double-stranded DNA like the wild-type enzyme, the artificially engineered enzyme variant may be a complete active enzyme.

In addition, the complete active enzyme may include an enzyme having an improved function, compared to the wild-type enzyme. For example, a specific modified or manipulated form of the wild-type enzyme cleaving double-stranded DNA may have a complete enzyme activity, which is greater than the wild-type enzyme, that is, an increased activity of cleaving double-stranded DNA.

The editor protein may include an incomplete or partially active enzyme.

Here, the "incomplete or partially active enzyme" refers to an enzyme having some of the nucleic acid, gene or chromosome cleavage function of the wild-type enzyme. For example, a specific modified or manipulated form of the wild-type enzyme that cleaves double-stranded DNA may be a form having a first function or a form having a second function. Here, the first function is a function of cleaving the first strand of double-stranded DNA, and the second function may be a function of cleaving the second strand of double-stranded DNA. Here, the enzyme with the first function or the enzyme with the second function may be an incomplete or partially active enzyme.

The editor protein may include an inactive enzyme.

Here, the "inactive enzyme" refers to an enzyme in which the nucleic acid, gene or chromosome cleavage function of the wild-type enzyme is entirely inactivated. For example, a specific modified or manipulated form of the wild-type enzyme may be a form in which both of the first and second functions are lost, that is, both of the first function of cleaving the first strand of double-stranded DNA and the second function of cleaving the second strand thereof are lost. Here, the enzyme in which all of the first and second functions are lost may be inactive enzyme.

The editor protein may be a fusion protein.

Here, the term "fusion protein" refers to a protein produced by fusing an enzyme with an additional domain, peptide, polypeptide or protein.

The additional domain, peptide, polypeptide or protein may be a functional domain, peptide, polypeptide or protein, which has a function the same as or different from the enzyme.

The fusion protein may be a form in which the functional domain, peptide, polypeptide or protein is added to one or more of the amino end of an enzyme or the proximity thereof; the carboxyl end of the enzyme or the proximity thereof; the middle part of the enzyme; or a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase. The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV (SEQ ID NO: 241); NLS derived from nucleoplasmin (e.g., nucleoplasmin bipartite NLS with a sequence KRPAATKKAGQAKKKK (SEQ ID NO: 242)); c-myc NLS with an amino acid sequence PAAKRVKLD (SEQ ID NO: 243) or RQRRNELKRSP (SEQ ID NO: 244); hRNPA1 M9 NLS with a sequence NQSSNFGPMKGGNFGGRSSGPYGGGGQYFAKPRNQGGY (SEQ ID NO: 245); an importin-α-derived IBB domain sequence RMRIZFKNKGKDTAELRRRRVEVSVELRKAKKDEQILKRRNV (SEQ ID NO: 246); myoma T protein sequences VSRKRPRP (SEQ ID NO: 247) and PPK- KARED (SEQ ID NO: 248); human p53 sequence PQPKKKPL (SEQ ID NO: 249); a mouse c-abl IV sequence SALIKKKKKMAP (SEQ ID NO: 250); influenza virus NS1 sequences DRLRR (SEQ ID NO: 251) and PKQKKRK (SEQ ID NO: 252); a hepatitis virus-δ antigen sequence RKLKKKIKKL (SEQ ID NO: 253); a mouse Mx1 protein sequence REKKKFLKRR (SEQ ID NO: 254); a human poly(ADP-ribose) polymerase sequence KRKGDEVDGVDEVAKKKSKK (SEQ ID NO: 255); or steroid hormone receptor (human) glucocorticoid sequence RKCLQAGMNLEARKTKK (SEQ ID NO: 256), but the present invention is not limited thereto.

The additional domain, peptide, polypeptide or protein may be a non-functional domain, peptide, polypeptide or protein that does not perform a specific function. Here, the non-functional domain, peptide, polypeptide or protein may be a domain, peptide, polypeptide or protein that does not affect the enzyme function.

The fusion protein may be a form in which the non-functional domain, peptide, polypeptide or protein is added to one or more of the amino end of an enzyme or the proximity thereof; the carboxyl end of the enzyme or the proximity thereof; the middle part of the enzyme; or a combination thereof.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

Alternatively, the modification may be substitution, removal, addition of some nucleotides in the nucleotide sequence encoding the editor protein, or a combination thereof.

In addition, optionally, the composition for gene manipulation may further include a donor having a desired specific nucleotide sequence, which is to be inserted, or a nucleic acid sequence encoding the same.

Here, the nucleic acid sequence to be inserted may be a partial nucleotide sequence of the retinal function-forming gene.

Here, the nucleic acid sequence to be inserted may be a nucleic acid sequence used to correct a mutation of the retinal function-forming gene to be manipulated or introduce a mutation into the retinal function-forming gene.

The term "donor" refers to a nucleotide sequence that helps homologous recombination (HR)-based repair of a damaged gene or nucleic acid.

The donor may be a double- or single-stranded nucleic acid.

The donor may be present in a linear or circular shape.

The donor may include a nucleotide sequence having homology with a target gene or a nucleic acid.

For example, the donor may include a nucleotide sequence having homology with each of nucleotide sequences at a location into which a specific nucleotide sequence is to be inserted, for example, upstream (left) and downstream (right) of a damaged nucleic acid. Here, the specific nucleotide sequence to be inserted may be located between a nucleotide sequence having homology with a nucleotide sequence downstream of the damaged nucleic acid and a nucleotide sequence having homology with a nucleotide sequence upstream of the damaged nucleic acid. Here, the nucleotide sequence having homology may have at least 50%, 55%, 60%, 65%, 70%, 75%, 80%, 85%, 90% or 95% or more homology or complete homology.

The donor may include a specific nucleic acid sequence.

Here, the specific nucleic acid sequence may be a partial nucleotide sequence or partial analogous nucleotide sequence of a target gene. The partial nucleotide sequence of the target gene may include, for example, a normal nucleic acid sequence in which a mutation for correcting a target gene having a mutation is corrected. Alternatively, the partial analogous nucleotide sequence of the target gene may include a mutagenic nucleic acid sequence in which a part of the normal nucleic acid sequence of a target gene for mutating a normal target gene is partially modified.

In one example, when a gene having a mutation with a termination codon in an exon is a target gene, the specific nucleic acid may be a normal nucleotide sequence capable of correcting the termination codon in the exon with a normal nucleotide sequence. In another example, when the expression of a target gene into a protein is to be suppressed, the specific nucleic acid may be a termination codon to be inserted into an exon of the target gene, and in this case, the expression of the target gene may be inhibited due to a termination codon inserted into the exon of the target gene using a composition for gene manipulation including a donor.

Here, the specific nucleic acid sequence may be a termination codon.

Here, the specific nucleic acid sequence may be an exogenous nucleic acid sequence. For example, the exogenous nucleic acid sequence may be an exogenous gene to be expressed in cells having a target gene.

Here, the specific nucleic acid sequence may be a nucleic acid sequence to be expressed in cells having a target gene. For example, the nucleic acid sequence may be a specific gene expressed in cells having a target gene, and in this case, the specific gene may be increased in copy number in cells due to a composition for gene manipulation including a donor.

The donor may selectively include an additional nucleotide sequence. Here, the additional nucleic acid sequence may play a role in increasing stability, insertion efficiency into a target or homologous recombination efficiency of the donor.

For example, the additional nucleotide sequence may be a nucleic acid sequence rich in nucleotides A and T, that is, an A-T rich domain. For example, the additional nucleotide sequence may be a scaffold/matrix attachment region (SMAR).

The guide nucleic acid, editor protein or guide nucleic acid-editor protein complex disclosed in the specification may be delivered or introduced into a subject in various ways.

Here, the term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target gene or chromosome of a guide nucleic acid-editor protein complex.

The organism may be an animal, animal tissue or an animal cell.

The organism may be a human, human tissue or a human cell.

The tissue may be eyeball, skin, liver, kidney, heart, lung, brain, muscle tissue, or blood.

The cell may be a retinal cell, a nerve cell, a glial cell, a cone cell, a rod cell, a retinal pigment epithelium cell (RPE cell) or a stem cell.

The specimen or sample may be acquired from an organism including a target gene or chromosome and may be saliva, blood, retinal tissue, brain tissue, a retinal cell, a nerve cell, a glial cell, a cone cell, a rod cell, a retinal pigment epithelium cell (RPE cell) or a stem cell.

Preferably, the subject may be an organism including a retinal function-forming gene.

The guide nucleic acid, editor protein or guide nucleic acid-editor protein complex may be delivered or introduced into a subject in the form of DNA, RNA or a mixed form.

Here, the guide nucleic acid and/or editor protein may be delivered or introduced into a subject in the form of DNA, RNA or a mixed form by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

In one exemplary embodiment, the nucleic acid sequence encoding the guide nucleic acid and/or editor protein may be delivered or introduced into a subject by a vector.

The vector may include a nucleic acid sequence encoding a guide nucleic acid and/or editor protein.

In one example, the vector may simultaneously include nucleic acid sequences, which encode the guide nucleic acid and the editor protein, respectively.

In another example, the vector may include the nucleic acid sequence encoding the guide nucleic acid.

As an example, domains included in the guide nucleic acid may be contained all in one vector, or may be divided and then contained in different vectors.

In another example, the vector may include the nucleic acid sequence encoding the editor protein.

As an example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

In another exemplary embodiment, the nucleic acid sequence encoding the guide nucleic acid and/or editor protein may be delivered or introduced into a subject by a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, gene gun, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

In one example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nano-vesicle for transferring a protein and RNA, which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-transparent. While the liposome may be made from several different types of lipids; phospholipids are most generally used to produce the liposome as a drug carrier.

In addition, the composition for delivery of the non-vector may be include other additives.

The editor protein may be delivered or introduced into a subject in the form of a peptide, polypeptide or protein.

The editor protein may be delivered or introduced into a subject in the form of a peptide, polypeptide or protein by a method known in the art.

The peptide, polypeptide or protein form may be delivered or introduced into a subject by electroporation, micro-injection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

The guide nucleic acid and the editor protein may be delivered or introduced into a subject in the form of mixing a nucleic acid and a protein.

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

The guide nucleic acid-editor protein complex disclosed in the specification may modify a target nucleic acid, gene or chromosome.

For example, the guide nucleic acid-editor protein complex induces a modification in the sequence of a target nucleic acid, gene or chromosome. As a result, a protein expressed by the target nucleic acid, gene or chromosome may be modified in structure and/or function, or the expression of the protein may be controlled or inhibited.

The guide nucleic acid-editor protein complex may act at the DNA, RNA, gene or chromosome level.

In one example, the guide nucleic acid-editor protein complex may manipulate or modify the transcriptional regulatory region of a target gene to control (e.g., suppress, inhibit, reduce, increase or promote) the expression of a protein encoded by a target gene, or express a protein whose activity is controlled (e.g., suppressed, inhibited, reduced, increased or promoted) or modified.

The guide nucleic acid-editor protein complex may act at the transcription and translation stage of a gene.

In one example, the guide nucleic acid-editor protein complex may promote or inhibit the transcription of a target gene, thereby controlling (e.g., suppressing, inhibiting, reducing, increasing or promoting) the expression of a protein encoded by the target gene.

In another example, the guide nucleic acid-editor protein complex may promote or inhibit the translation of a target gene, thereby controlling (e.g., suppressing, inhibiting, reducing, increasing or promoting) the expression of a protein encoded by the target gene.

In One Embodiment of the Disclosure of the Present Specification, the Composition for Gene Manipulation May Include gRNA and a CRISPR Enzyme.

The composition for gene manipulation may include
(a) a gRNA capable of targeting a target sequence of a retinal function-forming gene or a nucleic acid sequence encoding the same; and
(b) one or more CRISPR enzymes or nucleic acid sequence(s) encoding the same.

The description related to the retinal function-forming gene is the same as described above.

The description related to the target sequence is the same as described above.

The composition for gene manipulation may include a gRNA-CRISPR enzyme complex.

The term "gRNA-CRISPR enzyme complex" refers to a complex formed by the interaction between gRNA and a CRISPR enzyme.

A description related to the gRNA is as described above.

The term "CRISPR enzyme" is a main protein component of a CRISPR-Cas system, and forms a complex with gRNA, resulting in the CRISPR-Cas system.

The CRISPR enzyme may be a nucleic acid having a sequence encoding the CRISPR enzyme or a polypeptide (or a protein).

The CRISPR enzyme may be a Type II CRISPR enzyme.

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes a RuvC domain, an HNH domain and a PAM-interaction (PI) domain. Here, the RuvC domain encompasses RuvC-like domains, and the HNH domain encompasses HNH-like domains.

Here, the RuvC domain shares structural similarity with members of the microorganism family existing in nature having the type II CRISPR enzyme, and cleaves a single strand, for example, a non-complementary strand of a nucleic acid in the transcriptional regulatory region of a target gene, that is, a strand not forming a complementary bond with gRNA. The RuvC domain is sometimes referred to as a RuvCI domain, RuvCII domain or RuvCIII domain in the art, and generally called an RuvC I, RuvCII or RuvCIII.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs.

The PI domain recognizes a specific nucleotide sequence in the transcriptional regulatory region of a target gene, that is, a protospacer adjacent motif (PAM), or interacts with PAM. Here, the PAM may vary according to the origin of a Type II CRISPR enzyme. For example, when the CRISPR enzyme is SpCas9, the PAM may be 5'-NGG-3', and when the CRISPR enzyme is *Streptococcus thermophilus* Cas9 (StCas9), the PAM may be 5'-NNAGAAW-3' (W=A or T), when the CRISPR enzyme is *Neisseria meningitidis* Cas9 (NmCas9), the PAM may be 5'-NNNNGATT-3', and when the CRISPR enzyme is *Campylobacter jejuni* Cas9 (CjCas9), the PAM may be 5'-NNNVRYAC-3' (V=G or C or A, R=A or G, Y=C or T), herein, N is A, T, G or C; or A, U, G or C). However, while it is generally understood that PAM is determined according to the origin of the above-described enzyme, as the study of a mutant of an enzyme derived from the corresponding origin progresses, the PAM may be changed.

The Type II CRISPR enzyme may be Cas9.

The Cas9 may be derived from various microorganisms such as *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus* and *Acaryochloris marina*.

The Cas9 is an enzyme which binds to gRNA so as to cleave or modify a target sequence or position on the transcriptional regulatory region of a target gene, and may consist of an HNH domain capable of cleaving a nucleic acid strand forming a complementary bond with gRNA, an RuvC domain capable of cleaving a nucleic acid strand forming a non-complementary bond with gRNA, an REC domain interacting the target and a PI domain recognizing a PAM. Hiroshi Nishimasu et al. (2014) Cell 156:935-949 may be referenced for specific structural characteristics of Cas9.

The Cas9 may be isolated from a microorganism existing in nature or non-naturally produced by a recombinant or synthetic method.

In addition, the CRISPR enzyme may be a Type V CRISPR enzyme.

The type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a nucleic acid in the transcriptional regulatory region of a target gene is dependent on the PAM sequence.

The PAM sequence may be a sequence present in the transcriptional regulatory region of a target gene, and recognized by the PI domain of a Type V CRISPR enzyme. The PAM sequence may have different sequences according to the origin of the Type V CRISPR enzyme. That is, each species has a specifically recognizable PAM sequence. For example, the PAM sequence recognized by Cpf1 may be 5'-TTN-3' (N is A, T, C or G). While it has been generally understood that PAM is determined according to the origin of the above-described enzyme, as the study of mutants of the enzyme derived from the corresponding origin progresses, the PAM may be changed.

The Type V CRISPR enzyme may be Cpf1.

The Cpf1 may be derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacillus, Methylobacterium* or *Acidaminococcus*.

The Cpf1 may consist of a RuvC-like domain corresponding to the RuvC domain of Cas9, an Nuc domain instead of the HNH domain of Cas9, an REC and WED domains recognizing a target, and a PI domain recognizing PAM. For specific structural characteristics of Cpf1, Takashi Yamano et al. (2016) Cell 165:949-962 may be referenced.

The Cpf1 may be isolated from a microorganism existing in nature or non-naturally produced by a recombinant or synthetic method.

The CRISPR enzyme may be a nuclease or restriction enzyme having a function of cleaving a double-stranded nucleic acid in the transcriptional regulatory region of a target gene.

The CRISPR enzyme may be a complete active CRISPR enzyme.

The term "complete active" refers to a state in which an enzyme has the same function as that of a wild-type CRISPR enzyme, and the CRISPR enzyme in such a state is named a complete active CRISPR enzyme. Here, the "function of the wild-type CRISPR enzyme" refers to a state in which an enzyme has functions of cleaving double-stranded DNA, that is, the first function of cleaving the first strand of double-stranded DNA and a second function of cleaving the second strand of double-stranded DNA.

The complete active CRISPR enzyme may be a wild-type CRISPR enzyme that cleaves double-stranded DNA.

The complete active CRISPR enzyme may be a CRISPR enzyme variant formed by modifying or manipulating the wild-type CRISPR enzyme that cleaves double-stranded DNA.

The CRISPR enzyme variant may be an enzyme in which one or more amino acids of the amino acid sequence of the wild-type CRISPR enzyme are substituted with other amino acids, or one or more amino acids are removed.

The CRISPR enzyme variant may be an enzyme in which one or more amino acids are added to the amino acid sequence of the wild-type CRISPR enzyme. Here, the location of the added amino acids may be the N-end, the C-end or the amino acid sequence of the wild-type enzyme.

The CRISPR enzyme variant may be a complete active enzyme with an improved function compared to the wild-type CRISPR enzyme.

For example, a specifically modified or manipulated form of the wild-type CRISPR enzyme, that is, the CRISPR enzyme variant may cleave double-stranded DNA while not binding to the double-stranded DNA to be cleaved or maintaining a certain distance therefrom. In this case, the modified or manipulated form may be a complete active CRISPR enzyme with an improved functional activity, compared to the wild-type CRISPR enzyme.

The CRISPR enzyme variant may be a complete active CRISPR enzyme with a reduced function, compared to the wild-type CRISPR enzyme.

For example, the specific modified or manipulated form of the wild-type CRISPR enzyme, that is, the CRISPR enzyme variant may cleave double-stranded DNA while very close to the double-stranded DNA to be cleaved or forming a specific bond therewith. Here, the specific bond may be, for example, a bond between an amino acid at a specific region of the CRISPR enzyme and a DNA sequence at the cleavage location. In this case, the modified or manipulated form may be a complete active CRISPR enzyme with a reduced functional activity, compared to the wild-type CRISPR enzyme.

The CRISPR enzyme may be an incomplete or partially active CRISPR enzyme.

The term "incomplete or partially active" refers to a state in which an enzyme has one selected from the functions of the wild-type CRISPR enzyme, that is, a first function of cleaving the first strand of double-stranded DNA and a second function of cleaving the second strand of double-stranded DNA. The CRISPR enzyme in this state is named an incomplete or partially active CRISPR enzyme. In addition, the incomplete or partially active CRISPR enzyme may be referred to as a nickase.

The term "nickase" refers to a CRISPR enzyme manipulated or modified to cleave only one strand of the double strand of a nucleic acid in the transcriptional regulatory region of a target gene, and the nickase has nuclease activity of cleaving a single strand, for example, a strand that is complementary or non-complementary to gRNA of a nucleic acid in the transcriptional regulatory region of a target gene. Therefore, to cleave the double strand, nuclease activity of the two nickases is needed.

The nickase may have nuclease activity by the RuvC domain. That is, the nickase may not include nuclease activity of the HNH domain, and to this end, the HNH domain may be manipulated or modified.

In one example, when the CRISPR enzyme is a Type II CRISPR enzyme, the nickase may be a Type II CRISPR enzyme including a modified HNH domain.

For example, provided that the Type II CRISPR enzyme is a wild-type SpCas9, the nickase may be a SpCas9 variant in which nuclease activity of the HNH domain is inactivated by mutation that the 840th amino acid in the amino acid sequence of the wild-type SpCas9 is mutated from histidine to alanine. Since the nickase produced thereby, that is, the SpCas9 variant has nuclease activity of the RuvC domain, it is able to cleave a strand which is a non-complementary strand of a nucleic acid in the transcriptional regulatory region of a target gene, that is, a strand not forming a complementary bond with gRNA.

For another example, provided that the Type II CRISPR enzyme is a wild-type CjCas9, the nickase may be a CjCas9 variant in which nuclease activity of the HNH domain is inactivated by mutation that the 559th amino acid in the amino acid sequence of the wild-type CjCas9 is mutated from histidine to alanine. Since the nickase produced thereby, that is, the CjCas9 variant has nuclease activity of the RuvC domain, it is able to cleave a strand which is a non-complementary strand of a nucleic acid in the transcriptional regulatory region of a target gene, that is, a strand not forming a complementary bond with gRNA.

In addition, the nickase may have nuclease activity by the HNH domain of a CRISPR enzyme. That is, the nickase may not include the nuclease activity of the RuvC domain, and to this end, the RuvC domain may be manipulated or modified.

In one example, when the CRISPR enzyme is a Type II CRISPR enzyme, the nickase may be a Type II CRISPR enzyme including a modified RuvC domain.

For example, provided that the Type II CRISPR enzyme is a wild-type SpCas9, the nickase may be a SpCas9 variant in which nuclease activity of the RuvC domain is inactivated by mutation that the 10th amino acid in the amino acid sequence of the wild-type SpCas9 is mutated from aspartic acid to alanine. Since the nickase produced thereby, that is the SpCas9 variant has nuclease activity of the HNH domain, it is able to cleave a strand which is a complementary strand of a nucleic acid in the transcriptional regulatory region of a target gene, that is, a strand forming a complementary bond with gRNA.

For another example, provided that the Type II CRISPR enzyme is a wild-type CjCas9, the nickase may be a CjCas9 variant in which nuclease activity of the RuvC domain is inactivated by mutation that the 8th amino acid in the amino acid sequence of the wild-type CjCas9 is mutated from aspartic acid to alanine. Since the nickase produced thereby, that is, the CjCas9 variant has nuclease activity of the HNH domain, it is able to cleave a strand which is a complementary strand of a nucleic acid in the transcriptional regulatory region of a target gene, that is, a strand forming a complementary bond with gRNA.

The CRISPR enzyme may be an inactive CRISPR enzyme.

The term "inactive" refers to a state in which both of the functions of the wild-type CRISPR enzyme, that is, the first function of cleaving the first strand of double-stranded DNA and the second function of cleaving the second strand of double-stranded DNA are lost. The CRISPR enzyme in such a state is named an inactive CRISPR enzyme.

The inactive CRISPR enzyme may have nuclease inactivity due to variations in the domain having nuclease activity of a wild-type CRISPR enzyme.

The inactive CRISPR enzyme may have nuclease inactivity due to variations in a RuvC domain and an HNH domain. That is, the inactive CRISPR enzyme may not have nuclease activity generated by the RuvC domain and HNH domain of the CRISPR enzyme, and to this end, the RuvC domain and the HNH domain may be manipulated or modified.

In one example, when the CRISPR enzyme is a Type II CRISPR enzyme, the inactive CRISPR enzyme may be a Type II CRISPR enzyme having a modified RuvC domain and HNH domain.

For example, when the Type II CRISPR enzyme is a wild-type SpCas9, the inactive CRISPR enzyme may be a SpCas9 variant in which the nuclease activities of the RuvC domain and the HNH domain are inactivated by mutations of both aspartic acid 10 and histidine 840 in the amino acid sequence of the wild-type SpCas9 to alanine. Here, since, in the produced inactive CRISPR enzyme, that is, the SpCas9 variant, the nuclease activities of the RuvC domain and the HNH domain are inactivated, a double-stranded nucleic acid in the transcriptional regulatory region of a target gene may be entirely cleaved.

In another example, when the Type II CRISPR enzyme is a wild-type CjCas9, the inactive CRISPR enzyme may be a CjCas9 variant in which the nuclease activities of the RuvC domain and the HNH domain are inactivated by mutations of both aspartic acid 8 and histidine 559 in the amino acid sequence of the wild-type CjCas9 to alanine. Here, since, in the produced inactive CRISPR enzyme, that is, the CjCas9 variant, the nuclease activities of the RuvC domain and HNH domain are inactivated, a double-stranded nucleic acid in the transcriptional regulatory region of a target gene may not be entirely cleaved.

The CRISPR enzyme may have helicase activity, that is, an ability to anneal the helix structure of the double-stranded nucleic acid, in addition to the above-described nuclease activity.

In addition, the CRISPR enzyme may be modified to complete activate, incomplete or partially activate, or inactivate the helicase activity.

The CRISPR enzyme may be a CRISPR enzyme variant produced by artificially manipulating or modifying the wild-type CRISPR enzyme.

The CRISPR enzyme variant may be an artificially manipulated or modified CRISPR enzyme variant for modifying the functions of the wild-type CRISPR enzyme, that is, the first function of cleaving the first strand of double-stranded DNA and/or the second function of cleaving the second strand of double-stranded DNA.

For example, the CRISPR enzyme variant may be a form in which the first function of the functions of the wild-type CRISPR enzyme is lost.

Alternatively, the CRISPR enzyme variant may be a form in which the second function of the functions of the wild-type CRISPR enzyme is lost.

For example, the CRISPR enzyme variant may be a form in which both of the functions of the wild-type CRISPR enzyme, that is, the first function and the second function, are lost.

The CRISPR enzyme variant may form a gRNA-CRISPR enzyme complex by interactions with gRNA.

The CRISPR enzyme variant may be an artificially manipulated or modified CRISPR enzyme variant for modifying a function of interacting with gRNA of the wild-type CRISPR enzyme.

For example, the CRISPR enzyme variant may be a form having reduced interactions with gRNA, compared to the wild-type CRISPR enzyme.

Alternatively, the CRISPR enzyme variant may be a form having increased interactions with gRNA, compared to the wild-type CRISPR enzyme.

For example, the CRISPR enzyme variant may be a form having the first function of the wild-type CRISPR enzyme and reduced interactions with gRNA.

Alternatively, the CRISPR enzyme variant may be a form having the first function of the wild-type CRISPR enzyme and increased interactions with gRNA.

For example, the CRISPR enzyme variant may be a form having the second function of the wild-type CRISPR enzyme and reduced interactions with gRNA.

Alternatively, the CRISPR enzyme variant may be a form having the second function of the wild-type CRISPR enzyme and increased interactions with gRNA.

For example, the CRISPR enzyme variant may be a form not having the first and second functions of the wild-type CRISPR enzyme, and having reduced interactions with gRNA.

Alternatively, the CRISPR enzyme variant may be a form not having the first and second functions of the wild-type CRISPR enzyme and having increased interactions with gRNA.

Here, according to the interaction strength between gRNA and the CRISPR enzyme variant, various gRNA-CRISPR enzyme complexes may be formed, and according to the CRISPR enzyme variant, there may be a difference in function of approaching or cleaving the target sequence.

For example, the gRNA-CRISPR enzyme complex formed by a CRISPR enzyme variant having reduced interactions with gRNA may cleave a double or single strand of a target sequence only when very close to or localized to the target sequence completely complementarily bind to gRNA.

The CRISPR enzyme variant may be in a form in which at least one amino acid of the amino acid sequence of the wild-type CRISPR enzyme is modified.

As an example, the CRISPR enzyme variant may be in a form in which at least one amino acid of the amino acid sequence of the wild-type CRISPR enzyme is substituted.

As another example, the CRISPR enzyme variant may be in a form in which at least one amino acid of the amino acid sequence of the wild-type CRISPR enzyme is deleted.

As still another example, the CRISPR enzyme variant may be in a form in which at least one amino acid of the amino acid sequence of the wild-type CRISPR enzyme is added.

In one example, the CRISPR enzyme variant may be in a form in which at least one amino acid of the amino acid sequence of the wild-type CRISPR enzyme is substituted, deleted and/or added.

In addition, optionally, the CRISPR enzyme variant may further include a functional domain, in addition to the original functions of the wild-type CRISPR enzyme, that is, the first function of cleaving the first strand of double-stranded DNA and the second function of cleaving the second strand thereof. Here, the CRISPR enzyme variant may have an additional function, in addition to the original functions of the wild-type CRISPR enzyme.

The functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

The functional domain may be a deaminase.

For example, cytidine deaminase may be further included as a functional domain to an incomplete or partially-active CRISPR enzyme. In one exemplary embodiment, a fusion protein may be produced by adding a cytidine deaminase, for example, apolipoprotein B editing complex 1 (APOBEC1) to a SpCas9 nickase. The [SpCas9 nickase]-[APOBEC1] formed as described above may be used in nucleotide editing of C to T or U, or nucleotide editing of G to A.

In another example, adenine deaminase may be further included as a functional domain to the incomplete or partially-active CRISPR enzyme. In one exemplary embodiment, a fusion protein may be produced by adding adenine deaminases, for example, TadA variants, ADAR2 variants or ADAT2 variants to a SpCas9 nickase. The [SpCas9 nickase]-[TadA variant], [SpCas9 nickase]-[ADAR2 variant] or [SpCas9 nickase]-[ADAT2 variant] formed as described above may be used in nucleotide editing of A to G, or nucleotide editing of T to C, because the fusion protein modifies nucleotide A to inosine, the modified inosine is recognized as nucleotide G by a polymerase, thereby substantially exhibiting nucleotide editing of A to G.

The functional domain may be a nuclear localization sequence or signal (NLS) or a nuclear export sequence or signal (NES).

In one example, the CRISPR enzyme may include one or more NLSs. Here, one or more NLSs may be included at an N-terminus of a CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 241); NLS from nucleoplasmin (e.g., nucleoplasmin bipartite NLS having the sequence KRPAATKKAGQAKKKK (SEQ ID NO: 242)); c-myc NLS having the amino acid sequence PAAKRVKLD (SEQ ID NO: 243) or RQRRNELKRSP (SEQ ID NO: 244); hRNPA1 M9 NLS having the sequence NQSSNFGPMKGGNFGGRSSGPYGGGGQYFAKPRNQGGY (SEQ ID NO: 245); the sequence RMRIZFKNKGKDTAELRRRRVEVSVELRKAKKDEQILKRRNV (SEQ ID NO: 246) of the IBB domain from importin-α; the sequences VSRKRPRP (SEQ ID NO: 247) and PPKKARED (SEQ ID NO: 248) of a myoma T protein; the sequence PQPKKKPL (SEQ ID NO: 249) of human p53; the sequence SALIKKKKKMAP (SEQ ID NO: 250) of mouse c-abl IV; the sequences DRLRR (SEQ ID NO: 251) and PKQKKRK (SEQ ID NO: 252) of influenza virus NS1; the sequence RKLKKKIKKL (SEQ ID NO: 253) of a hepatitis delta virus antigen; the sequence REKKKFLKRR (SEQ ID NO: 254) of a mouse Mx1 protein; the sequence KRKGDEVDGVDEVAKKKSKK (SEQ ID NO: 255) of a human poly (ADP-ribose) polymerase; or the NLS sequence RKCLQAGMNLEARKTKK (SEQ ID NO: 256), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

The split-type CRISPR enzyme may be a complete, incomplete or partially active enzyme or inactive enzyme.

For example, when the CRISPR enzyme is a SpCas9, the SpCas9 may be divided into two parts between the residue 656, tyrosine, and the residue 657, threonine, thereby generating split SpCas9.

The split-type CRISPR enzyme may selectively include an additional domain, peptide, polypeptide or protein for reconstitution.

The additional domain, peptide, polypeptide or protein for reconstitution may be assembled for formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, when the CRISPR enzyme is a SpCas9, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycin is present, thereby producing a reconstituted CRISPR enzyme.

The CRISPR enzyme or CRISPR enzyme variant disclosed in the specification may be a polypeptide, protein or nucleic acid having a sequence encoding the same, and may be codon-optimized for a subject to introduce the CRISPR enzyme or CRISPR enzyme variant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized for optimal gene expression in a given organism based on codon optimization.

The gRNA, CRISPR enzyme or gRNA-CRISPR enzyme complex disclosed in the specification may be delivered or introduced into a subject by various delivering methods and various forms.

The subject related description is as described above.

In one exemplary embodiment, a nucleic acid sequence encoding the gRNA and/or CRISPR enzyme may be delivered or introduced into a subject by a vector.

The vector may include the nucleic acid sequence encoding the gRNA and/or CRISPR enzyme.

In one example, the vector may simultaneously include the nucleic acid sequences encoding the gRNA and the CRISPR enzyme.

In another example, the vector may include the nucleic acid sequence encoding the gRNA.

For example, domains contained in the gRNA may be contained in one vector, or may be divided and then contained in different vectors.

In another example, the vector may include the nucleic acid sequence encoding the CRISPR enzyme.

For example, in the case of the CRISPR enzyme, the nucleic acid sequence encoding the CRISPR enzyme may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding the gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus. The virus may be a retrovirus, a lentivirus, an adenovirus, adeno-associated virus (AAV), vaccinia virus, a poxvirus or a herpes simplex virus, but the present invention is not limited thereto.

In one example, a nucleic acid sequence encoding gRNA and/or a CRISPR enzyme may be delivered or introduced by a recombinant lentivirus.

In another example, a nucleic acid sequence encoding gRNA and/or a CRISPR enzyme may be delivered or introduced by a recombinant adenovirus. In still another example, a nucleic acid sequence encoding gRNA and/or a CRISPR enzyme may be delivered or introduced by recombinant AAV. In yet another example, a nucleic acid sequence encoding gRNA and/or a CRISPR enzyme may be delivered or introduced by one or more hybrids of hybrid viruses, for example, the viruses described herein.

In one exemplary embodiment, the gRNA-CRISPR enzyme complex may be delivered or introduced into a subject.

For example, the gRNA may be present in the form of DNA, RNA or a mixture thereof. The CRISPR enzyme may be present in the form of a peptide, polypeptide or protein.

In one example, the gRNA and CRISPR enzyme may be delivered or introduced into a subject in the form of a gRNA-CRISPR enzyme complex including RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The gRNA-CRISPR Enzyme Complex Disclosed in the Present Specification May be Used to Artificially Manipulate or Modify a Target Gene, that is, a Retinal Function-Forming Gene.

A target gene may be manipulated or modified using the above-described gRNA-CRISPR enzyme complex, that is, the CRISPR complex. Here, the manipulation or modification of the transcriptional regulatory region of a target gene may include both of i) cleaving or damaging of the transcriptional regulatory region of a target gene and ii) repairing of the damaged transcriptional regulatory region.

The i) cleaving or damaging of the target gene may be cleavage or damage of the target gene using the CRISPR complex, and particularly, cleavage or damage of a target sequence of the target gene.

The target sequence nay become a target of the gRNA-CRISPR enzyme complex, and the target sequence may or may not include a PAM sequence recognized by the CRISPR enzyme. Such a target sequence may provide a critical standard to one who is involved in the designing of gRNA.

The target sequence may be specifically recognized by gRNA of the gRNA-CRISPR enzyme complex, and therefore, the gRNA-CRISPR enzyme complex may be located near the recognized target sequence.

The "cleavage" at a target site refers to the breakage of a covalent backbone of a polynucleotide. The cleavage includes enzymatic or chemical hydrolysis of a phosphodiester bond, but the present invention is not limited thereto. Other than this, the cleavage may be performed by various methods. Both of single strand cleavage and double strand cleavage are possible, wherein the double strand cleavage may result from two distinct single strand cleavages. The double strand cleavage may produce a blunt end or a staggered end (or a sticky end).

In one example, the cleavage or damage of a target gene using the CRISPR complex may be the entire cleavage or damage of the double strand of a target sequence.

In one exemplary embodiment, when the CRISPR enzyme is a wild-type SpCas9, the double strand of a target sequence forming a complementary bond with gRNA may be completely cleaved by the CRISPR complex.

In another exemplary embodiment, when the CRISPR enzymes are SpCas9 nickase (D10A) and SpCas9 nickase (H840A), the two single strands of a target sequence forming a complementary bond with gRNA may be respectively cleaved by the each CRISPR complex. That is, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In another example, the cleavage or damage of a target gene or a nucleic acid using the CRISPR complex may be the cleavage or damage of only a single strand of the double strand of a target sequence. Here, the single strand may be a guide nucleic acid-binding sequence of the target sequence complementarily binding to gRNA, that is, a complementary single strand, or a non-guide nucleic acid-binding sequence not complementarily binding to gRNA, that is, a non-complementary single strand with gRNA.

In one exemplary embodiment, when the CRISPR enzyme is a SpCas9 nickase (D10A), the CRISPR complex may cleave the guide nucleic acid-binding sequence of a target sequence complementarily binding to gRNA, that is, a complementary single strand, by a SpCas9 nickase (D10A), and may not cleave a non-guide nucleic acid-binding sequence not complementarily binding to gRNA, that is, a non-complementary single strand with gRNA.

In another exemplary embodiment, when the CRISPR enzyme is a SpCas9 nickase (H840A), the CRISPR complex may cleave the non-guide nucleic acid-binding sequence of a target sequence not complementarily binding to gRNA, that is, a non-complementary single strand with gRNA by a SpCas9 nickase (H840A), and may not cleave the guide nucleic acid-binding sequence of a target sequence complementarily binding to gRNA, that is, a complementary single strand.

In still another example, the cleavage or damage of a target gene or a nucleic acid using the CRISPR complex may be partial removal of a nucleic acid fragment.

In one exemplary embodiment, when the CRISPR complexes consist of wild-type SpCas9 and two gRNAs having different target sequences, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

The ii) repairing of the damaged target gene may be repairing or restoring performed through non-homologous end joining (NHEJ) and homology-directed repair (HDR).

The non-homologous end joining (NHEJ) is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because mutation in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a target gene in which the expression is controlled by the transcriptional regulatory region targeted by the CRISPR complex may be performed using such NHEJ. A double strand or two single strands of the transcriptional regulatory region of a target gene may be cleaved using the CRISPR enzyme such as Cas9 or Cpf1, and the broken double strand or two single strands may have indels through the NHEJ, thereby inducing specific knockout of the target gene or nucleic acid. Here, the site of a target gene or nucleic acid cleaved by the CRISPR enzyme may be a non-coding or coding region, and in addition, the site of the target gene or nucleic acid restored by NHEJ may be a non-coding or coding region.

In one example, the double strand of a target gene may be cleaved using the CRISPR complex, and various indels (insertions and deletions) may be generated at a repaired region by repairing through NHEJ.

The term "indel" refers to a variation formed by inserting or deleting a partial nucleotide into/from the nucleotide sequence of DNA. Indels may be introduced into the target sequence during repair by HDR or NHEJ, when the gRNA-CRISPR enzyme complex, as described above, cleaves a nucleic acid (DNA, RNA) of a retinal function-forming gene.

The homology directed repairing (HDR) is a correction method without an error, which uses a homologous sequence as a template to repair or restore the damaged transcriptional regulatory region, and generally, to repair or restoration broken DNA, that is, to restore innate information of cells, the broken DNA is repaired using information of a complementary nucleotide sequence which is not modified or information of a sister chromatid. The most common type of HDR is homologous recombination (HR). HDR is a repair or restore method usually occurring in the S or G2/M phase of actively dividing cells.

To repair or restore damaged DNA using HDR, rather than using a complementary nucleotide sequence or sister chromatin of the cells, a DNA template artificially synthesized using information of a complementary nucleotide sequence or homologous nucleotide sequence, that is, a nucleic acid template including a complementary nucleotide sequence or homologous nucleotide sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the target gene or nucleic acid modified by a mutation to a normal gene, or a gene or nucleic acid to be expressed in cells, but the present invention is not limited thereto.

In one example, a double or single strand of a target gene or a nucleic acid may be cleaved using the CRISPR complex, a nucleic acid template including a nucleotide sequence complementary to a nucleotide sequence adjacent to the cleavage site may be provided to cells, and the cleaved nucleotide sequence of the target gene or nucleic acid may be repaired or restored through HDR.

Here, the nucleic acid template including the complementary nucleotide sequence may have a complementary nucleotide sequence of the broken DNA, that is, a cleaved double or single strand, and further include a nucleic acid sequence or nucleic acid fragment to be inserted into the broken DNA. An additional nucleic acid sequence or nucleic acid fragment may be inserted into the broken DNA, that is, a cleaved site of the target gene or nucleic acid using the nucleic acid template including the complementary nucleotide sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting a target gene or a nucleic acid modified by a mutation to a normal gene or nucleic acid, or a gene or nucleic acid to be expressed in cells. The complementary nucleotide sequence may be a nucleotide sequence having complementary bonds with broken DNA, that is, right and left nucleotide sequences of the cleaved double or single strand of the target gene or nucleic acid. Alternatively, the complementary nucleotide sequence may be a nucleotide sequence having complementary bonds with broken DNA, that is, 3' and 5' ends of the cleaved double or single strand of the target gene or nucleic acid. The complementary nucleotide sequence may be a 15 to 3000-nt sequence, a length or size of the complementary nucleotide sequence may be suitably designed according to a size of the nucleic acid template or the target gene or the nucleic acid. Here, the nucleic acid template may be a double- or single-stranded nucleic acid, and may be linear or circular, but the present invention is not limited thereto.

In another example, a double- or single-strand of a target gene or a nucleic acid is cleaved using the CRISPR complex, a nucleic acid template including a homologous nucleotide sequence with a nucleotide sequence adjacent to a cleavage site is provided to cells, and the cleaved nucleotide sequence of the target gene or nucleic acid may be repaired or restored by HDR.

Here, the nucleic acid template including the homologous nucleotide sequence may have a homologous nucleotide sequence of the broken DNA, that is, a cleaved double- or single-strand, and further include a nucleic acid sequence or nucleic acid fragment to be inserted into the broken DNA. An additional nucleic acid sequence or nucleic acid fragment may be inserted into broken DNA, that is, a cleaved site of a target gene or a nucleic acid using the nucleic acid template including a homologous nucleotide sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting the target gene or nucleic acid modified by a mutation to a normal gene or nucleic acid, or a gene or nucleic acid to be expressed in cells. The homologous nucleotide sequence may be a nucleotide sequence having homology with the broken DNA, that is, the right and left nucleotide sequence of the cleaved double-strand of the target gene or nucleic acid. Alternatively, the complementary nucleotide sequence may be a nucleotide sequence having homology with broken DNA, that is, the 3' and 5' ends of a cleaved double or single strand of the target gene or nucleic acid. The homologous nucleotide sequence may be a 15 to 3000-nt sequence, and a length or size of the homologous nucleotide sequence may be suitably designed according to a size of the nucleic acid template or the target gene or the nucleic acid. Here, the nucleic acid template may be a double- or single-stranded nucleic acid, and may be linear or circular, but the present invention is not limited thereto.

Other than the NHEJ and HDR, there are various methods for repairing or restoring a damaged target gene. For example, the method of repairing or restoring a damaged target gene may be single-strand annealing, single-strand break repair, mismatch repair, nucleotide cleavage repair or a method using the nucleotide cleavage repair.

The single-strand annealing (SSA) is a method of repairing double strand breaks between two repeat sequences present in a target nucleic acid, and generally uses a repeat sequence of more than 30 nucleotides. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

The SSA, similar to HDR, utilizes a complementary sequence, that is, a complementary repeat sequence, and in contrast, does not requires a nucleic acid template for modifying or correcting a target nucleic acid sequence.

Single strand breaks in a genome are repaired through a separate mechanism, single-strand break repair (SSBR), from the above-described repair mechanisms. In the case of single-strand DNA breaks, PARP1 and/or PARP2 recognizes the breaks and recruits a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single nucleotide. After DNA gap filling, a DNA ligase promotes end joining.

The mismatch repair (MMR) works on mismatched DNA nucleotides. Each of an MSH2/6 or MSH2/3 complex has ATPase activity and thus plays an important role in recognizing a mismatch and initiating a repair, and the MSH2/6 primarily recognizes nucleotide-nucleotide mismatches and identifies one or two nucleotide mismatches, but the MSH2/3 primarily recognizes a larger mismatch.

The base excision repair (BER) is a repair method which is active throughout the entire cell cycle, and used to remove a small non-helix-distorting base damaged region from the genome. In the damaged DNA, damaged nucleotides are removed by cleaving an N-glycoside bond joining a nucleotide to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary nucleotide, and then an end of the newly-filled complementary nucleotide is ligated with the backbone by a DNA ligase, resulting in repair of the damaged DNA.

The nucleotide excision repair (NER) is an excision mechanism important for removing large helix-distorting damage from DNA, and when the damage is recognized, a short single-strand DNA segment containing the damaged region is removed, resulting in a single strand gap of 22 to 30 nucleotides. The generated gap is filled with a new complementary nucleotide, and an end of the newly filled complementary nucleotide is ligated with the backbone by a DNA ligase, resulting in the repair of the damaged DNA.

Effects of artificially manipulating a target gene, that is, a retinal function-forming gene, by the gRNA-CRISPR enzyme complex may be largely knockout (knock-out), knockdown, knockin (knock-in) and increased expression.

The "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when a target gene or a chromosome is edited using the gRNA-CRISPR enzyme complex, that is, the CRISPR complex, the target gene or the chromosome may be cleaved using the CRISPR complex. The target gene or the chromosome damaged using the CRISPR complex may be repaired by NHEJ. In the damaged target gene or chromosome, an indel is generated by NHEJ and thereby inducing target gene or chromosome-specific knockout.

In another example, when a target gene or a chromosome is edited using the gRNA-CRISPR enzyme complex, that is, the CRISPR complex and a donor, the target gene or nucleic acid may be cleaved using the CRISPR complex. The target gene or nucleic acid damaged using the CRISPR complex may be repaired by HDR using a donor. Here, the donor includes a homologous nucleotide sequence and a nucleotide sequence desired to be inserted. Here, the number of nucleotide sequences to be inserted may vary according to an insertion location or purpose. When the damaged target gene or chromosome is repaired using a donor, a nucleotide sequence to be inserted is inserted into the damaged nucleotide sequence region, and thereby inducing target gene or chromosome-specific knockout.

The "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when a target gene or a chromosome is edited using a gRNA-CRISPR inactive enzyme-transcription inhibitory activity domain complex, that is, a CRISPR-inactive complex including a transcription inhibitory activity domain, the CRISPR-inactive complex may specifically bind to the target gene or chromosome, and the transcription of the target gene or chromosome is inhibited by the transcription inhibitory activity domain included in the CRISPR-inactive complex, thereby inducing knockdown in which the expression of a target gene or chromosome is inhibited.

In another example, when a target gene or a chromosome is edited using the gRNA-CRISPR enzyme complex, that is, the CRISPR complex and a donor, the promoter and/or enhancer region(s) of the target gene or chromosome may be cleaved using the CRISPR complex. Here, the gRNA may recognize a partial nucleotide sequence of the promoter and/or enhancer region(s) of the target gene or chromosome as a target sequence. The target gene or chromosome damaged using the CRISPR complex may be repaired by NHEJ. In the damaged target gene or chromosome, an indel is generated by NHEJ, thereby inducing target gene or chromosome-specific knockdown. Alternatively, when a donor is optionally used, the target gene or chromosome damaged using the CRISPR complex may be repaired by HDR. When the damaged target gene or chromosome is repaired using a donor, a nucleotide sequence to be inserted is inserted into the damaged nucleotide sequence region, thereby inducing target gene or chromosome-specific knockdown.

The "knockin" refers to insertion of a specific nucleic acid or gene into a target gene or nucleic acid, and here, the "specific nucleic acid or gene" refers to a gene or nucleic acid of interest to be inserted or expressed. A mutant gene triggering a disease may be utilized in disease treatment by correction to normal or insertion of a normal gene to induce expression of the normal gene through the knockin.

In addition, the knockin may further need a donor.

For example, when a target gene or nucleic acid is edited using the gRNA-CRISPR enzyme complex, that is, the CRISPR complex and a donor, the target gene or nucleic acid may be cleaved using the CRISPR complex. The target gene or nucleic acid damaged using the CRISPR complex may be repaired by HDR using a donor. Here, the donor may include a specific nucleic acid or gene, and may be used to insert a specific nucleic acid or gene into the damaged gene or chromosome. Here, the inserted specific nucleic acid or gene may induce the expression of a protein.

The "increase in expression" refers to an increase in transcription and/or translation of a target gene or nucleic acid or an increase in the expression of a target protein, compared to before artificial manipulation. The onset of a disease may be prevented or a disease may be cured by regulating the expression of a gene or protein, which is less expressed or not expressed, through an increase in expression.

For example, when a target gene or chromosome having a mutation is edited or corrected using a gRNA-CRISPR enzyme complex, that is, a CRISPR complex, the target gene or chromosome may be cleaved using the CRISPR complex. The target gene or chromosome damaged by the CRISPR complex may be repaired by NHEJ. Insertion/deletion may occur in the damaged target gene or chromosome by NHEJ, and because of the insertion/deletion, the normal expression of a target gene or chromosome may be induced by removing a mutant sequence or changing a reading frame.

In another example, when a target gene or chromosome having a mutation is edited or corrected using a gRNA-CRISPR enzyme complex, that is, a CRISPR complex and a donor, the target gene or a nucleic acid may be cleaved using the CRISPR complex. The target gene or nucleic acid damaged by the CRISPR complex may be repaired by HDR using a donor. Here, the donor includes a homology nucleotide sequence and a nucleotide sequence to be inserted. Here, the number of nucleotide sequences to be inserted may be variously regulated according to an insertion position or purpose. When the damaged gene or chromosome is repaired using the donor including a nucleotide sequence capable of correcting a mutation, the nucleotide sequence that can correct a mutation may be inserted into the damaged nucleotide region, and therefore, the normal expression of a target gene or chromosome may be induced.

In One Embodiment of the Disclosure of the Present Specification, the gRNA-CRISPR Enzyme Complex May Impart an Artificial Manipulation or Modification to a RPE65 Gene, a GUCY2D Gene, a SPATA7 Gene, an AIPL1 Gene, a LCA5 Gene, a RPGRIP1 Gene, a CRB1 Gene, a CEP290 Gene, an IMPDH1 Gene, a RD3 Gene, a RDH12 Gene and/or a CRX Gene.

The gRNA-CRISPR enzyme complex may specifically recognize a target sequence of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The target sequence may be specifically recognized by gRNA of the gRNA-CRISPR enzyme complex, and therefore, the gRNA-CRISPR enzyme complex may be located near the recognized target sequence.

The target sequence may be a region or area in which an artificial modification occurs in the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The target sequence may be a contiguous nucleotide sequence of 10 to 25 bp, located in a promoter region of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The target sequence may be a contiguous nucleotide sequence of 10 to 25 bp, located in an intron region of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The target sequence may be a contiguous nucleotide sequence of 10 to 25 bp, located in an exon region of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The target sequence may be a contiguous nucleotide sequence of 10 to 25 bp, located in an enhancer region of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The target sequence may be a contiguous nucleotide sequence of 10 to 25 bp, located near the 5' end and/or 3' end of a PAM sequence in the nucleic acid sequence of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

Here, the PAM sequence may be one or more of the following sequences (described in a 5' to 3' direction):

NGG (N is A, T, C or G);
NNNNRYAC (N is each independently A, T, C or G, R is A or G, and Y is C or T);
NNAGAAW (N is each independently A, T, C or G, and W is A or T);
NNNNGATT (N is each independently A, T, C or G);
NNGRR(T) (N is each independently A, T, C or G, and R is A or G); and
TTN (N is A, T, C or G).

In one embodiment, the target sequence may be one or more nucleotide sequences selected from the nucleotide sequences described in Tables 1 and 2.

The gRNA-CRISPR enzyme complex may consist of a gRNA and a CRISPR enzyme.

The gRNA may include a guide domain capable of partial or complete complementary binding with a guide nucleic acid-binding sequence of a target sequence of the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

The guide domain may have at least 70%, 75%, 80%, 85%, 90% or 95% complementarity or complete complementarity to the guide nucleic acid-binding sequence.

The guide domain may include a nucleotide sequence complementary to the guide nucleic acid-binding sequence of the target sequence of the RPE65 gene. Here, the complementary nucleotide sequence may include 0 to 5, 0 to 4, 0 to 3, or 0 to 2 mismatches.

The guide domain may include a nucleotide sequence complementary to the guide nucleic acid-binding sequence of the target sequence of the GUCY2D gene. Here, the complementary nucleotide sequence may include 0 to 5, 0 to 4, 0 to 3, or 0 to 2 mismatches.

The guide domain may include a nucleotide sequence complementary to the guide nucleic acid-binding sequence of the target sequence of the SPATA7 gene. Here, the complementary nucleotide sequence may include 0 to 5, 0 to 4, 0 to 3, or 0 to 2 mismatches.

The guide domain may include a nucleotide sequence complementary to the guide nucleic acid-binding sequence of the target sequence of the AIPL1 gene. Here, the complementary nucleotide sequence may include 0 to 5, 0 to 4, 0 to 3, or 0 to 2 mismatches.

The guide domain may include a nucleotide sequence complementary to the guide nucleic acid-binding sequence of the target sequence of the LCA5 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the RPGRIP1 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the CRB1 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the CEP290 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the IMPDH1 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the RD3 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the RDH12 gene. Here, the complementary nucleotide sequence may include 0 to 5, 0 to 4, 0 to 3, or 0 to 2 mismatches.

The guide domain may include a complementary nucleotide sequence in the guide nucleic acid-binding sequence of the target sequence of the CRX gene. Here, the complementary nucleotide sequence may include 0 to 5, 0 to 4, 0 to 3, or 0 to 2 mismatches.

The gRNA may include one or more domains selected from the group consisting of a first complementary domain, a linker domain, a second complementary domain, a proximal domain and a tail domain.

The CRISPR enzyme may be one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a Neisseria meningitidis-derived Cas9 protein and a Cpf1 protein. In one example, the editor protein may be a *Campylobacter jejuni*-derived Cas9 protein or a *Staphylococcus aureus*-derived Cas9 protein.

The gRNA-CRISPR enzyme complex may impart various artificial manipulations or modifications to the RPE65 gene, the GUCY2D gene, the SPATA7 gene, the AIPL1 gene, the LCA5 gene, the RPGRIP1 gene, the CRB1 gene, the CEP290 gene, the IMPDH1 gene, the RD3 gene, the RDH12 gene and/or the CRX gene.

In the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may occur in a contiguous nucleotide sequence region of 1 to 50 bp, located in a target sequence or near the 5' end and/or 3' end of a target sequence. The modifications are as follows:

i) deletion of one or more nucleotides,
ii) substitution of one or more nucleotides with nucleotide(s) different from a wild-type gene,
iii) insertion of one or more nucleotides, or
iv) a combination of two or more selected from i) to iii).

For example, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more nucleotides may be deleted in a contiguous nucleotide sequence region of 1 to 50 bp, located in a target sequence or near the 5' end and/or 3' end of a target sequence. In one example, the deleted nucleotides may be a 1, 2, 3, 4 or 5 bp sequential or non-sequential nucleotides. In another example, the deleted nucleotides may be a nucleotide fragment consisting of sequential nucleotides of 2 bp or more. Here, the nucleotide fragment may be 2 to 5 bp, 6 to 10 bp, 11 to 15 bp, 16 to 20 bp, 21 to 25 bp, 26 to 30 bp, 31 to 35 bp, 36 to 40 bp, 41 to 45 bp or 46 to 50 bp in size. In still another example, the deleted nucleotides may be two or more nucleotide fragments. Here, two or more nucleotide fragments may be independent nucleotide fragments, which are not contiguous, that is, have one or more nucleotide sequence gaps, and two or more deletion sites may be generated due to the two or more deleted nucleotide fragments.

Alternatively, for example, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, the insertion of one or more nucleotides may occur in a contiguous nucleotide sequence region of 1 to 50 bp, located in a target sequence or near the 5' end and/or 3' end of a target sequence. In one example, the inserted nucleotides may be a 1, 2, 3, 4 or 5 bp sequential nucleotides. In another example, the inserted nucleotides may be a nucleotide fragment consisting of 5 bp or more sequential nucleotides. Here, the nucleotide fragment may be 5 to 10 bp, 11 to 50 bp, 50 to 100 bp, 100 to 200 bp, 200 to 300 bp, 300 to 400 bp, 400 to 500 bp, 500 to 750 bp or 750 to 1000 bp in size. In still another example, the inserted nucleotides may be a partial or complete nucleotide sequence of a specific gene. Here, the specific gene may be a gene introduced from the outside, which is not included in an object including a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene, for example, a human cell. Alternatively, the specific gene may be a gene included in an object including a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene, for example, a human cell. For example, the specific gene may be a gene present in the genome of a human cell.

Alternatively, for example, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more nucleotides may be deleted and inserted in a contiguous nucleotide sequence region of 1 to 50 bp, located in a target sequence or near the 5' end and/or 3' end of a target sequence. In one example, the deleted nucleotides may be a 1, 2, 3, 4 or 5 bp sequential or non-sequential nucleotides. Here, the inserted nucleotides may be a 1, 2, 3, 4 or 5 bp nucleotides; a nucleotide fragment; or a partial or complete nucleotide sequence of a specific gene, and the deletion and insertion may sequentially or simultaneously occur. Here, the inserted nucleotide fragment may be 5 to 10 bp, 11 to 50 bp, 50 to 100 bp, 100 to 200 bp, 200 to 300 bp, 300 to 400 bp, 400 to 500 bp, 500 to 750 bp or 750 to 1000 bp in size. Here, the specific gene may be a gene introduced from the outside, which is not included in an object including a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene, for example, a human cell. Alternatively, the specific gene may be a gene included in an object including a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene, for example, a human cell. For example, the specific gene may be a gene present in the genome of a human cell. In another example, the deleted nucleotides may be a nucleotide fragment consisting of 2 bp or more nucleotides. Here, the deleted nucleotide fragment may be 2 to 5 bp, 6 to 10 bp, 11 to 15 bp, 16 to 20 bp, 21 to 25 bp, 26 to 30 bp, 31 to 35 bp, 36 to 40 bp, 41 to 45 bp or 46 to 50 bp in size. Here, the inserted nucleotides may be 1, 2, 3, 4 or 5 bp; a nucleotide fragment; or a partial or complete nucleotide sequence of a specific gene, and the deletion and insertion may sequentially or simultaneously occur. In still another example, the deleted nucleotides may be two or more nucleotide fragments. Here, the inserted nucleotides may be 1, 2, 3, 4 or 5 bp nucleotides; a nucleotide fragment; or a partial or complete nucleotide sequence of a specific gene, and the deletion and insertion may sequentially or simultaneously occur. In addition, the insertion may occur in a partial or complete part of the two or more deleted parts.

The gRNA-CRISPR enzyme complex may impart various artificial manipulations or modifications to the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene according to the types of gRNA and CRISPR enzyme.

In one example, when the CRISPR enzyme is a SpCas9 protein, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may be included in a contiguous nucleotide sequence region of 1 to 50 bp, 1 to 40 bp or 1 to 30 bp, and preferably, 1 to 25 bp, located near the 5' end and/or 3' end of the PAM sequence of 5'-NGG-3' (N is A, T, G or C) present in a target region of each gene. The modifications are as follows:
i) deletion of one or more nucleotides,
ii) substitution of one or more nucleotides with nucleotide(s) different from a wild-type gene,
iii) insertion of one or more nucleotides, or
iv) a combination of two or more selected from i) to iii).

In another example, when the CRISPR enzyme is a CjCas9 protein, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may be included in a contiguous nucleotide sequence region of 1 to 50 bp, 1 to 40 bp or 1 to 30 bp, and preferably, 1 to 25 bp, located near the 5' end and/or 3' end of the PAM sequence of 5'-NNNNRYAC-3' (N is each independently A, T, C or G, R is A or G, and Y is C or T) present in a target region of each gene. The modifications are as follows:
i) deletion of one or more nucleotides,
ii) substitution of one or more nucleotides with nucleotide(s) different from a wild-type gene,
iii) insertion of one or more nucleotides, or
iv) a combination of two or more selected from i) to iii).

In still another example, when the CRISPR enzyme is a StCas9 protein, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may be included in a contiguous nucleotide sequence region of 1 to 50 bp, 1 to 40 bp or 1 to 30 bp, and preferably, 1 to 25 bp, located near the 5' end and/or 3' end of the PAM sequence of 5'-NNAGAAW-3'(N is each independently A, T, C or G, and W is A or T) present in a target region of each gene. The modifications are as follows:
i) deletion of one or more nucleotides,
ii) substitution of one or more nucleotides with nucleotide(s) different from a wild-type gene,
iii) insertion of one or more nucleotides, or
iv) a combination of two or more selected from i) to iii).

In one example, when the CRISPR enzyme is a NmCas9 protein, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may be included in a contiguous nucleotide sequence region of 1 to 50 bp, 1 to 40 bp or 1 to 30 bp, and preferably, 1 to 25 bp, located near the 5' end and/or 3' end of the PAM sequence of 5'-NNNNGATT-3' (N is each independently A, T, C or G) present in a target region of each gene. The modifications are as follows:
i) deletion of one or more nucleotides,
ii) substitution of one or more nucleotides with nucleotide(s) different from a wild-type gene,
iii) insertion of one or more nucleotides, or
iv) a combination of two or more selected from i) to iii).

In yet another example, when the CRISPR enzyme is a SaCas9 protein, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may be included in a contiguous nucleotide sequence region of 1 to 50 bp, 1 to 40 bp or 1 to 30 bp, and preferably, 1 to 25 bp, located near the 5' end and/or 3' end of the PAM sequence of 5'-NNGRR(T)-3' (N is each independently A, T, C or G, R is A or G, and (T) means any insertable sequence) present in a target region of each gene. The modifications are as follows:
i) deletion of one or more nucleotides,
ii) substitution of one or more nucleotides with nucleotide(s) different from a wild-type gene,
iii) insertion of one or more nucleotides, or
iv) a combination of two or more selected from i) to iii).

In yet another example, when the CRISPR enzyme is a Cpf1 protein, in the artificially manipulated or modified RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, one or more modifications may be included in a contiguous nucleotide sequence region of 1 to 50 bp, 1 to 40 bp or 1 to 30 bp, and preferably, 1 to 25 bp, located near the 5' end and/or 3' end of the PAM sequence of 5'-TTN-3' (N is A, T, C or G) present in a target region of each gene. The modifications are as follows:
i) deletion of one or more nucleotides,
ii) substitution of one or more nucleotides with nucleotide(s) different from a wild-type gene,
iii) insertion of one or more nucleotides, or
iv) a combination of two or more selected from i) to iii).

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex, may be knock-out.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex, may be to inhibit the expression of a protein encoded by each of the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex, may be knock-down.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex, may be to reduce the expression of a protein encoded by each of the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex, may be knock-in.

Here, the knock-in effect may be induced by the gRNA-CRISPR enzyme complex and a donor additionally including a foreign nucleotide sequence or gene.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex and a donor, may be to express a peptide or protein encoded by a foreign nucleotide sequence or gene.

Here, the knock-in effect may be induced by the gRNA-CRISPR enzyme complex and a donor including a nucleotide sequence to be inserted.

The nucleotide sequence to be inserted may be a normal nucleotide sequence for correcting a mutant nucleotide sequence of the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, which has (have) one or more mutations.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex and a donor, may be to express a protein encoded by a gene obtained by correcting a mutant nucleotide sequence of the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, which has (have) one or more mutations, to a normal nucleotide sequence.

Here, the knock-in effect may be induced by the gRNA-CRISPR enzyme complex and a donor for correction.

The donor for correction may be a donor including a normal nucleotide sequence for correcting a mutant nucleotide sequence of the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, which has (have) one or more mutations.

The artificial manipulation effect on the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene, caused by the gRNA-CRISPR enzyme complex and a donor for correction, may be to express a protein encoded by a normal gene by correcting a mutant nucleotide sequence of the RPE65 gene, GUCY2D gene, SPATA7 gene, AIPL1 gene, LCA5 gene, RPGRIP1 gene, CRB1 gene, CEP290 gene, IMPDH1 gene, RD3 gene, RDH12 gene and/or CRX gene.

One Aspect Disclosed in the Present Specification Relates to a Method of Treating a Retinal Dysfunction Disease Using a Composition for Gene Manipulation for Treating a Retinal Dysfunction Disease.

One embodiment disclosed in the present specification provides a use for treating a retinal dysfunction disease using a method including administering a composition for gene manipulation for artificially manipulating a retinal function-forming gene into a treatment subject.

Here, the treatment subject may be a mammal including primates such as a human, a monkey, etc. and rodents such as a rat, a mouse, etc.

The "retinal dysfunction" means all states including all forms and processes and/or consequential outcomes in which retinal tissue does not properly function. Therefore, the "retinal dysfunction disease" refers to all conditions including all diseases occurring due to the above-mentioned state, and also includes all diseases exhibiting a retinal abnormality as a pathological feature.

Here, the "pathological feature" refers to a disease-caused change at the cellular, tissue, organ or individual level of an organism, and the "retinal abnormality" refers to an abnormality or abnormal function and/or role of retinal tissue, and a disease exhibiting an retinal abnormality as a pathological feature is a disease showing an abnormality or an abnormal function of retinal tissue of an organism as a pathological feature, and includes an ocular disease, an optic nerve-related disease, ocular tumors, etc.

The retinal dysfunction disease may be Leber congenital amaurosis (LCA), retinal pigmentosa, Stargardt disease, retinal dysplasia, color blindness, choroideremia, macular degeneration, myopic choroidal neovascularization (CNV), polypoidal choroidal vasculopathy (PCV), central serous chorioretinopathy (CSCR), a macular hole, occult macular dystrophy, diabetic retinopathy, a retinal artery/vein occlusion, hypertensive retinopathy, a retinal macroaneurysm, ocular ischemic syndrome, retinopathy of prematurity, acute retinal necrosis, cytomegaloviral retinitis, toxoplasmic retinochoroiditis, syphilitic chorioretinitis, retinal detachment or retinoblastoma.

In one embodiment, the retinal dysfunction disease may be Leber congenital amaurosis or retinal pigmentosa.

Retinitis Pigmentosa (RP)

RP is a progressive disease caused by problems with a photoreceptor function, and a retinal degenerative disease generally affecting photoreceptors and the retinal pigment epithelium. RP has been reported to occur in approximately one in 4,000 people worldwide.

The cause of RP is not yet clear, but is thought to be due to a genetic abnormality, and RP may be classified into cases with and without family history. If there is a family history, autosomal dominant, autosomal recessive and sex-linked inheritances are shown, and if there is no family history, this case is called a single type, which has a possibility of having an abnormal gene. It has been reported that there are differences in clinical features and progression of the disease depending on a genotype and a causative gene, but further studies are needed.

Symptoms of RP include night blindness, narrowing of the visual field, photophobia and vision impairment, and generally, when a person has RP, visual cells have an abnormality and thus it is difficult for a person to adapt when entering a dark site from a bright site. In addition, in the dim light or the darkness, it is difficult to recognize an object (night blindness), and as the disease progresses, the visual field, which is the area in which surrounding objects can be seen, gradually narrows. As the narrowing of the visual field progresses, tunnel vision, as seen through a narrow tube, occurs, and photophobia, which results in difficulty in recognizing surrounding objects under intense light, occurs. In addition, as the disease progresses, damage to cone cells in the center of the retina may lead to the loss of central vision, resulting in legal blindness.

Leber Congenital Amaurosis (LCA)

LCA is a very rare hereditary eye disease, and one of the most significant hereditary retinal abnormalities, which may result in congenital blindness at birth or right after birth, and according to reports from abroad, it has been known that 2 to 3 in 100,000 people, and 10 to 18% of children at special schools for visual impairment have LCA.

LCA is a disease caused by a genetic abnormality, and genetic mutations are found in 40 to 50% of patients. There are 11 autosomal recessive mutations (GUCY2D, RPE65, SPATA7, AIPL1, LCA5, RPGRIP1, CRB1, CEP290, IMPDH1, RD3, RDH12) among the 12 known gene abnormalities, and rarely, is autosomal dominant inheritance (CRX) present.

Since LCA patients have no normally-functioning rod cells and cone cells in the retina, loss of both a cone cell response and a rod cell response occurs in electroretinography, and symptoms such as severe vision loss or blindness at birth or right after birth, nystagmus, a wandering gaze, slow and gentle pupil reflexes, retinitis pigmentosa, etc. A reduction in response to visual stimuli is the first symptom, and a symptom of pressing an eye with a first or finger is frequently shown, sometimes causing enophthalmos. Other symptoms may include strabismus, nystagmus, photophobia, cataracts and keratoconus, and some children with the disease also have hearing loss, mental retardation and developmental delay. In addition, 36 to 68% of the LCA patients have central nervous system anomalies, most frequently have corpus callosal agenesis, and also have gyrus abnormalities such as macrogyria or polymicrogyria, occipital meningoceles and encephaloceles, aqueductal stenosis, lipomyelomeningoceles and spina bifida (rachischisis). 47 to 65% of the LCA patients have systemic deformities. Facial deformities such as facial hemangioma, ear dysplasia, cleft lip, cleft palate, microstomia, craniofacial dysostosis, cataracts due to abnormal eye development, sclerocornea and retinal dysgenesis may occur. Cardiovascular abnormalities such as ventricular septal defects, patent ductus arteriosus, aortic coarctation of aorta, dextrocardia and single ventricle heart disease, and genitourinary anomalies such as multicystic kidney, hydronephrosis, cryptorchism and external genital hypoplasia may occur. In addition, polydactyly, syndactyly, pyloric stenosis, congenital diaphragmatic hernia, Meckel's diverticulum, congenital rubella syndrome, Cornelia de Langes syndrome and Klippel-Feil syndrome may occur.

One embodiment of the disclosure of the present specification provides a pharmaceutical composition including a composition for gene manipulation, which may artificially manipulate a retinal function-forming gene.

The description related to the composition for gene manipulation is as described above.

In one embodiment, the composition for gene manipulation may include the following components:
(a) a guide nucleic acid capable of targeting a target sequence of a retinal function-forming gene or a nucleic acid sequence encoding the same; and
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or nucleic acid sequence(s) encoding the same.

Here, the retinal function-forming gene may be a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene.

Here, the composition for gene manipulation may include a vector including nucleic acid sequences encoding a guide nucleic acid and/or an editor protein, respectively.

Here, the guide nucleic acid or a nucleic acid sequence encoding the same; and a nucleic acid sequence encoding the editor protein may be present in the form of one or more vectors. They may be present in form of a homologous or heterologous vector.

In another embodiment, the composition for gene manipulation may include the following components:
(a) a guide nucleic acid capable of targeting a target sequence of a retinal function-forming gene or a nucleic acid sequence encoding the same;
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or nucleic acid sequence(s) encoding the same; and
(c) a donor including a nucleic acid sequence to be inserted or a nucleic acid sequence encoding the same.

Here, the nucleic acid sequence to be inserted may be a partial sequence of the retinal function-forming gene.

Alternatively, the nucleic acid sequence to be inserted may be a nucleic acid sequence for correcting a mutation of the retinal function-forming gene to be manipulated.

Here, the guide nucleic acid or a nucleic acid sequence encoding the same; and a nucleic acid sequence encoding the editor protein; and a donor including a nucleic acid sequence to be inserted or a nucleic acid sequence encoding the same may be present in the form of one or more vectors. They may be present in the form of a homologous or heterologous vector.

The pharmaceutical composition may further include an additional component.

The additional component may include a suitable carrier for delivery into the body of a subject.

One embodiment of the disclosure of the present specification provides a method of treating a retinal dysfunction disease, which include administering a composition for gene manipulation to an organism with a retinal dysfunction disease to treat the retinal dysfunction disease.

The treatment method may be a treatment method of regulating a retinal function-forming system by manipulating a gene of an organism. Such a treatment method may be achieved by directly injecting a composition for gene manipulation into a body to manipulate a gene of an organism.

The description delated to the composition for gene manipulation is as described above.

In one embodiment, the composition for gene manipulation may include the following components:
(a) a guide nucleic acid capable of targeting a target sequence of a retinal function-forming gene or a nucleic acid sequence encoding the same; and
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or nucleic acid sequence(s) encoding the same.

Here, the retinal function-forming gene may be a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene.

The guide nucleic acid and the editor protein may each be present in one or more vectors in the form of a nucleic acid sequence, or present by forming a complex by combining the guide nucleic acid and the editor protein.

Optionally, the composition for gene manipulation may further include a donor including a nucleic acid sequence to be inserted or a nucleic acid sequence encoding the same.

Here, the nucleic acid sequence to be inserted may be a partial sequence of the retinal function-forming gene.

Alternatively, the nucleic acid sequence to be inserted may be a nucleic acid sequence for correcting a mutation of the retinal function-forming gene to be manipulated.

Each of the guide nucleic acid and the editor protein, and/or a donor may be present in one or more vectors in the form of a nucleic acid sequence.

Here, the vector may be a plasmid or a viral vector.

Here, the viral vector may be one or more selected from the group consisting of a retrovirus, a lentivirus, an adenovirus, an adeno-associated virus (AAV), a vaccinia virus, a poxvirus and a herpes simplex virus.

The description related to the retinal dysfunction disease is as described above.

The retinal dysfunction disease may be LCA, retinal pigmentosa, Staccart's disease, retinal dysplasia, color blindness, choroideremia, macular degeneration, myopic choroidal neovascularization (CNV), polypoidal choroidal vasculopathy (PCV), central serous chorioretinopathy (CSCR), a macular hole, occult macular dystrophy, diabetic retinopathy, a retinal artery/vein occlusion, hypertensive retinopathy, a retinal macroaneurysm, ocular ischemic syndrome, retinopathy of prematurity, acute retinal necrosis, cytomegaloviral retinitis, toxoplasmic retinochoroiditis, syphilitic chorioretinitis, retinal detachment or retinoblastoma.

The composition for gene manipulation may be administered into a treatment subject with a retinal dysfunction disease.

The treatment subject may be a mammal including primates such as a human, a monkey, etc. and rodents such as a rat, a mouse, etc.

The composition for gene manipulation may be administered to a treatment subject.

The administration may be performed by injection, transfusion, implantation or transplantation.

The administration may be performed via an administration route selected from subretinal, subcutaneous, intradermal, intraocular, intravitreal, intratumoral, intranodal, intramedullar, intramuscular, intravenous, intralymphatic or intraperitoneal routes.

A dose (a pharmaceutically effective amount for obtaining a predetermined, desired effect) of the composition for gene manipulation is approximately $10^4$ to $10^9$ cells/kg (body weight of an administration subject), for example, approximately $10^5$ to $10^6$ cells/kg (body weight), which may be selected from all integers in the numerical range, but the present invention is not limited thereto. The composition may be suitably prescribed in consideration of an age, health condition and body weight of an administration subject, the type of concurrent treatment, and if possible, the frequency of treatment and a desired effect.

When the retinal function-forming gene is artificially manipulated by the methods and compositions according to some embodiments disclosed in the present specification, it is possible to normalize a retinal function-forming system, and therefore, an effect of inhibiting or improving abnormal retinal function formation may be obtained.

One Embodiment Disclosed in the Present Specification Relates to a Method of Modifying a Retinal Function-Forming Gene in Eukaryotic Cells, which May be Performed In Vivo, Ex Vivo or In Vitro.

In some embodiments, the method includes sampling a cell or a cell population from a human or non-human animal, and modifying the cell or cells. Culturing may occur at any stage ex vivo. The cell or cells may even be re-introduced into a non-human animal or plant.

The method may be a method of artificially manipulating eukaryotic cells, which includes introducing a composition for gene manipulation into eukaryotic cells.

The description delated to the composition for gene manipulation is as described above.

In one embodiment, the composition for gene manipulation may include the following components:
(a) a guide nucleic acid capable of targeting a target sequence of a retinal function-forming gene or a nucleic acid sequence encoding the same; and
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or nucleic acid sequence(s) encoding the same.

Here, the retinal function-forming gene may be a RPE65 gene, a GUCY2D gene, a SPATA7 gene, an AIPL1 gene, a LCA5 gene, a RPGRIP1 gene, a CRB1 gene, a CEP290 gene, an IMPDH1 gene, a RD3 gene, a RDH12 gene and/or a CRX gene.

The guide nucleic acid and the editor protein may each be present in one or more vectors in the form of a nucleic acid sequence, or present by forming a complex by combining the guide nucleic acid and the editor protein.

Optionally, the composition for gene manipulation may further include a donor including a nucleic acid sequence to be inserted or a nucleic acid sequence encoding the same.

Here, the nucleic acid sequence to be inserted may be a partial sequence of the retinal function-forming gene.

Alternatively, the nucleic acid sequence to be inserted may be a nucleic acid sequence for correcting a mutation of the retinal function-forming gene to be manipulated.

Each of the guide nucleic acid and the editor protein, and/or a donor may be present in one or more vectors in the form of a nucleic acid sequence.

The introduction step may be performed in vivo or ex vivo.

For example, the introduction step may be performed by one or more methods selected from electroporation, liposomes, plasmids, viral vectors, nanoparticles and a protein translocation domain (PTD) fusion protein method.

For example, the viral vector may be one or more selected from the group consisting of a retrovirus, a lentivirus, an adenovirus, an adeno-associated virus (AAV), a vaccinia virus, a poxvirus and a herpes simplex virus.

EXAMPLES

Hereinafter, the present invention will be described in further detail with reference to examples.

These examples are merely provided to illustrate the present invention, and it will be obvious to those of ordinary skill in the art that the scope of the present invention is not limited by the following examples.

Experimental Materials and Experimental Methods 1. sgRNA Design and Primers

The CRISPR/Cas9 target sites of a human RPE65 gene were selected using CRISPR RGEN Tools (Institute for Basic Science, Korea). The target sites of each gene varied according to the type of CRISPR enzyme, and the target sequences of each gene for SpCas9 are listed in Table 1 above, and the target sequences of each gene for CjCas9 are listed in Table 2 above. In addition, indel frequencies for the target sequences are listed in Tables 3 and 4.

TABLE 3

Indel frequencies for target sequences of human RPE65 using SpCas9

| Loci. | Target name | Target(w/o PAM) | PAM | Mismatch (0b, 1b, 2b) | GC content | Indels (%) | SEQ ID NO |
|---|---|---|---|---|---|---|---|
| Exon2 | Sp20-hRPE65-E02-#01 | AGTTTCTTGTAACCACCAGC | AGG | 1, 0, 0 | 45 | 35.4% | SEQ ID NO: 1 |
| | Sp20-hRPE65-E02-#02 | TACATGAGCTGTGAGCGGCG | AGG | 1, 0, 0 | 60 | 39.9% | SEQ ID NO: 2 |
| | Sp20-hRPE65-E02-#03 | CCGCTCACAGCTCATGTAAC | AGG | 1, 0, 0 | 55 | 16.1% | SEQ ID NO: 3 |
| | Sp20-hRPE65-E02-#04 | TCACAGCTCATGTAACAGGT | TGG | 1, 0, 0 | 45 | 47.0% | SEQ ID NO: 4 |
| Exon3 | Sp20-hRPE65-E03-#01 | GGAGACTGCCGGTGAGCCAG | AGG | 1, 0, 0 | 70 | 32.7% | SEQ ID NO: 5 |
| | Sp20-hRPE65-E03-#02 | ACCGGCAGTCTCCTTCGATG | TGG | 1, 0, 0 | 60 | 30.0% | SEQ ID NO: 6 |
| | Sp20-hRPE65-E03-#03 | AGTCTCCTTCGATGTGGGCC | AGG | 1, 0, 0 | 60 | 19.2% | SEQ ID NO: 7 |
| | Sp20-hRPE65-E03-#04 | AGAGTCCTGGCCCACATCGA | AGG | 1, 0, 0 | 60 | 11.0% | SEQ ID NO: 8 |
| | Sp20-hRPE65-E03-#05 | GGGCTTGCCCATCAAACAGG | TGG | 1, 0, 0 | 60 | 20.4% | SEQ ID NO: 9 |
| | Sp20-hRPE65-E03-#06 | TAAAGTCAAACTTGTGCAGG | AGG | 1, 0, 0 | 40 | 11.8% | SEQ ID NO: 10 |
| Exon4 | Sp20-hRPE65-E04-#01 | TCCGCACTGATGCTTACGTA | CGG | 1, 0, 0 | 50 | 7.6% | SEQ ID NO: 11 |
| | Sp20-hRPE65-E04-#02 | CCGCACTGATGCTTACGTAC | GGG | 1, 0, 0 | 55 | 32.1% | SEQ ID NO: 12 |
| | Sp20-hRPE65-E04-#03 | CCCGTACGTAAGCATCAGTG | CGG | 1, 0, 0 | 55 | 6.0% | SEQ ID NO: 13 |
| | Sp20-hRPE65-E04-#04 | TACGGGCAATGACTGAGAAA | AGG | 1, 0, 0 | 45 | 28.0% | SEQ ID NO: 14 |
| | Sp20-hRPE65-E04-#05 | AGGATCGTCATAACAGAATT | TGG | 1, 0, 0 | 35 | 13.8% | SEQ ID NO: 15 |
| Exon5 | Sp20-hRPE65-E05-#01 | CCACTGGGTAGACATTAACA | AGG | 1, 0, 0 | 45 | 28.1% | SEQ ID NO: 16 |
| | Sp20-hRPE65-E05-#02 | CGTAGTAATCTTCCCCCACT | GGG | 1, 0, 0 | 50 | 25.2% | SEQ ID NO: 17 |
| | Sp20-hRPE65-E05-#03 | GCGTAGTAATCTTCCCCCAC | TGG | 1, 0, 0 | 55 | 34.3% | SEQ ID NO: 18 |
| Exon6 | Sp20-hRPE65-E06-#01 | GCAACTATGTCTCTGTCAAT | GGG | 1, 0, 0 | 40 | 11.9% | SEQ ID NO: 19 |
| | Sp20-hRPE65-E06-#02 | CAACTATGTCTCTGTCAATG | GGG | 1, 0, 0 | 40 | 28.1% | SEQ ID NO: 20 |
| | Sp20-hRPE65-E06-#03 | TTCAATGTGGGGGTGAGCAG | TGG | 1, 0, 0 | 55 | 21.3% | SEQ ID NO: 21 |
| | Sp20-hRPE65-E06-#04 | CACCCCCACATTGAAAATGA | TGG | 1, 0, 0 | 45 | 2.8% | SEQ ID NO: 22 |
| | Sp20-hRPE65-E06-#05 | CGGTTCCATCATTTTCAATG | TGG | 1, 0, 0 | 40 | 10.1% | SEQ ID NO: 23 |
| | Sp20-hRPE65-E06-#06 | GATGGAACCGTTTACAATAT | TGG | 1, 0, 0 | 35 | 9.3% | SEQ ID NO: 24 |
| Exon7 | Sp20-hRPE65-E07-#01 | GCTTGAATCGGTCACTGCAG | GGG | 1, 0, 0 | 55 | 16.0% | SEQ ID NO: 25 |
| | Sp20-hRPE65-E07-#02 | GAACGTAAGATGGCTTGAAT | CGG | 1, 0, 0 | 40 | 0.0% | SEQ ID NO: 26 |
| | Sp20-hRPE65-E07-#03 | AGTTACCTATGAACGTAAGA | TGG | 1, 0, 0 | 35 | 0.0% | SEQ ID NO: 27 |
| Exon8 | Sp20-hRPE65-E08-#01 | TCCCAACTATATCGTTTTTG | TGG | 1, 0, 0 | 35 | 0.0% | SEQ ID NO: 28 |
| | Sp20-hRPE65-E08-#02 | TCCACAAAAACGATATAGTT | GGG | 1, 0, 0 | 30 | 0.0% | SEQ ID NO: 29 |
| | Sp20-hRPE65-E08-#03 | ATATCTAAGACTTACCCCCA | TGG | 1, 0, 0 | 40 | 0.0% | SEQ ID NO: 30 |
| Exon10 | Sp20-hRPE65-E10-#01 | TAGCCAATTTACGTGAGAAC | TGG | 1, 0, 0 | 40 | 0.0% | SEQ ID NO: 31 |
| | Sp20-hRPE65-E10-#02 | AGCCAATTTACGTGAGAACT | GGG | 1, 0, 0 | 40 | 0.0% | SEQ ID NO: 32 |
| | Sp20-hRPE65-E10-#03 | TTCAGGTTGGGGAGCCTTTC | TGG | 1, 0, 0 | 55 | 0.0% | SEQ ID NO: 33 |

TABLE 3-continued

Indel frequencies for target sequences of human RPE65 using SpCas9

| Loci. | Target name | Target(w/o PAM) | PAM | Mismatch (0b, 1b, 2b) | GC content | Indels (%) | SEQ ID NO |
|---|---|---|---|---|---|---|---|
| | Sp20-hRPE65-E10-#04 | AGGCTCCCCAACCTGAAGTT | AGG | 1, 0, 0 | 55 | 4.8% | SEQ ID NO: 34 |
| | Sp20-hRPE65-E10-#05 | GTTACCTTGTCAATATTCAA | AGG | 1, 0, 0 | 30 | 0.0% | SEQ ID NO: 35 |
| Exon11 | Sp20-hRPE65-E11-#01 | TGTGCAGTGACGAGACTATC | TGG | 1, 0, 0 | 50 | 14.7% | SEQ ID NO: 36 |
| | Sp20-hRPE65-E11-#02 | CAGTGACGAGACTATCTGGC | TGG | 1, 0, 0 | 55 | 24.5% | SEQ ID NO: 37 |
| Exon12 | Sp20-hRPE65-E12-#01 | ATCAATTACCAGAAGTATTG | TGG | 1, 0, 0 | 30 | 10.8% | SEQ ID NO: 38 |
| | Sp20-hRPE65-E12-#02 | AAACCTTACACATATGCGTA | TGG | 1, 0, 0 | 35 | 0.0% | SEQ ID NO: 39 |
| | Sp20-hRPE65-E12-#03 | AGTCCATACGCATATGTGTA | AGG | 1, 0, 0 | 40 | 0.0% | SEQ ID NO: 40 |
| | Sp20-hRPE65-E12-#04 | TACACATATGCGTATGGACT | TGG | 1, 0, 0 | 40 | 0.0% | SEQ ID NO: 41 |
| | Sp20-hRPE65-E12-#05 | GAAGGATTAATTACCCTATC | TGG | 1, 0, 0 | 35 | 0.0% | SEQ ID NO: 42 |
| Exon14 | Sp20-hRPE65-E14-#01 | TGAAGTTGCCCGGGCTGAAG | TGG | 1, 0, 0 | 60 | 0.0% | SEQ ID NO: 43 |
| | Sp20-hRPE65-E14-#02 | GTTAATCTCCACTTCAGCCC | GGG | 1, 0, 0 | 50 | 0.0% | SEQ ID NO: 44 |

TABLE 4

Indel frequencies for target sequences of human RPE65 using CjCas9

| Loci. | Target name | Target(w/o PAM) | PAM | Mismatch (0b, 1b, 2b) | GC content | Indels (%) | SEQ ID NO |
|---|---|---|---|---|---|---|---|
| Exon3 | Cj22-hRPE65-E03-#01 | CACCTGTTTGATGGGCAAGCCC | TCCTGCAC | 1, 0, 0 | 59 | 0.0% | SEQ ID NO: 45 |
| | Cj22-hRPE65-E03-#02 | TTTGACTTTAAAGAAGGACATG | TCACATAC | 1, 0, 0 | 32 | 0.0% | SEQ ID NO: 46 |
| Exon4 | Cj22-hRPE65-E04-#01 | TGTTTCAATGTCCTTCAGGTTC | ATCCGCAC | 1, 0, 0 | 41 | 0.2% | SEQ ID NO: 47 |
| | Cj22-hRPE65-E04-#02 | TCAGGTTCATCCGCACTGATGC | TTACGTAC | 1, 0, 0 | 55 | 5.9% | SEQ ID NO: 48 |
| | Cj22-hRPE65-E04-#03 | GACGATCCTTTTCTCAGTCATT | GCCCGTAC | 1, 0, 0 | 41 | 0.0% | SEQ ID NO: 49 |
| | Cj22-hRPE65-E04-#04 | GAAAAGGATCGTCATAACAGAA | TTTGGCAC | 1, 0, 0 | 36 | 0.0% | SEQ ID NO: 50 |
| | Cj22-hRPE65-E04-#05 | ATATATTCTTGCAGGGATCTGG | GAAAGCAC | 1, 0, 0 | 41 | 56.5% | SEQ ID NO: 51 |
| Exon5 | Cj22-hRPE65-E05-#01 | CCCAGTGGGGAAGATTACTAC | GCTTGCAC | 1, 0, 0 | 55 | 0.0% | SEQ ID NO: 52 |
| Exon7 | Cj22-hRPE65-E07-#01 | ATCCAATAAGCAAGTCAGAGAT | CGTTGTAC | 1, 0, 0 | 36 | 0.0% | SEQ ID NO: 53 |
| | Cj22-hRPE65-E07-#02 | CTTGAATCGGTCACTGCAGGGG | AATTGTAC | 1, 0, 0 | 59 | 13.6% | SEQ ID NO: 54 |
| Exon8 | Cj22-hRPE65-E08-#01 | CTCCCAACTATATCGTTTTTGT | GGAGACAC | 1, 0, 0 | 36 | 0.0% | SEQ ID NO: 55 |
| Exon9 | Cj22-hRPE65-E09-#01 | CATATTGCTGACAAAAAAAGGA | AAAAGTAC | 1, 0, 0 | 32 | 3.9% | SEQ ID NO: 56 |
| | Cj22-hRPE65-E09-#02 | GGAGAAGTTCTGTATTTATTAT | TGAGGTAC | 1, 0, 0 | 27 | 0.0% | SEQ ID NO: 57 |
| | Cj22-hRPE65-E09-#03 | TCCTTTCAACCTCTTCCATCAC | ATCAACAC | 1, 0, 0 | 45 | 9.9% | SEQ ID NO: 58 |
| Exon10 | Cj22-hRPE65-E10-#01 | CTCCCCAACCTGAAGTTAGGAG | ATATGTAC | 1, 0, 0 | 55 | 9.4% | SEQ ID NO: 59 |
| | Cj22-hRPE65-E10-#02 | GGTTACCTTGTCAATATTCAAA | GGAAGTAC | 1, 0, 0 | 32 | 6.3% | SEQ ID NO: 60 |

TABLE 4-continued

Indel frequencies for target sequences of human RPE65 using CjCas9

| Loci. | Target name | Target(w/o PAM) | PAM | Mismatch (0b, 1b, 2b) | GC content | Indels (%) | SEQ ID NO |
|---|---|---|---|---|---|---|---|
| Exon11 | Cj22-hRPE65-E11-#01 | AGGCAAGAATTTAGTCACGCTC | CCCAATAC | 1, 0, 0 | 45 | 4.4% | SEQ ID NO: 61 |
|  | Cj22-hRPE65-E11-#02 | GGCTCCAGCCAGATAGTCTCGT | CACTGCAC | 1, 0, 0 | 59 | 0.0% | SEQ ID NO: 62 |
| Exon12 | Cj22-hRPE65-E12-#01 | TTACCAGAAGTATTGTGGGAAA | CCTTACAC | 1, 0, 0 | 36 | 0.0% | SEQ ID NO: 63 |
|  | Cj22-hRPE65-E12-#02 | TACGCATATGTGTAAGGTTTCC | CACAATAC | 1, 0, 0 | 41 | 0.1% | SEQ ID NO: 64 |
|  | Cj22-hRPE65-E12-#03 | GGAACAAAGTGATTCAAGCCAA | GTCCATAC | 1, 0, 0 | 41 | 1.8% | SEQ ID NO: 65 |
| Exon13 | Cj22-hRPE65-E13-#01 | ACTTGGGTTTGGCAAGAGCCTG | ATTCATAC | 1, 0, 0 | 55 | 0.4% | SEQ ID NO: 66 |
| Exon14 | Cj22-hRPE65-E14-#01 | CTGGGCTCACCACCACACTCAG | AACTACAC | 1, 0, 0 | 64 | 0.1% | SEQ ID NO: 67 |
|  | Cj22-hRPE65-E14-#02 | TTTGTCCTGCTCCTGGGCTCAC | CACCACAC | 1, 0, 0 | 59 | 2.3% | SEQ ID NO: 68 |
|  | Cj22-hRPE65-E14-#03 | CATGGACTGTTCAAAAAATCTT | GAGCATAC | 1, 0, 0 | 32 | 0.0% | SEQ ID NO: 69 |

In addition, primers used in the experiment are listed in Table 5.

TABLE 5

Primers used in the experiment

| | Target sites | Primer F (5' to 3') | | Primer R (5' to 3') | |
|---|---|---|---|---|---|
| On-targets | Rpe65-Donor-outside | ACTCTGTCCAAAGACCTCATGTGA | SEQ ID NO: 70 | TGGATGCTGAGTCATTGCTCTAAC | SEQ ID NO: 121 |
|  | Rpe65-TS1 | AGCTGACAAATAACAAATAGGCAC | SEQ ID NO: 71 | TGGTGAGGTCAGTCATGGACTTA | SEQ ID NO: 122 |
|  | Rpe65-TS4 | AGCTGACAAATAACAAATAGGCAC | SEQ ID NO: 72 | TGGTGAGGTCAGTCATGGACTTA | SEQ ID NO: 123 |
|  | RPE65 - Ex2-1 | TGCCTCTATCTCTGCGGACT | SEQ ID NO: 73 | AAACCACCTGATCCCTCTC | SEQ ID NO: 124 |
|  | RPE65 - Ex2-2 | TGCCTCTATCTCTGCGGACT | SEQ ID NO: 74 | AAACCACCTGATCCCTCTC | SEQ ID NO: 125 |
|  | RPE65 - Ex2-3 | TGCCTCTATCTCTGCGGACT | SEQ ID NO: 75 | AAACCACCTGATCCCTCTC | SEQ ID NO: 126 |
|  | RPE65 - Ex2-4 | TGCCTCTATCTCTGCGGACT | SEQ ID NO: 76 | AAACCACCTGATCCCTCTC | SEQ ID NO: 127 |
|  | RPE65 - Ex3-1 | CTGCCTTACCAAGGACAAGC | SEQ ID NO: 77 | AGGCCCTACTTTGAGGAGGA | SEQ ID NO: 128 |
|  | RPE65 - Ex3-2 | CTGCCTTACCAAGGACAAGC | SEQ ID NO: 78 | AGGCCCTACTTTGAGGAGGA | SEQ ID NO: 129 |
|  | RPE65 - Ex3-3 | CTGCCTTACCAAGGACAAGC | SEQ ID NO: 79 | AGGCCCTACTTTGAGGAGGA | SEQ ID NO: 130 |
|  | RPE65 - Ex3-4 | CTGCCTTACCAAGGACAAGC | SEQ ID NO: 80 | AGGCCCTACTTTGAGGAGGA | SEQ ID NO: 131 |
|  | RPE65 - Ex4-1 | GCTGTACGGATTGCTCCTGT | SEQ ID NO: 81 | TCAAGCCATGAGAGAAAAGG | SEQ ID NO: 132 |
|  | RPE65 - Ex4-2 | GCTGTACGGATTGCTCCTGT | SEQ ID NO: 82 | TCAAGCCATGAGAGAAAAGG | SEQ ID NO: 133 |
|  | RPE65 - Ex5-1 | TTCCAGGTTACTGAACCCAAA | SEQ ID NO: 83 | CCTAGCACTGTGTCCCACCT | SEQ ID NO: 134 |
|  | RPE65 - Ex5-2 | TTCCAGGTTACTGAACCCAAA | SEQ ID NO: 84 | CCTAGCACTGTGTCCCACCT | SEQ ID NO: 135 |
|  | RPE65 - Ex5-3 | TTCCAGGTTACTGAACCCAAA | SEQ ID NO: 85 | CCTAGCACTGTGTCCCACCT | SEQ ID NO: 136 |
|  | RPE65 - Ex6-1 | CCTTCTCTCAACTGGAGGACA | SEQ ID NO: 86 | TGCACAAAATGCTATTCTGACAT | SEQ ID NO: 137 |
|  | RPE65 - Ex6-2 | CCTTCTCTCAACTGGAGGACA | SEQ ID NO: 87 | TGCACAAAATGCTATTCTGACAT | SEQ ID NO: 138 |

TABLE 5-continued

Primers used in the experiment

| Target sites | | Primer F (5' to 3') | | Primer R (5' to 3') | |
|---|---|---|---|---|---|
| Off-targets (Mis-matched) | Off-1 | GGCTCTGGAAGTTACTCTCACTAG | SEQ ID NO: 88 | AGCCATTCAAGTTTCTCCCTTGAT | SEQ ID NO: 139 |
| | Off-2 | TGCCCTGTACACCCCAAATACACA | SEQ ID NO: 89 | GACGGTACATAAATGAGCAGCCTT | SEQ ID NO: 140 |
| | Off-3 | CACTTTGGATCCTCTGGCAACTCA | SEQ ID NO: 90 | TCCCCTTTCTTTGTAAGCACTCCT | SEQ ID NO: 141 |
| | Off-4 | CCCATGGACAGAGTTCTATAGACA | SEQ ID NO: 91 | GCTGTCCTCGAACTCAGAAATCCA | SEQ ID NO: 142 |
| | Off-5 | GCCAAATATATCCAAAGATAGTGG | SEQ ID NO: 92 | GTCAGTTGAACCGTGTGAAGTT | SEQ ID NO: 143 |
| | Off-6 | ATGGAATACGTGCCTTTGCAGGAA | SEQ ID NO: 93 | TCACAAGTAAGGGATGCTTCCTGT | SEQ ID NO: 144 |
| | Off-7 | CTCTAGTCTACCACCCTGAGAACT | SEQ ID NO: 94 | ATCACTAAGCTGTGCCAAGTAGCA | SEQ ID NO: 145 |
| | Off-8 | TGAAGAGAATCACTGCAGGGGATT | SEQ ID NO: 95 | CAGGGATGCTTAATGCACTGTGAA | SEQ ID NO: 146 |
| | Off-9 | GTTGGTTACCCCTCAGATAAAGGT | SEQ ID NO: 96 | GTTCTCACTTACATGTGGAAGGCT | SEQ ID NO: 147 |
| | Off-10 | AGGAAGCTGAGTGGCTAATGGTAA | SEQ ID NO: 97 | TCTGGTTTCCGTTCTCCAGTTCCA | SEQ ID NO: 148 |
| | Off-11 | CCTGAGAAAGCTAATACTGTCCAC | SEQ ID NO: 98 | TTCCCCTCCGAAAATCCCCTATCC | SEQ ID NO: 149 |
| | Off-12 | ATCCCCAAAACCCCTTATACCCTT | SEQ ID NO: 99 | GTACCCCAGGTGCTAAAAGGGTCT | SEQ ID NO: 150 |
| | Off-13 | GCTAAGGGGTCAGTTCTGCACTCA | SEQ ID NO: 100 | CAGTGCCCTCCCTGACAATGTCA | SEQ ID NO: 151 |
| | Off-14 | CTGCATCACCATTACTACAACACA | SEQ ID NO: 101 | TGAGATTGGGGTGCATCTCTGGAA | SEQ ID NO: 152 |
| | Off-15 | GAGTGAGCCATCACAGTTGCAGAT | SEQ ID NO: 102 | AGTCATCCTATAGCTCTGGACAGG | SEQ ID NO: 153 |
| | Off-16 | TGTACCTCAGCCTTGAGTTTGAGT | SEQ ID NO: 103 | GCTCATAGTCCTCTACTGGATGGA | SEQ ID NO: 154 |
| | Off-17 | GCCGATTGGGAGATAGTTTACACA | SEQ ID NO: 104 | GGGTGCCTAAGACACGTACTAAAG | SEQ ID NO: 155 |
| | Off-18 | ACGGGGGAGGGAGTAACTTAGCTA | SEQ ID NO: 105 | AATTACTGTCCCGCCAGGATGGA | SEQ ID NO: 156 |
| | Off-19 | AAGAGCAGTCAGTGCTCTTAACCA | SEQ ID NO: 106 | TGCCCTGAGACCAAAGGAATAAGA | SEQ ID NO: 157 |
| | Off-20 | GCAGGATGACAGAAATGCTTGTTG | SEQ ID NO: 107 | CCAGAAAGTGAGGTCTCATCTCCA | SEQ ID NO: 158 |
| | Off-21 | GCAGGATGACAGAAATGCTTGTTG | SEQ ID NO: 108 | CCAGAAAGTGAGGTCTCATCTCCA | SEQ ID NO: 159 |
| | Off-22 | GAGTGGCTCACTTAGCTTCTGCTA | SEQ ID NO: 109 | CGTCTTATCACTAGGGTTAAGGGT | SEQ ID NO: 160 |
| | Off-23 | CATCTGTTGTGGTGTTGAAAGCCA | SEQ ID NO: 110 | ATGACCACAGACCTACAACATGCA | SEQ ID NO: 161 |
| | Off-24 | CCATCCAATCTCTTCCTGGGAGAA | SEQ ID NO: 111 | CCCAGGATCCTCGTGTGTGTTACA | SEQ ID NO: 162 |
| | Off-25 | CCAGATGCAAACCACAGCATCCTA | SEQ ID NO: 112 | CTGCTGTGGCATCATGGTGCCTA | SEQ ID NO: 163 |
| | Off-26 | CCCAGAACCTGTGCTAAAGATTGA | SEQ ID NO: 113 | CAGGAGCCAACTGGGAAATAGACT | SEQ ID NO: 164 |
| | Off-27 | CTTTCCTTGTTTCCCCTCTGAAGA | SEQ ID NO: 114 | CACCAGCCAAAGAAAACACATGGT | SEQ ID NO: 165 |
| | Off-28 | CTTTCCTTGTTTCCCCTCTGAAGA | SEQ ID NO: 115 | CACCAGCCAAAGAAAACACATGGT | SEQ ID NO: 166 |
| | Off-29 | CTTTCCTTGTTTCCCCTCTGAAGA | SEQ ID NO: 116 | CACCAGCCAAAGAAAACACATGGT | SEQ ID NO: 167 |
| | Off-30 | CTTTCCTTGTTTCCCCTCTGAAGA | SEQ ID NO: 117 | CACCAGCCAAAGAAAACACATGGT | SEQ ID NO: 168 |
| | Off-31 | GTAGGCAAAGCATCCATACACACA | SEQ ID NO: 118 | CAAGGCAGCCAAGGATGTAGGAA | SEQ ID NO: 169 |
| | Off-32 | AATGCTATCCCGAAAGACCCCTAT | SEQ ID NO: 119 | CCTGGGACTAAACCACCAATCCAT | SEQ ID NO: 170 |
| | Off-33 | ATGGCCAAGCAATACTTATGCTGA | SEQ ID NO: 120 | AGCCTGGCATTTAGAAGTCAAGGA | SEQ ID NO: 171 |

2. Cell Culture and Transfection

Mouse C2C12 (ATCC, CRL-1722™) cells were maintained in DMEM supplemented with 4.5 g/L glucose, 4 mM glutamine, 1 mM sodium pyruvate, 10% fetal bovine serum and 100 units/mL streptomycin. The transfection of a plasmid was performed using Neon® Transfection according to the manufacturer's procedure (Life Technologies). Briefly, $2.5 \times 10^5$ cells were mixed with a total of 1 μg of plasmids (a plasmid encoding SpCas9 optimized for a human and a plasmid encoding a donor and sgRNA). Afterward, the cells were subjected to electrical shock using a 10 μL tip (Neon System) for 15 seconds at 1,150V for two pulses. Five days after transfection, the cells were harvested, and genomic DNA was extracted using a DNeasy Blood & Tissue kit (Qiagen).

3. Animals

Eight-week-old male C57BL/6 mice and mating pairs of rd12 mice (Stock no. 005379, The Jackson Laboratory) were purchased from Central Laboratory Animal and maintained under a 12-hour dark-light cycle. The rd12 mice were crossed with each other to produce offspring with a homozygous mutation in the Rpe65 gene.

4. T7E1 Assay

The target sites in the genomic DNA extracted from the transfected cells were amplified by polymerization chain reaction (PCR). Afterward, the PCR product was denatured and annealed using a thermal cycler, thereby forming heteroduplex DNA, and the resulting product was incubated with T7 endonuclease 1 (Toolgen Inc.) at 37° C. for 20 minutes, and analyzed by electrophoresis on 2% agarose gel.

5. Targeted Deep Sequencing

On-target and off-target sites in genomic DNA extracted from the transfected cells, retina or RPE were amplified by PCR. To quantify HDR frequencies, first PCR was performed using primers recognizing sequences outside of Rpe65-homology arms, and the PCR products were additionally amplified to generate amplicons for deep sequencing. The generated amplicons were sequenced using Miseq along with a TrueSeq HT dual index system (Illumina). The indel or HDR frequencies were quantified using Cas-Analyzer (www.rgenome.net).

6. In Silico Identification of Off-Target Sites

Potential off-target sites were identified using an in-silico tool, Off-finder (www.rgenome.net). Mouse genomic sites having a maximum of 3 bp mismatches were considered as off-target sites, and confirmed by targeted deep sequencing.

7. AAV Vector Construction and Viral Production

Sequences of human-optimized SpCas9 having a nuclear localization signal (NLS), a HA-tag and a bovine growth hormone poly-A tail and an EFS promoter were synthesized, and subcloned into an AAV2 inverted tandem repeat (ITR)-based plasmid using a NotI restriction site. In addition, for another AAV vector, sequences of the U6 promoter, TS4 sgRNA and Rpe65 donor were also synthesized and subcloned into an AAV2 ITR-based plasmid using the same restriction sites. In the Rpe65 donor sequences, five nucleotides were substituted without codon changes to prevent TS4 sgRNA-mediated cleavage and precisely distinguish knock-in sequences from endogenous genomic sequences. Recombinant AAV particles were produced using a helper adenovirus-free packaging system. Briefly, HEK293 cells were transfected with pAAV-ITR-EFS-SpCas9 or pAAV-ITR-TS4rd12-sgRNA-Rpe65 donor in addition to an AAV9-capsid plasmid and a helper plasmid. Three days after transfection, the cells were lysed, and the virus particles were purified by iodixanol gradient ultracentrifugation and concentrated to obtain titers of $10^{13}$ vg/ml or more.

8. Subretinal Injection of AAV

After deep anesthesia, AAV9-SpCas9 and AAV9-TS4$^{rd12}$ sgRNA-Rpe65-donor ($1 \times 10^{10}$ viral genomes/1 μL PBS and $1 \times 10^{11}$ viral genomes/1 μL PBS, respectively) were injected into the subretinal space of the mouse eye through the vitreous cavity using a Nanofil syringe with a 33-gauge blunt needle (World Precision Instruments Inc.) under a surgical microscope (Leica Microsystems Ltd.).

9. Electroretinography

Mice were dark-adapted for 16 hours and anesthetized. Afterward, pupils were dilated with an eye drop containing phenylephrine hydrochloride (5 mg/mL) and tropicamide (5 mg/mL). Full-field electroretinography was performed using the universal testing and electrophysiologic system 2000 (UTAS E-2000, LKC Technologies). Responses were recorded at 2 k gain using a notch filter at 60 Hz, and bandpass-filtered between 0.1 and 1500 Hz. The amplitude of an a-wave was measured from the baseline to the lowest negative voltage, whereas the peak b-wave amplitude was measured from the trough of the a-wave to the highest peak of the positive b-wave.

10. Immunofluorescence

At 6 weeks and 7 months after AAV-mediated delivery of SpCas9 and TS4$^{rd12}$ sgRNA-Rpe65-donor, paraffin blocks were prepared from extracted eyes. Thin sections were immunostained with an anti-HA antibody (1:1000, cat. no. 3F10, Roche) and an anti-Rpe65 antibody (1:1,000, cat. no. sc-73616, Santa Cruz), followed by treatment with Alexa Fluor 488 or 594 IgG (1:500, Thermo Fisher). Nuclear staining was performed using 4',6-diamidino-2-phenylindole dihydrochloride (Sigma). Afterward, slides were observed under a fluorescence microscope (Leica).

11. Histologic Evaluation

At 7 months after AAV-mediated delivery of SpCas9 and TS4$^{rd12}$ sgRNA-Rpe65-donor, paraffin blocks were prepared from extracted eyes, and thin sections were stained by H & E staining.

12. Quantitative PCR for AAV Genome Detection in Tissues

Quantitative PCR for determining an AAV genome copy number was performed using genomic DNA extracted from the retina or RPE. Genomic DNA concentrations were measured using a Quantus fluorometer together with the Quantifluor Dye system (Promega), and 50 ng of genomic DNA was then subjected to quantitative PCR analysis using the AAVpro Titration Kit (Takara). Thermocycling conditions are as follows: 95° C., 2 min, followed by 35 cycles of 95° C., 5 sec; 60° C., 30 sec. The number of AAV genome copies was calculated using a standard curve. The number of diploid mouse cells was calculated using a conversion factor of ~$1.6 \times 10^4$ diploid cells per 100 μg of genomic DNA.

13. Statistics

All group results are expressed as means±SEM, unless otherwise stated. Statistical significance, compared with untreated controls, is shown with *P<0.05, P<0.01 and *P<0.001 in the figures and figure legends. Statistical analysis was performed on GraphPad PRISM 5.

Example 1. HDR-Mediated Genome Editing of Rpe65 by CRISPR/Cas9 In Vitro

Figure 2:
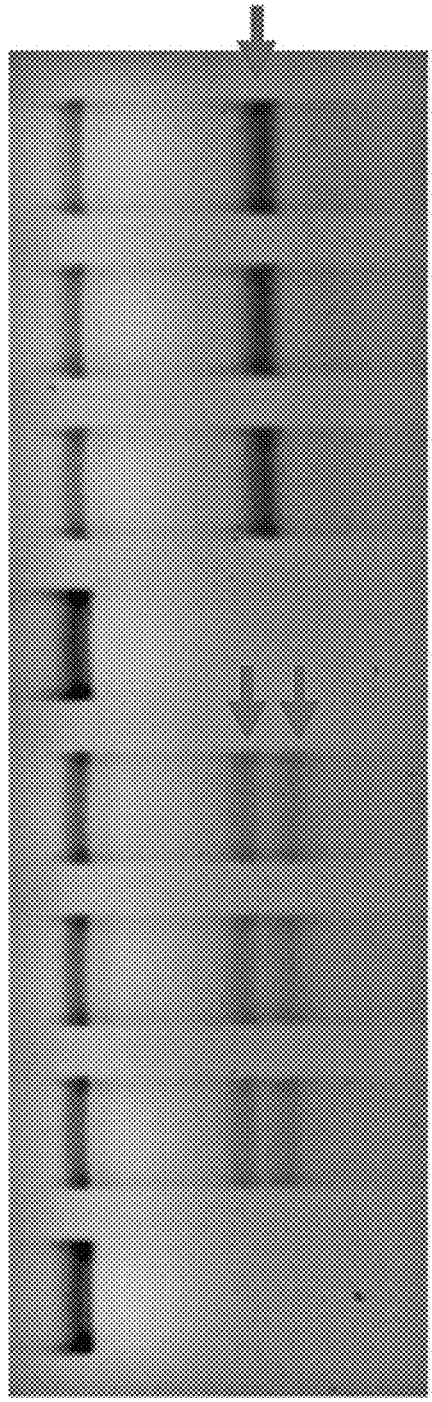
FIG. 2 is an image of confirming TS1 sgRNA and TS4 sgRNA-induced mutations in C2C12 cells detected by a T7E1 assay, in which a control (Ctrl) is treated with only Cas9, and a DNA fragment cleaved by T7E1 is indicated by an arrow.

Initial sgRNA screening was performed using a mouse C2C12 cell line (Rpe65 wt/wt). Due to technical convenience and because sgRNA screened in the mouse C2C12 cell line can be used in rd12 mice after one nucleotide change, the mouse C2C12 cell line (Rpe65 wt/wt) was used instead of rd12 mouse-derived cells. Among 11 potential candidates tested, TS1 sgRNA and TS4 sgRNA showed the most effective indel frequencies as measured by targeted deep sequencing (FIG. 1). Editing rates were confirmed by T7 endonuclease 1 assay (FIG. 2).

Figure 3:
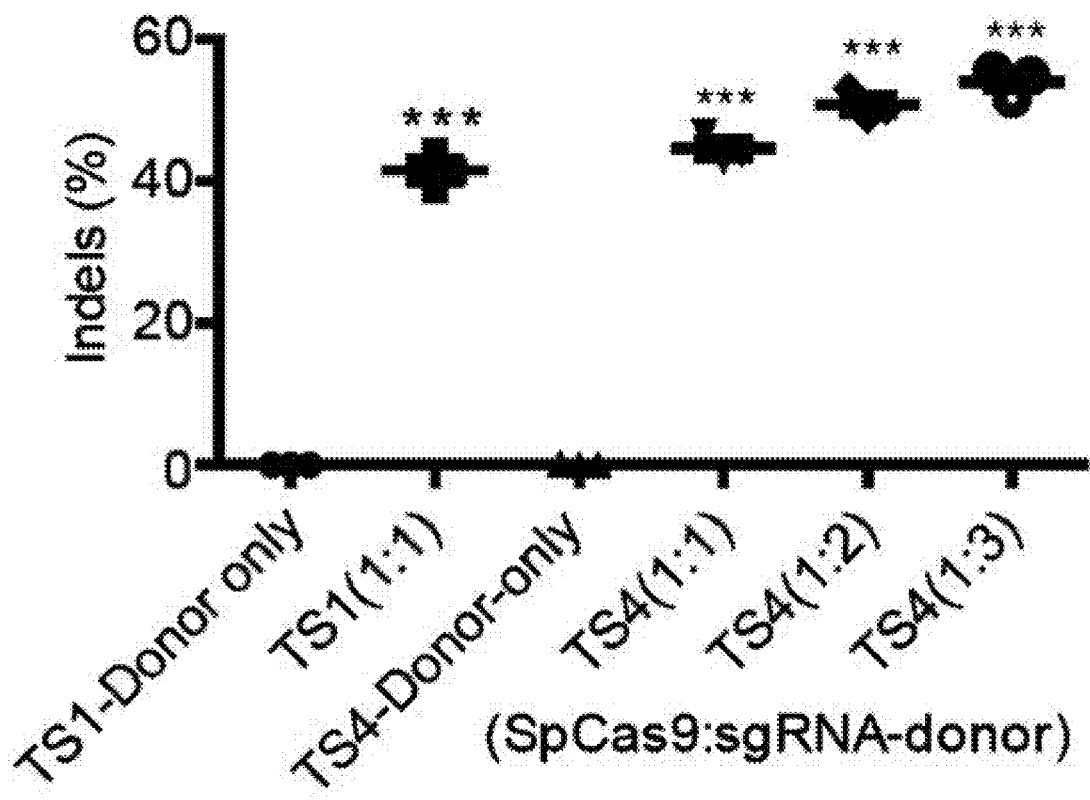
FIG. 3 is a graph showing indel frequencies measured by targeted deep sequencing (n=3), in which ratios of SpCas9 and Rpe65-donor are indicated in parentheses. An error bar represents SEM, and statistical significance is represented as ***P<0.001 by one-way ANOVA and a Student's t test for TS1 sgRNA in addition to a post-hoc Bonferroni's test for TS4 sgRNA.
Figure 4:
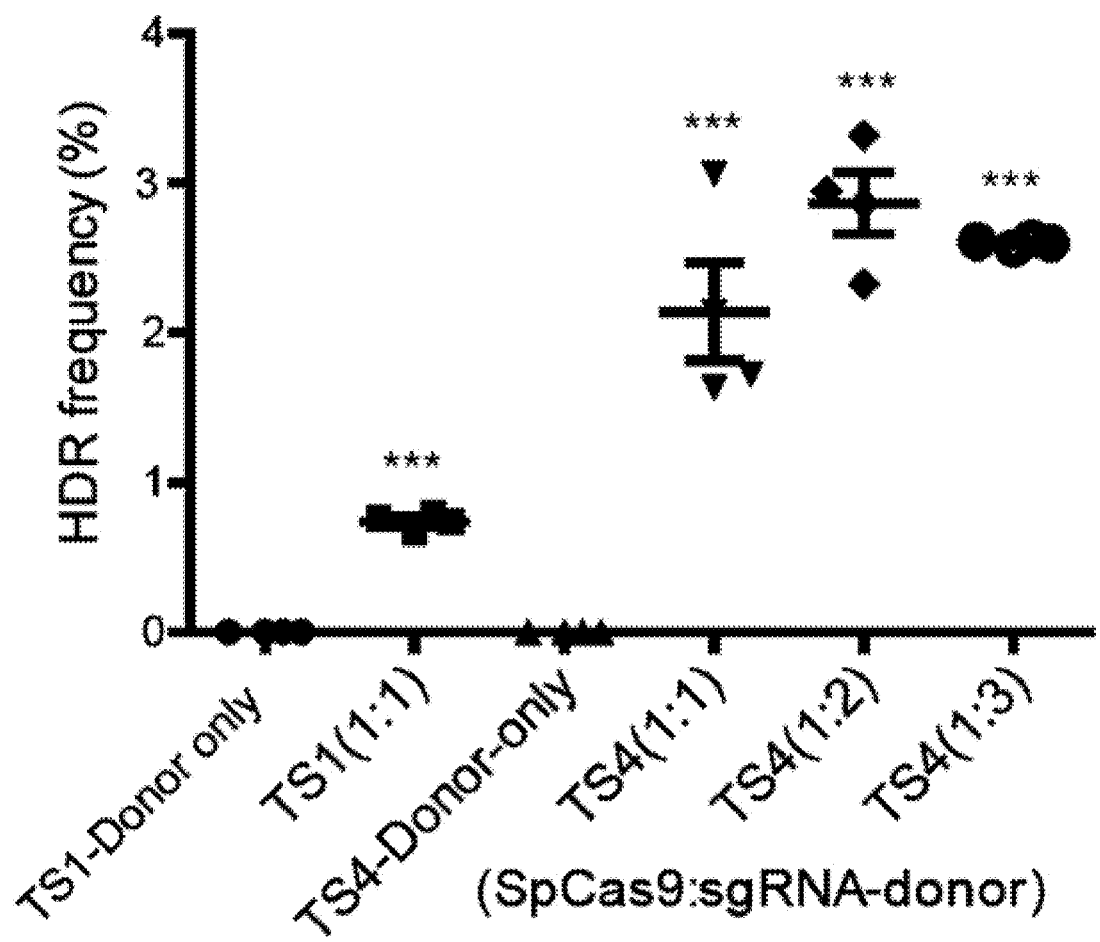
FIG. 4 is a graph showing HDR frequencies in regions corresponding to rd12 mutations detected by targeted deep sequencing (n=4), in which ratios of SpCas9 and Rpe65-donor are indicated in parentheses. An error bar represents SEM, and statistical significance is represented as ***P<0.001 by one-way ANOVA and a Student's t test for TS1 sgRNA in addition to a post-hoc Bonferroni's test for TS4 sgRNA.
Figure 6:
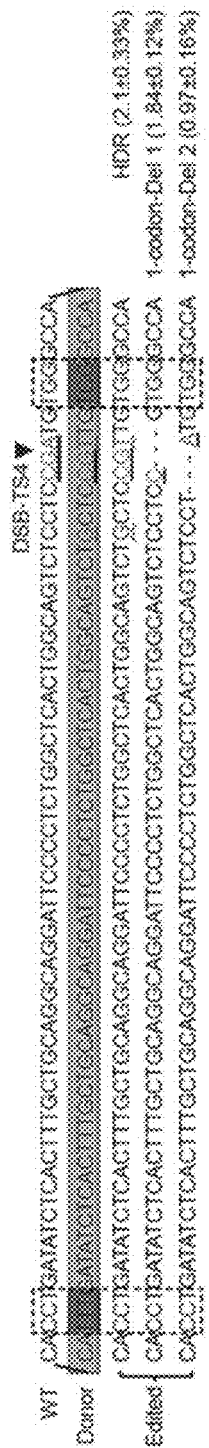
FIG. 6 is an image showing a nucleotide sequence representing an Rpe65 donor template (SEQ ID NO: 180) and a change induced by TS4 sgRNA, in which an inverted triangle (▼) indicates a DSB position induced by TS4 sgRNA, a sequence corresponding to a premature termination codon of a rd12 mouse is underlined (straight), and PAM is indicated by square box (dotted line). In addition, the synonymous mutation of a donor is wave-underlined, HDR and 1-codon deletion frequencies are values (n=3) induced by SpCas9 and Rpe65-donor templates, which are delivered in a 1:1 ratio. The WT sequence is SEQ ID NO: 181, and the edited sequences are SEQ ID NOs: 182 to 184 (HDR to 1-codon-Del 2 order).

Subsequently, HDR frequencies induced by TS1 sgRNA and TS4 sgRNA were tested. To this end, a 1.8 kb Rpe65 donor template was introduced into a C2C12 cell line together with SpCas and one of the two sgRNAs. To prevent donor cleavage and recleavage of a Rpe65 locus repaired after HDR, synonymous mutations were introduced into the donor template sequence (FIGS. 1 and 6). Indel frequencies induced by the two sgRNAs were similar, but HDR frequencies showed a significant difference in a sequence corresponding to the premature termination codon of a rd12 mouse (FIGS. 3 and 4). HDR was induced by TS1 sgRNA at a frequency of 1.73±0.17%. Less than half of the HDR events (0.74±0.04%) were associated with potential correction of rd12 mutations, and the remainder (0.98±0.12%) occurred near the TS1-induced double-strand break (DSB) position. In contrast, TS4 sgRNA has a significantly high frequency of one dominant HDR associated with the correction (>2%) of rd12 mutations (FIG. 4). Particularly, the high frequency of HDR induced by TS4 sgRNA was unrelated to a ratio of donor with respect to SpCas9 (FIG. 4).

Figure 5:
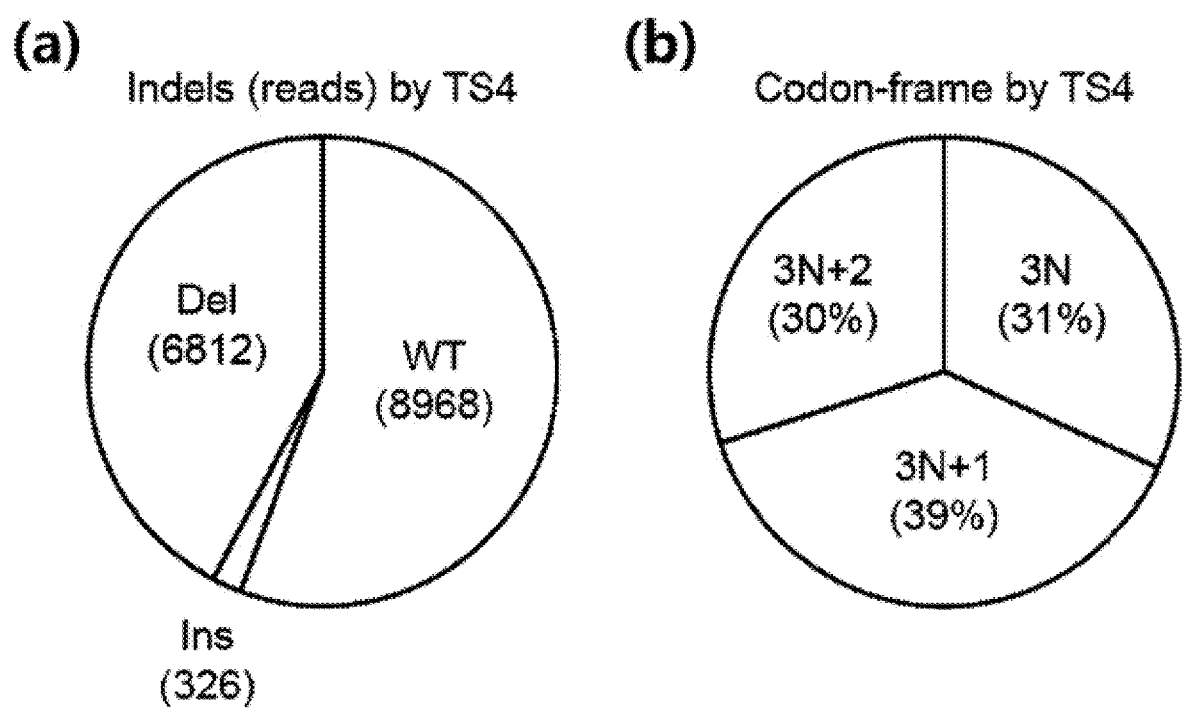
FIGS. 5A and 5B shows mean values of the number of deep sequencing reads in different categories, in which (a) is a graph showing the pattern of indels induced by TS4 sgRNA in several categories (n=3), indicating approximately 40% deletions, (b) is a graph showing different patterns of in-frame indels and out-of-frame indels, which are induced by TS4 sgRNA, divided into several categories (3N: one codon; 3N+1: one codon+1 nucleotide; 3N+2: one codon+2 nucleotides) (n=3). Here, one third of the deletions were confirmed as in-frame indels.

Interestingly, when NHEJ was analyzed by deep sequencing, TS4 sgRNA-mediated indels were dominated by deletions, and approximately one third of the mutations corresponded to in-frame indels (FIG. 5). Among the in-frame indels, 1-codon deletions accounted for 2.8% of total reads (FIG. 6). Since the in-frame indels were able to cause the removal of the premature Rpe65 termination codon in rd12 mice, it seems that NHEJ-mediated editing will also contribute to the therapeutic effect of CRISPR/Cas9. These results show that a sgRNA sequence optimized for therapeutic CRISPR/Cas9-mediated genome manipulation to treat LCA was identified.

Example 2. In Vivo Genome Editing of Rpe65 by the Dual AAV System

Figure 7:
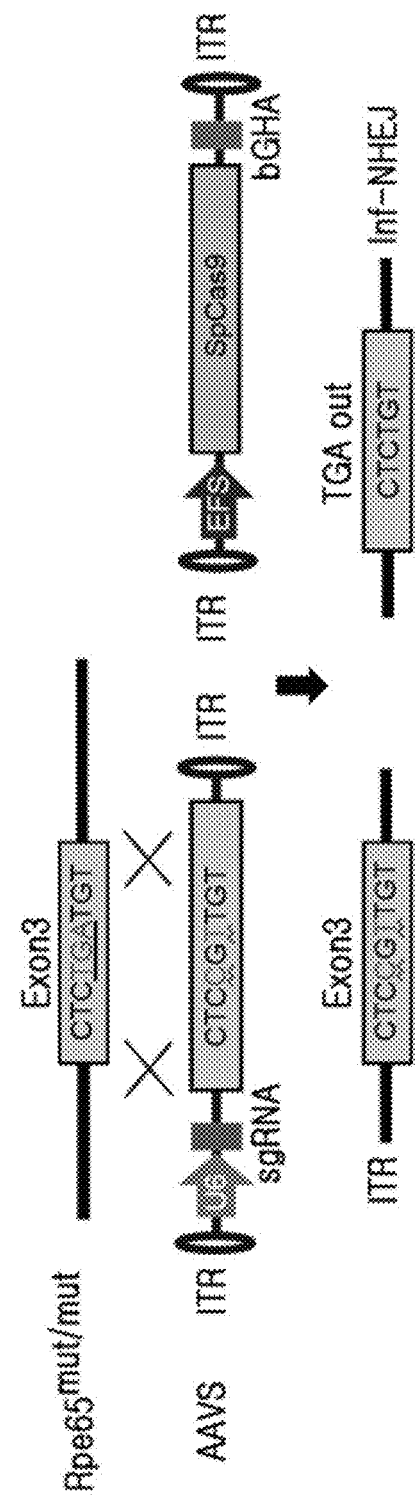
FIG. 7 is a schematic diagram of the dual AAV strategy for CRISPR/Cas9-mediated therapeutic correction of the nonsense mutation of Rpe65 in rd12 mice, in which the premature termination codon (straight-underlined) of Rpe65 is generated by a C→T mutation at exon 3, an AAV vector uses a U6 promoter to express both of sgRNA and a donor template (synonymous mutation is wave-underlined) and an EFS promoter to express SpCas9. Therapeutic gene editing may be induced from HDR-mediated precise editing (HDR) or in-frame NHEJ (Inf-NHEJ).

To evaluate the therapeutic efficacy of CRISPR/Cas9-mediated editing of the Rpe65 nonsense mutation in a disease model, one nucleotide of TS4 sgRNA for designing TS4$^{rd12}$ sgRNA was changed. The designed TS4$^{rd12}$ sgRNA perfectly matched the Rpe65 exon 3 mutant locus in rd12 mice. All required manipulation components were incorporated into two separate AAVs (AAV-SpCas9 and AAV-TS4$^{rd12}$ sgRNA-Rpe65-donor, hereinafter AAV-TS4$^{rd12}$ sgRNA-Rpe65-donor was referred to as AAV-TS4$^{rd12}$-donor), and in vivo delivery was performed using a dual AAV system (FIG. 7).

Figure 8:
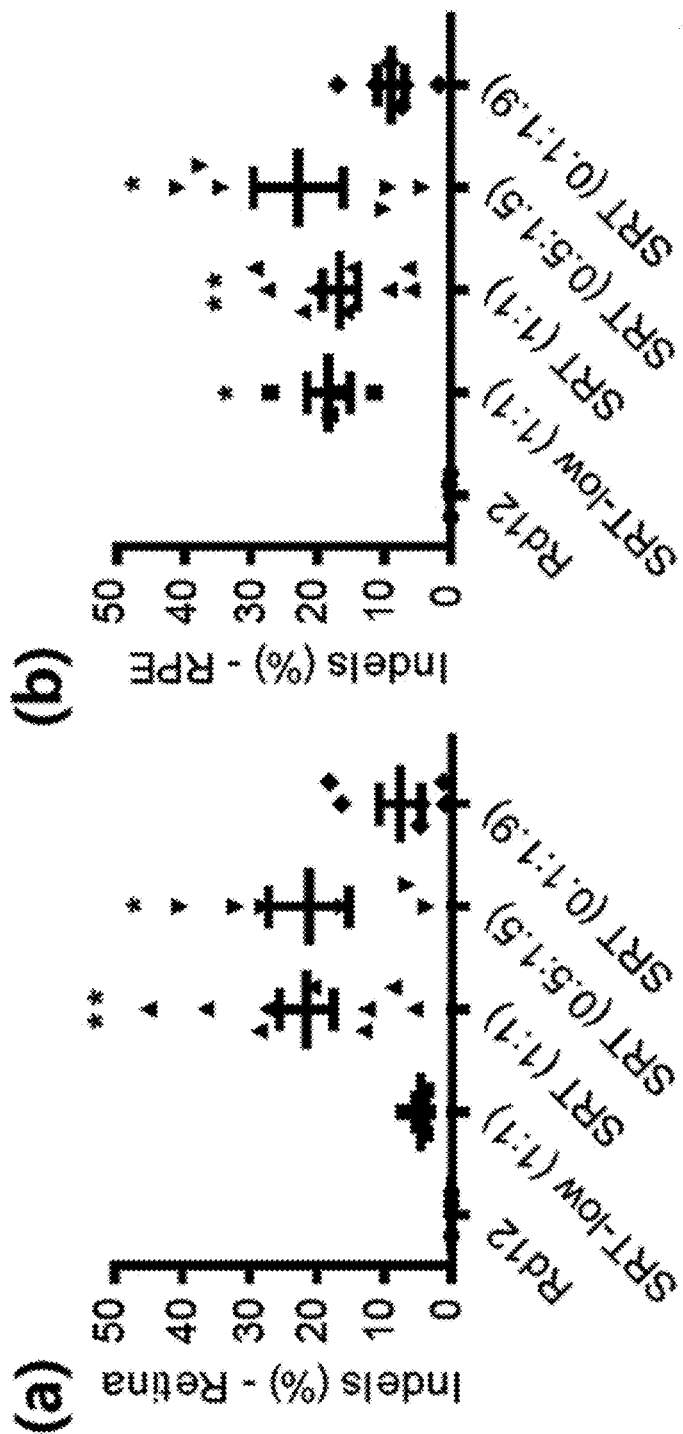
FIGS. 8A and 8B is a graph showing indel frequencies measured by targeted deep sequencing in the retina (a) and RPE (b) of rd12 mice at 4 weeks after the injection of high-dose (total $2 \times 10^{11}$ vg/eye) and low-dose (total $2 \times 10^{10}$ vg/eye) AAV, in which ratios of SpCas9 to TS4$^{rd12}$ sgRNA-Rpe65-donor are indicated in parentheses.
Figure 9:
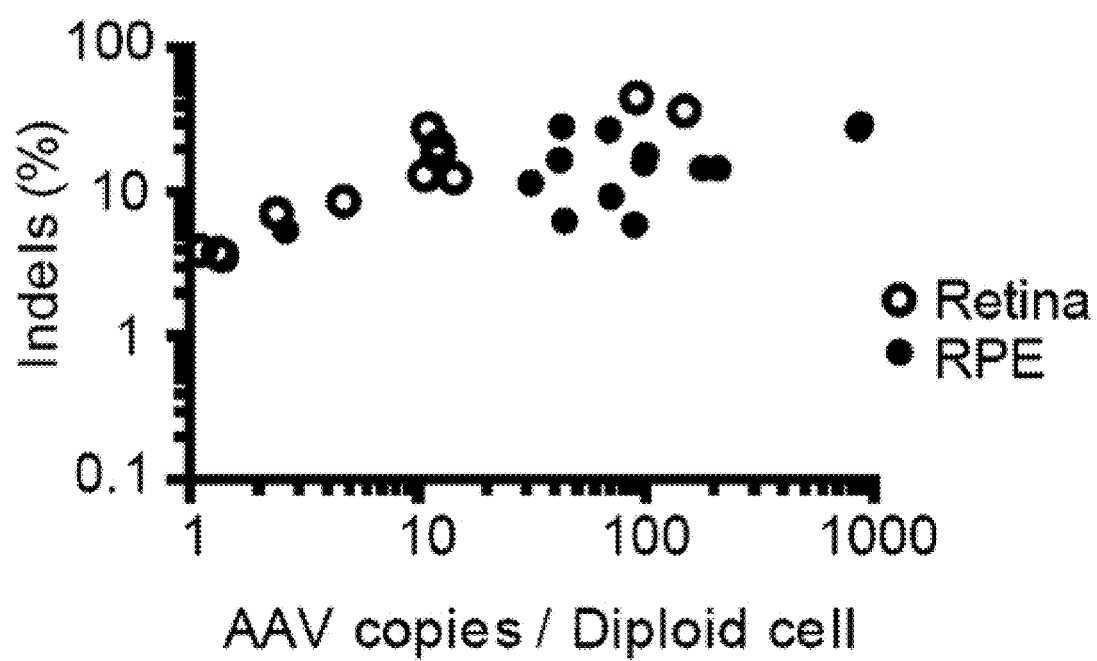
FIG. 9 is a graph showing the correlation between the AAV copy number per diploid cell and indel frequency.

When a total of 2×10$^{11}$ vg of AAV9 was mixed at 1:1 (AAV-EFS-SpCas9:AAV-RPE65-sgRNA-donor) and administered by subretinal injection, approximately 28% indels were identified in both of the RPE and retina, indicating that AAV can be used to efficiently correct RPE and retinal cells. Particularly, it was confirmed that HDR caused by the RPE65 donor occurs in the RPE, and approximately 1.4% HDR occurs in a total of 6 mice. To this end, it can be expected that RPE65 having a normal function can be expressed by HDR-mediated gene correction (FIG. 7). To obtain the maximum genome manipulation results, a ratio of AAV components was optimized by changing the two AAV concentrations. Through subretinal (SRT) injection into 3-week-old rd12 mice, low-dose (a total of 2×10$^{10}$ vector genomes (vg) per eye) or high-dose (a total of 2×10$^{11}$ vg per eye) AAV were administered. Four weeks after AAV treatment, the target site of Rpe65 was analyzed by deep sequencing using cells obtained from the retina and RPE. SRT injection resulted in indel rates reaching up to 20% in the retina and RPE, but this varied according to various parameters (FIG. 8). Low-dose SRT injection (SRT-low) resulted in low and high indel rates in the retina and RPE, respectively. These results show that SRT administration of AAV is more efficient in the RPE than in the retina, which was confirmed by a higher AAV copy number per diploid cell in the RPE (FIG. 9). Because a previous study showed that the use of sgRNA with a donor 10 times higher than Cas9 in a mouse model of liver disease induced an increase in correction, compared with AAV-SpCas9, an excessive amount of AAV-TS4$^{rd12}$-donor (AAV-SpCas9:AAV-TS4$^{rd12}$-donor=0.1:1.9) was tested, and after SRT administration, low indel frequencies in both tissues were shown (FIG. 8). Collectively, the results show that SRT delivery efficiency was efficient for inducing in vivo Rpe65 editing, and the sgRNA ratio to Cas9 is a critical factor for optimized manipulation.

Example 3. In Vivo Correction of Rpe65 Mutation in Rd12 Mice

Figure 10:
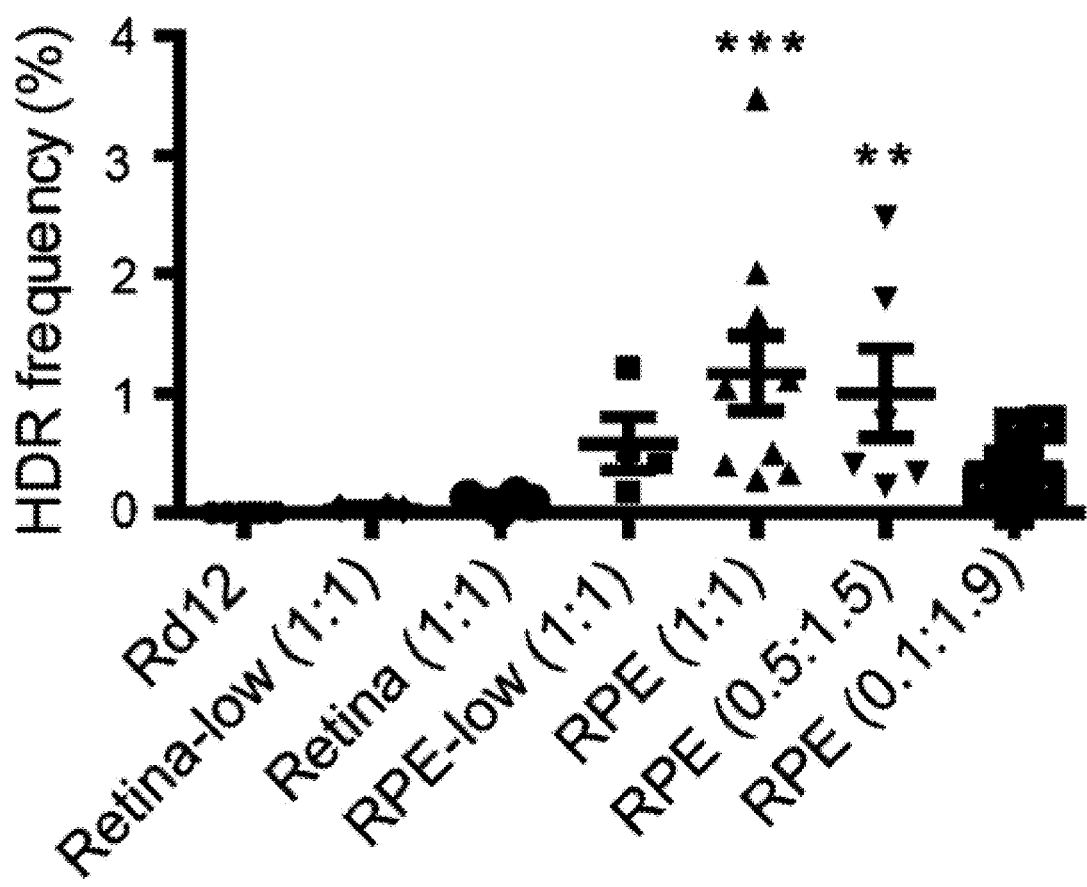
FIG. 10 is a graph showing therapeutic HDR frequencies at the C→T mutation site in the retina and RPE of rd12 mice at 4 weeks after injection.
Figure 11:
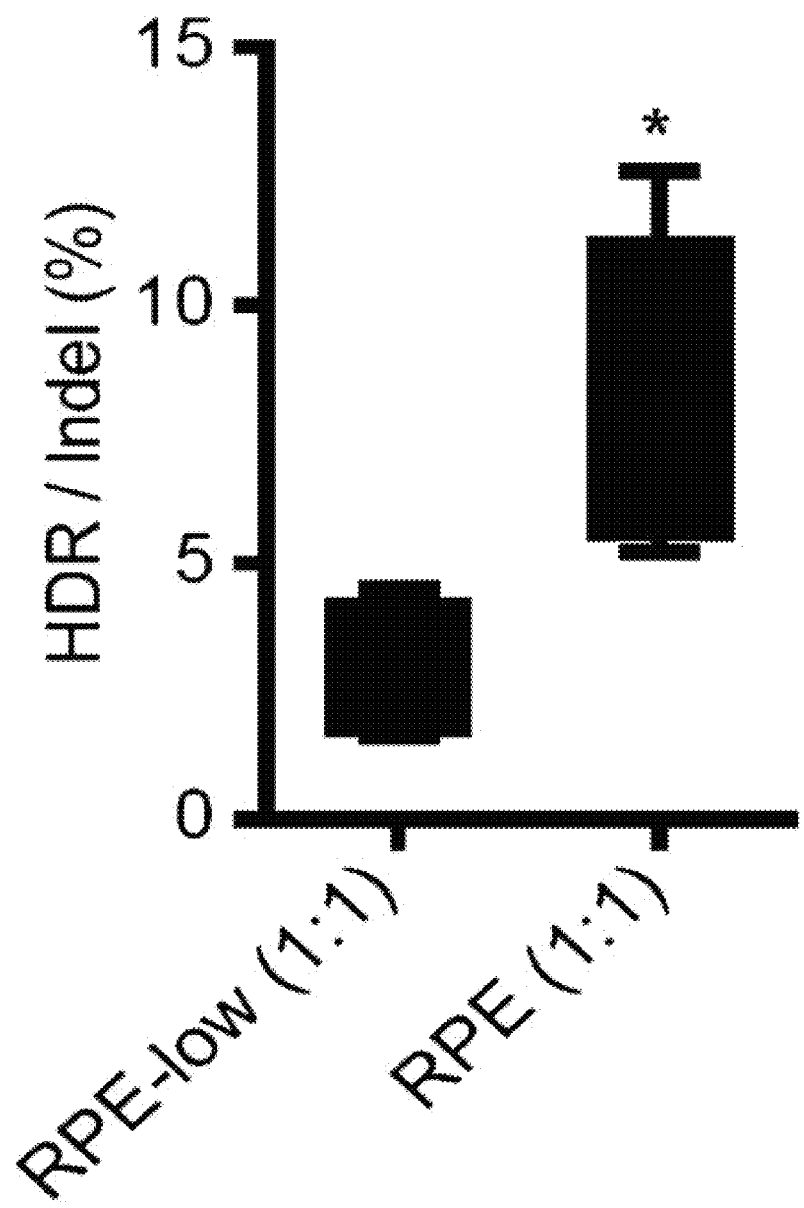
FIG. 11 is a graph showing a ratio of indel frequencies to HDR, which was obtained by subretinally injecting the 1:1 ratio of SpCas9 and TS4$^{rd12}$ sgRNA-Rpe65-donor at a high or low dose (n=4).
Figure 12:
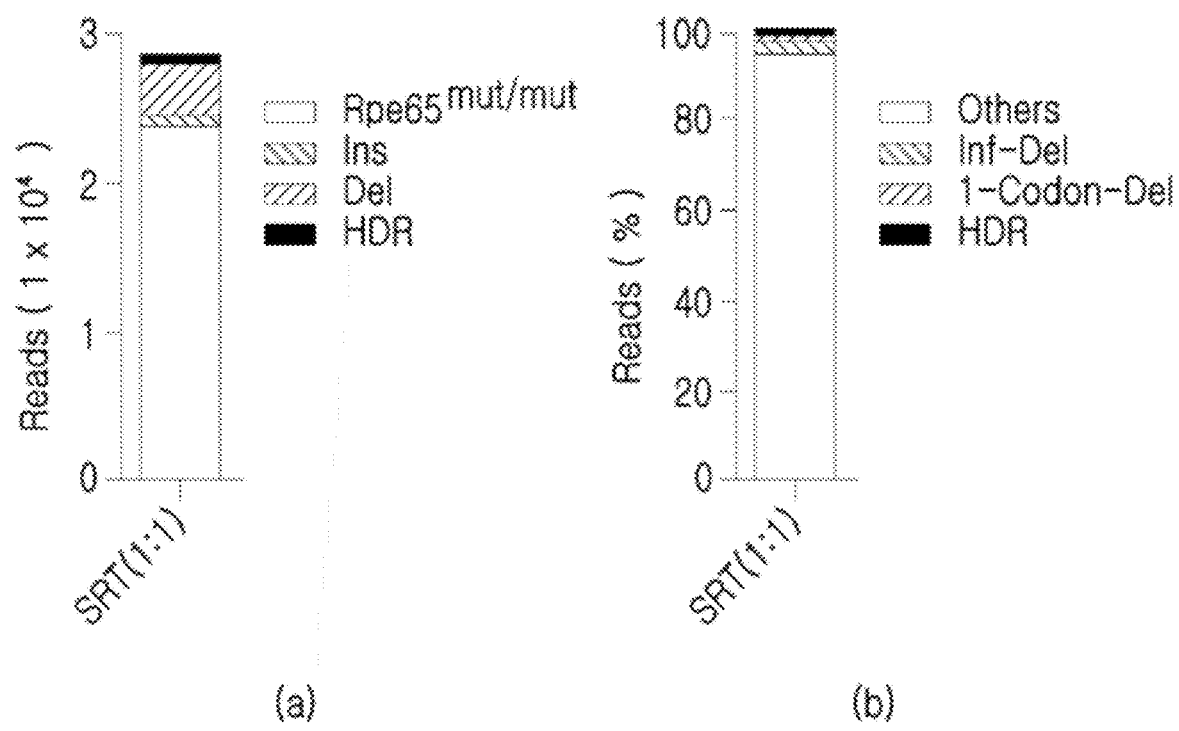
FIGS. 12A and 12B shows a graph (a) showing the mean value of the number of deep sequencing reads which include insertions, deletions or HDRs in AAV-treated RPE and a graph (b) showing the mean percentage of in-frame deletions, 1-codon deletions or HDRs, which were obtained by subretinally injecting the 1:1 ratio of SpCas9 and TS4$^{rd12}$ sgRNA-Rpe65-donor at a high or low dose (n=10). Rpe65mut/mut or Others represents an untreated control, Ins represents insertion, Del represents deletion, and Inf-Del represents in-frame deletion.
Figure 13:
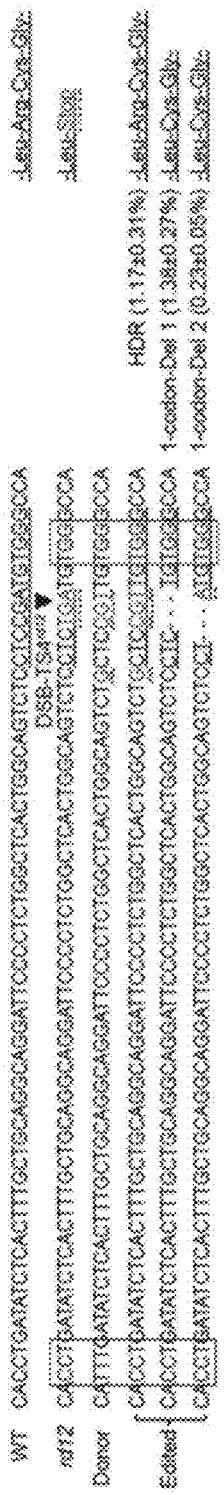
FIG. 13 is an image showing a TS4$^{rd12}$ sgRNA-induced change to AAV-treated RPE and a nucleotide sequence representing a Rpe65 donor template (SEQ ID NO: 180), which are obtained by subretinally injecting the 1:1 ratio of SpCas9 and TS4$^{rd12}$ sgRNA-Rpe65-donor at a high or low dose (n=10). Here, an inverted triangle (▼) indicates a DSB location induced by TS4 sgRNA, a sequence corresponding to the premature termination codon of the rd12 mouse is dot-underlined, and PAM is indicated by a square box. In addition, the synonymous mutation of a donor is wave-underlined, and a nucleotide sequence including the premature termination codon and an amino acid sequence corresponding thereto are underlined (straight). The WT sequence is SEQ ID NO: 181, and the rd12 sequence is SEQ ID NO: 185. The edited sequences are SEQ ID NOs: 186 to 188 (HDR to 1-codon-Del 2 order).

After AAV treatment in rd12 mice, HDR events near the pathogenic C-to-T mutation of Rpe65 in the retina and RPE were analyzed. The HDR events were clearly observed in the RPE, but not in the retina (FIG. 10). Although indel frequencies were comparable in the low-dose and high-dose AAV-treated RPE using a 1:1 ratio of AAV-TS4$^{rd12}$-donor to AAV-SpCas9 (FIG. 8), the HDR events were more frequently shown in the high-dose administered group (high dose, 1.17±0.31%; low dose, 0.59±0.22%) (FIG. 10). These results are similar to those observed in CRISPR-mediated correction of an ornithine transcarbamylase gene in hepatic cells in previous studies. In addition, by the analysis of a HDR-to-indel ratio, the HDR events were approximately three times more frequent in the high dose-treated group (FIG. 11). Successful HDR (1.01±0.38%) was also induced when the ratio of AAV-SpCas9:AAV-TS4$^{rd12}$-donor was 0.5:1.5 (FIG. 10). Significantly, because most HDR events resulted in a precise correction of the T-to-C mutation, as a result, a protein sequence was the same as that of wild-type Rpe65 (FIG. 13). In addition, as a result of characterization of NHEJ-mediated manipulation in the RPE, in-frame deletions occurred at a frequency of 3.83%, and 1-codon deletions resulting in the removal of the premature termination codon in rd12 mice occurred at a frequency of 1.61% (FIGS. 12 and 13).

Figure 14:
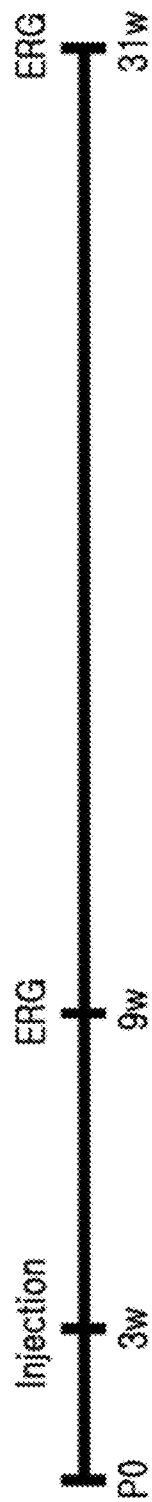
FIG. 14 shows the overview of animal experiments, in which time points of SRT injection and electroretinography are indicated (P0: postnatal day 0; EGR: electroretinography; W: week).
Figure 15:
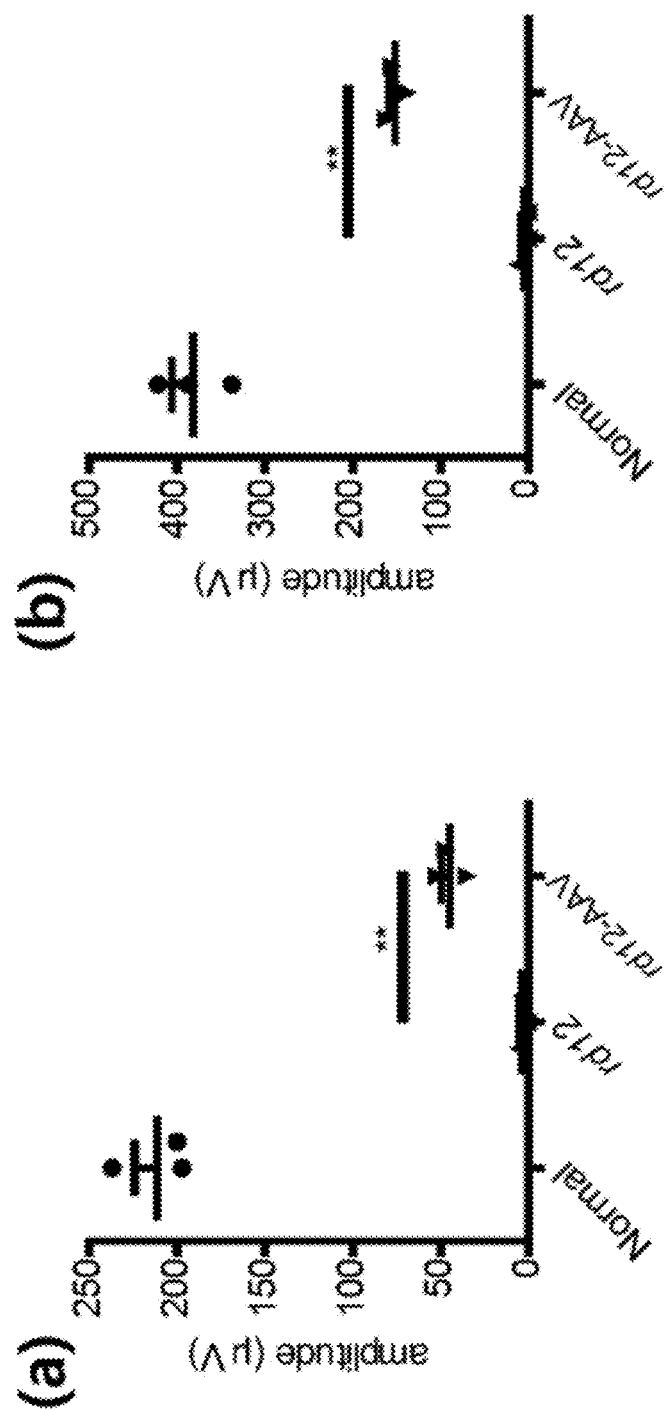
FIGS. 15A and 15B is a graph showing the amplitudes of optical responses in dark adaptation at 6 weeks after injection (n=4), in which (a) relates to the amplitudes of scotopic a-waves, and (b) relates to the amplitudes of scotopic b-waves (Normal: C57BL/6; rd12: untreated rd12 mouse; rd12-AAV: rd12 mouse treated by subretinally injecting the 1:1 ratio of SpCas9 and TS4$^{rd12}$ sgRNA-Rpe65-donor). Scale bar, 20 μm. *P<0.05; **P<0.01 by Student's t test.
Figure 16:
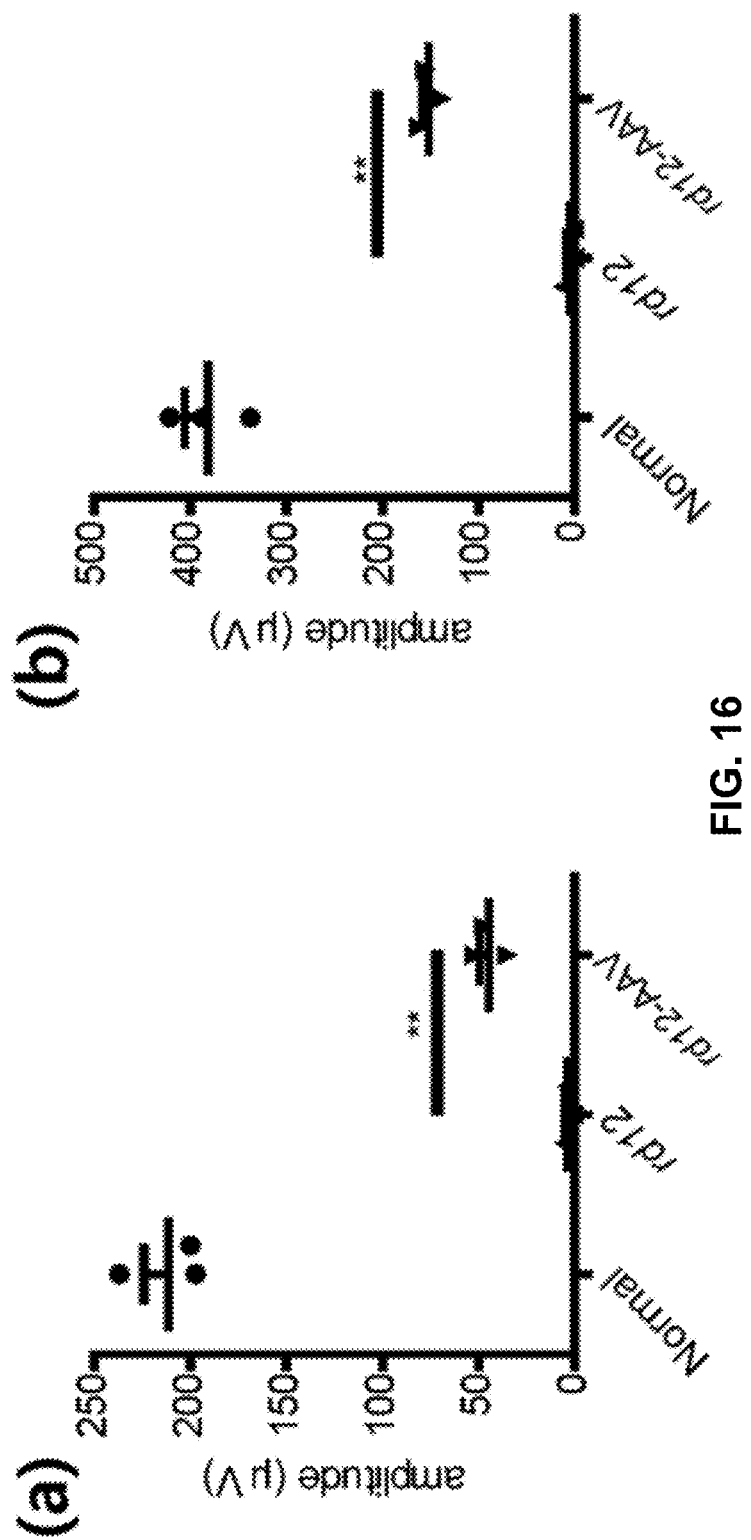
FIGS. 16A and 16B is graph showing the amplitudes of optical responses in dark adaptation at 7 months after injection (n=4), in which (a) relates to the amplitude of scotopic a-waves, and (b) relates to the amplitude of scotopic b-waves (Normal: C57BL/6; rd12: untreated rd12 mouse; rd12-AAV: rd12 mouse treated by subretinally injecting SpCas9 and TS4$^{rd12}$ sgRNA-Rpe65-donor at a ratio of 1:1). Scale bar, 20 μm. *P<0.05; **P<0.01 by Student's t test.

Example 4. Improved Retinal Function by HDR-Mediated Correction of the Rpe65 Gene in Rd12 Mice To investigate the therapeutic effects of HDR-mediated Rpe65 gene correction in rd12 mice, 6 weeks and 7 months after SRT injection of AAV, dark-adapted electroretinography was performed (FIG. 14). In electroretinography, rd12 mice showed considerably weaker dark-adapted light responses compared with age-matched normal C57BL/6 mice. In contrast, definite responses were identified in rd12 mice treated with AAV at 6 weeks after SRT injection (FIG. 15). Electrical responses were maintained for up to 7 months after initial injection (FIG. 16). The measured dark adaptation (scotopic) a- and b-wave amplitudes were 21.2±4.1% and 39.8±3.2% of those of normal C57BL/6 mice.

Figure 17:
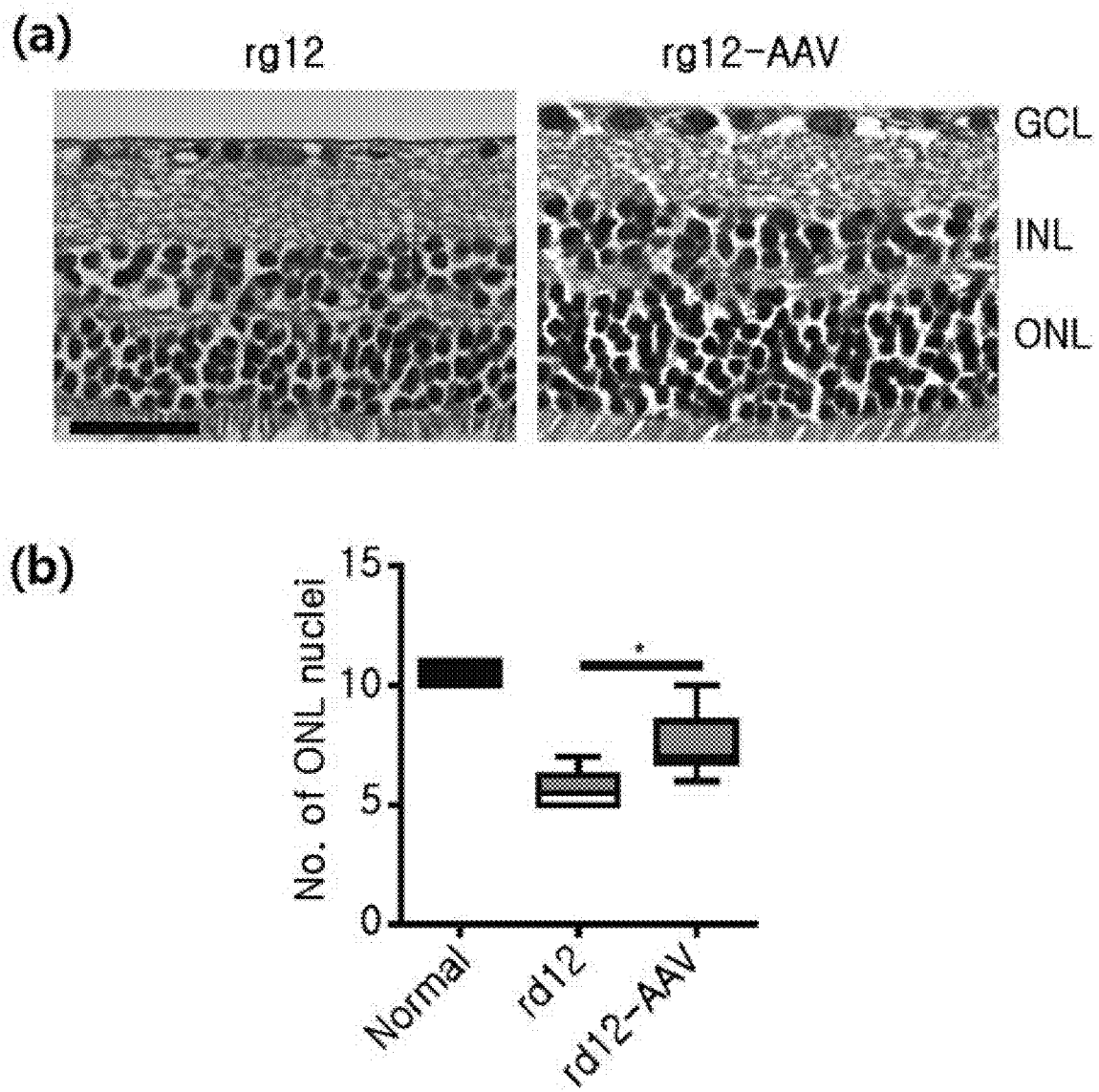
FIGS. 17A and 17B shows H & E images (a) of retinal tissues from rd12 mice which are treated by SRT injection of the 1:1 ratio of SpCas9 and TS4$^{rd12}$ sgRNA-Rpe65-donor at 7 months after injection or not treated, and a graph showing the number of nuclear layers of an outer nuclear layer (GCL: ganglion cell layer; INL: inner nuclear layer; ONL: outer nuclear layer; rd12: untreated rd12 mouse; rd12-AAV: rd12 mouse treated by subretinally injecting the 1:1 ratio of SpCas9 and TS4$^{rd12}$ sgRNA-Rpe65-donor). Scale bar, 20 μm. *P<0.05; **P<0.01 by Student's t test.
Figure 18:
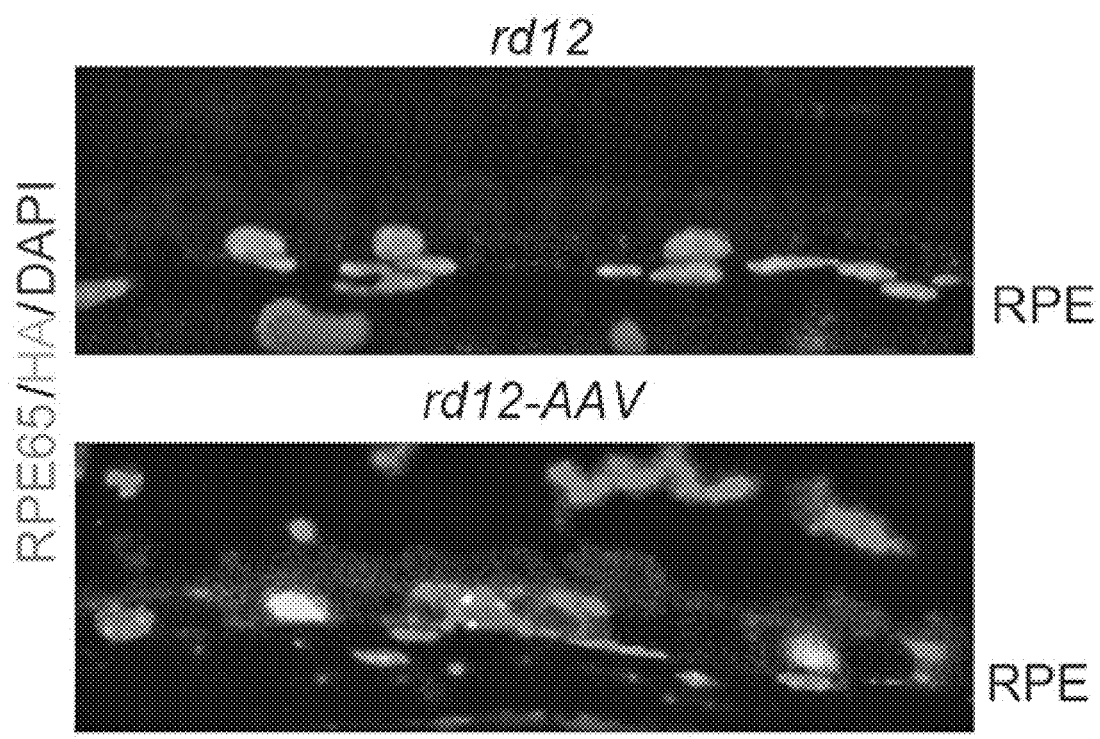
FIG. 18 is an image showing Rpe65 and HA expression in the RPE layer of rd12 mice (rd12: untreated rd12 mouse; rd12 mouse treated by subretinally injecting the 1:1 ratio of SpCas9 and TS4$^{rd12}$ sgRNA-Rpe65-donor). Scale bar, 20 μm.

Example 5. Recovered Rpe65 Expression and Attenuation of Retinal Degeneration HDR-mediated Rpe65 gene correction prevented the loss of neurons in the outer nuclear layer (FIG. 17). Six weeks after injection, AAV treatment restored Rpe65 expression in RPE cells (FIG. 18).

Example 6. In-Frame Editing of Human RPE65

Figure 19:
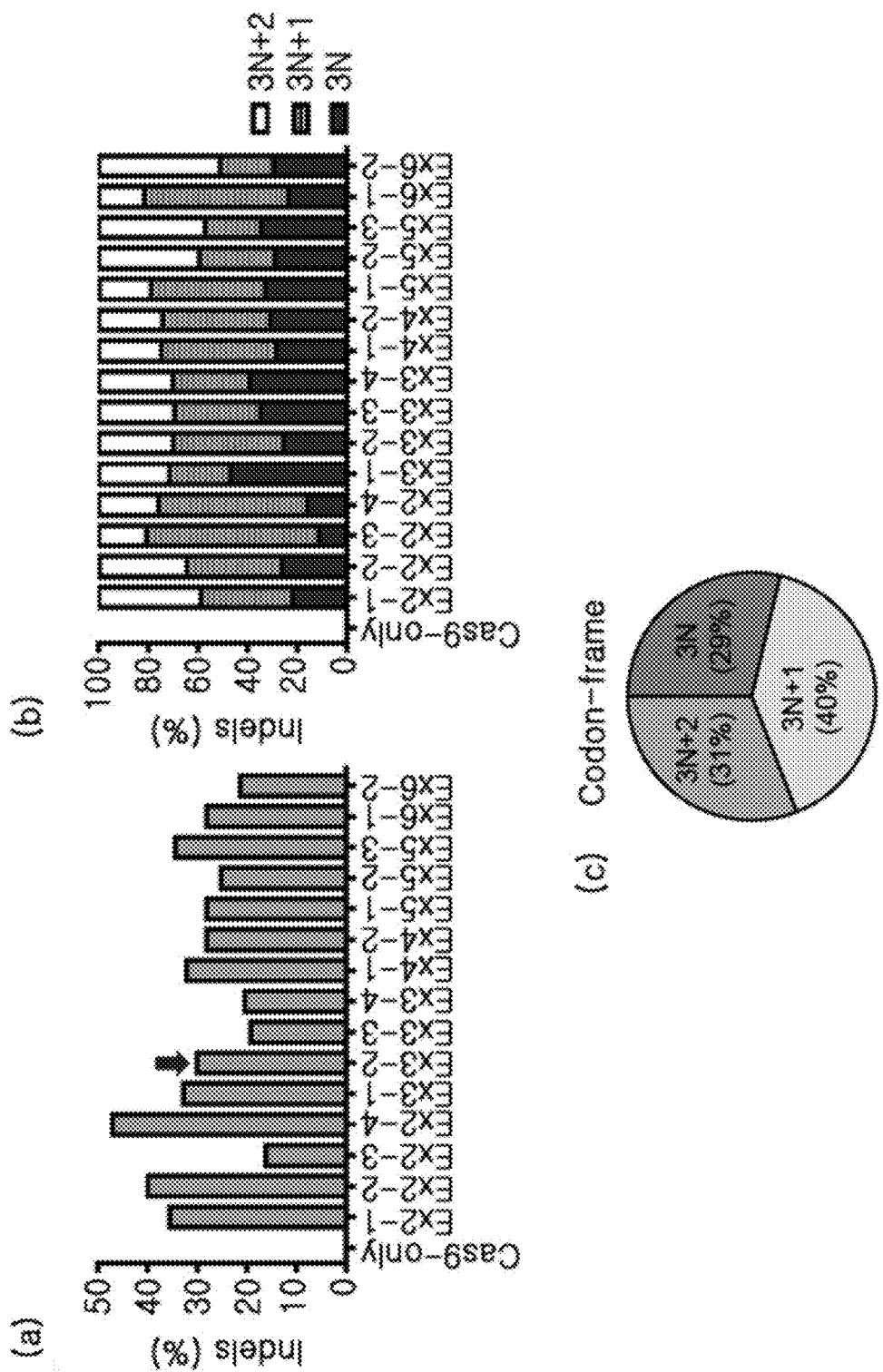
FIG. 19 also shows a graph (c) indicating percentages of in-frame and out-of-frame indels at 16 RPE65 target sites.

Substantial in-frame manipulation occurred in human RPE65 due to various sgRNAs (FIG. 19), and such a result demonstrates the clinical potential of NHEJ-mediated manipulation of RPE65, in addition to HDR-mediated correction.

Example 7. Analysis of Potential Off-Target Sites and Retinal Structure

Figure 21:
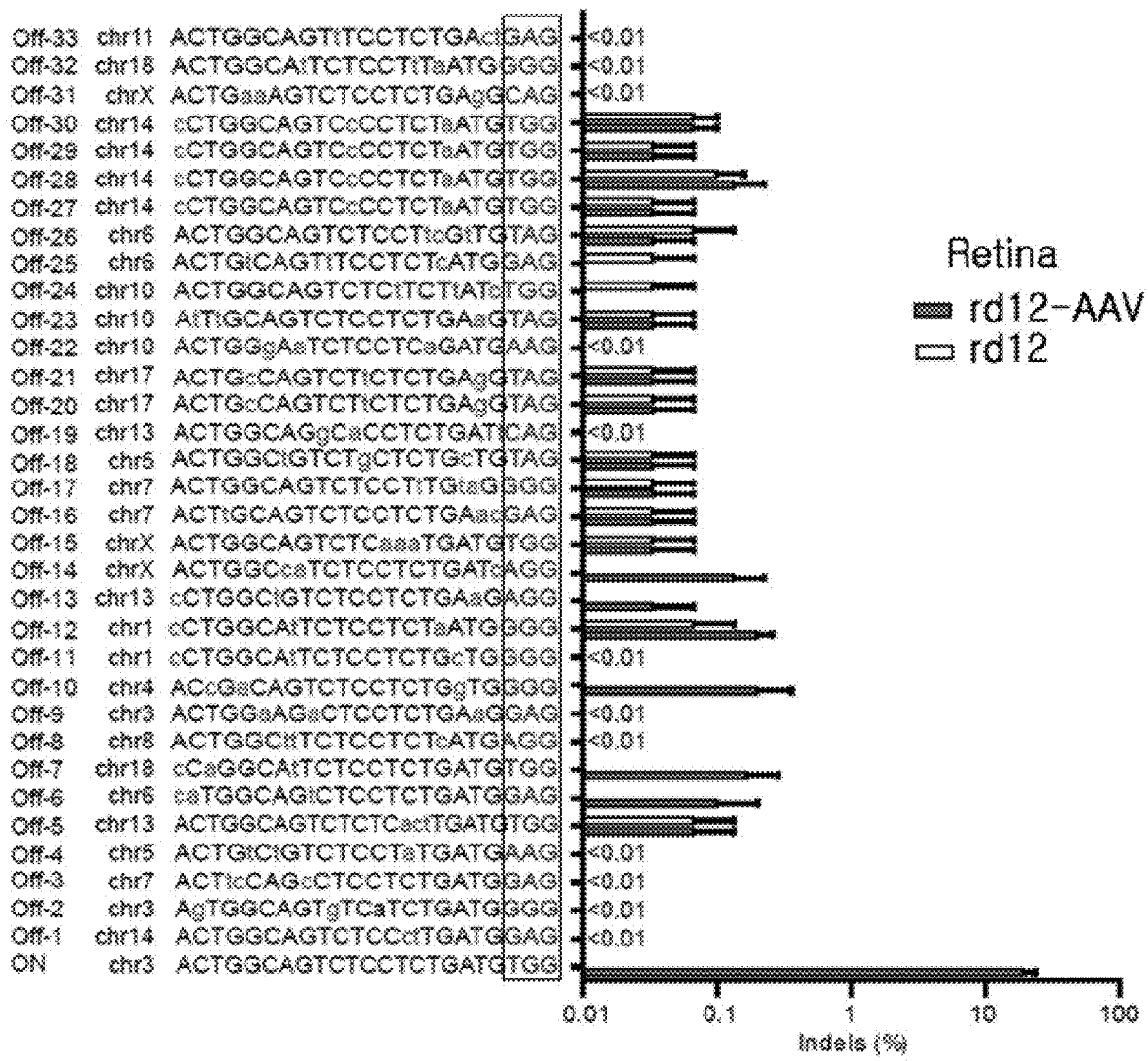
FIG. 21 shows the list of potential off-target sites with respect to 33 homologous regions which are different from TS4rd12 target sties by up to 3 nucleotides in an AAV-treated retina and a graph showing targeted deep sequencing results, in which mismatched nucleotides relative to an on-target site are indicated in lowercase letters and a PAM sequence is indicated by a square box. The on-target sequence is SEQ ID NO: 172, and the off-target sequences are SEQ ID NOs: 192 to 224 (Off-1 to Off-33 order).
Figure 22:
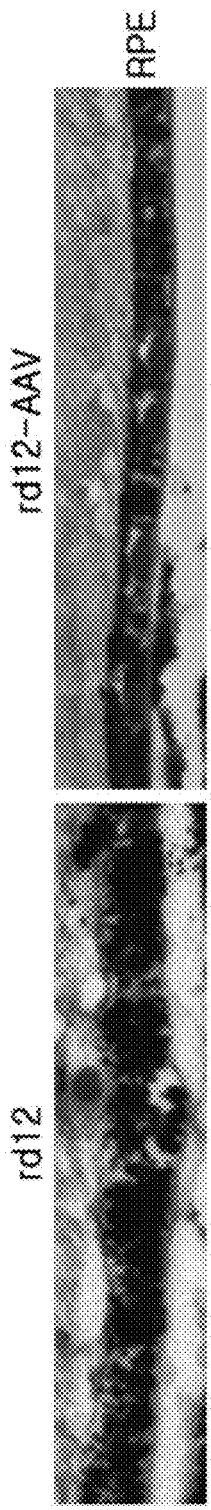
FIG. 22 shows representative H & E images of the RPE layer of rd12 mice at 7 months after a dual AAV system encoding SpCas9 and a donor template is not treated or treated (Scale bar, 20 μm).

As a result of off-target analysis for 33 homologous sites which are different from the TS4$^{rd12}$ sgRNA sequence by up to three nucleotides, no meaningful mutations were observed at predicted genomic loci of AAV-treated rd12 mice (FIG. 21). In addition, there was no definite evidence of histologic perturbation or tumorigenesis for 7 months (FIG. 22).

TABLE 6

Active off-target sites (mismatched nucleotide sequence: lowercase letters; PAM sequence: underlined)

| Targets | Chromosome | Location | Sequence (5' to 3') | Related genes | SEQ ID NO |
|---|---|---|---|---|---|
| ON | Chr3 | 159601555 | ACTGGCAGTCTCCTCTGATGTGG | RPE65 | SEQ ID NO: 172 |
| Off1 | chr8 | 120281151 | AaaGGCAGTCTCCTCTGAaGTGG | Intron (Col14a1) | SEQ ID NO: 173 |
| Off2 | chr1 | 78346963 | taTGGCAGTCTtCTCTGATGGGG | Intron (Sgpp2) | SEQ ID NO: 174 |
| Off5 | chr12 | 6921883 | AgaGGCAGTCTCCTCTGAgGAGG | Intron (Eno2) | SEQ ID NO: 175 |
| Off9 | chr8 | 5604333 | ACTaGCAtTCcCCTaTGATGGGG | Intergenic | SEQ ID NO: 176 |
| Off10 | chr14 | 37095194 | taaaGCAGTCTtCTCTGATGGGG | Intron (Cdhr1) | SEQ ID NO: 177 |
| Off11 | chr12 | 28831482 | ACTGGaAGcCTtCTCTGATGAGG | Intron (Tssc1) | SEQ ID NO: 178 |

INDUSTRIAL APPLICABILITY

A therapeutic agent for a retinal dysfunction disease may be obtained using a composition for gene manipulation which can artificially manipulate a retinal function-forming gene. For example, the composition for gene manipulation, which includes a guide nucleic acid targeting the retinal function-forming gene, can be used as an effective therapeutic agent for retinal dysfunction by allowing the retinal function-forming gene to be normally function or to be normally expressed by artificially manipulating and/or correcting the retinal function-forming gene.

Sequence Listing Free-Text

Target sequences of retinal function-forming gene and primer sequences used in examples.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for treating a retinal dysfunction disease, the method comprising administration of a composition for gene manipulation into a subject to be treated,
   wherein the composition for gene manipulation comprises:
   a guide RNA or a nucleic acid encoding the same,
   wherein the guide RNA targets a target region present in a retinal pigment epithelium-specific 65 kDa protein (RPE65) gene,
   wherein the target region has two strands having a guide nucleic acid-binding sequence and a guide nucleic acid-non binding sequence, which are sequences of 15 to 25 contiguous nucleotides,
   wherein the guide RNA comprises
      a guide sequence complementary binding with the guide nucleic acid-binding sequence of the target region; and
      a guide RNA comprises a nucleotide sequence comprising SEQ ID NO: 225, SEQ ID NO: 228, SEQ ID NO: 231, and SEQ ID NO: 233 arranged in a direction of 5' to 3', or a nucleotide sequence having 80% or more homologous therewith
   wherein the guide sequence is a RNA sequence having homology with the guide nucleic acid-non binding sequence of the target region,
   wherein the guide nucleic acid-non binding sequence of the target region in the RPE65 gene is selected from the group consisting of SEQ ID NOs: 1 to 44,
   wherein the guide sequence includes 0 to 5 nucleotides mismatched with the guide nucleic acid-binding sequence of the target region,
   and
   a Cas9 protein or a nucleic acid encoding the same,
   wherein the Cas9 protein is a *Streptococcus pyogenes*-derived Cas9 protein,
   a donor comprising a nucleic acid encoding a part of RPE65, wherein the Cas9 protein is complexed with the guide RNA to manipulate the RPE65 gene,
   wherein the nucleic acid encoding the part of RPE65 comprises one or more synonymous mutations compared to wild type sequence thereof, so as to prevent a donor cleavage and a recleavage of a Rpe65 locus repaired after homology directed repair (HDR).

2. The method of claim 1, wherein the retinal dysfunction disease is Leber congenital amaurosis (LCA), retinal pigmentosa, Stargardt disease, retinal dysplasia, choroideremia, macular degeneration, myopic choroidal neovascularization (CNV), polypoidal choroidal vasculopathy (PCV), or central serous chorioretinopathy (CSCR.

3. The method of claim 1, wherein the administration is performed by injection, transfusion, implantation or transplantation.

4. The method of claim 1, wherein the administration is performed via an administration route selected from sub-retinal, intraocular, intravitreal, intramuscular or intravenous routes.

5. The method of claim 1, wherein the administration is performed by injection.

6. The method of claim 1, wherein the administration is performed via subretinal.

7. The method of claim 1, wherein the RPE65 gene comprises one or more nucleotides which are mutated, compared to a wild type RPE65 gene.

8. The method of claim 1, wherein the nucleic acid encoding the guide RNA, the nucleic acid encoding the Cas9 protein, and the donor are contained in one or more vectors.

9. The method of claim 1, wherein the guide nucleic acid-non binding sequence is selected from the group consisting of SEQ ID NOs: 1, 2, 3, 4, 5, 6, 7, 9, 12, 14, 16, 17, 18, 20, and 21.

10. The method of claim 1, wherein the guide nucleic acid-non binding sequence is SEQ ID NO: 6.

* * * * *